United States Patent
Fitz et al.

(10) Patent No.: US 8,682,052 B2
(45) Date of Patent: Mar. 25, 2014

(54) IMPLANTS FOR ALTERING WEAR PATTERNS OF ARTICULAR SURFACES

(75) Inventors: Wolfgang Fitz, Sherborn, MA (US); Raymond Bojarski, Attleboro, MA (US); Philipp Lang, Lexington, MA (US)

(73) Assignee: ConforMIS, Inc., Bedford, MA (US)

( * ) Notice: Subject to any disclaimer, the term of this patent is extended or adjusted under 35 U.S.C. 154(b) by 1199 days.

(21) Appl. No.: 12/398,598

(22) Filed: Mar. 5, 2009

(65) Prior Publication Data

US 2009/0226068 A1    Sep. 10, 2009

Related U.S. Application Data

(60) Provisional application No. 61/034,035, filed on Mar. 5, 2008.

(51) Int. Cl.
*A61F 2/38* (2006.01)

(52) U.S. Cl.
USPC .................. 382/131; 382/128; 623/14.12

(58) Field of Classification Search
USPC .............. 382/128, 131; 703/1; 623/16.11
See application file for complete search history.

(56) References Cited

U.S. PATENT DOCUMENTS

| | | | |
|---|---|---|---|
| 3,314,420 A | 4/1967 | Smith et al. ............. 128/92 |
| 3,605,123 A | 9/1971 | Hahn ....................... 3/1 |
| 3,694,820 A | 10/1972 | Scales et al. ............ 3/1 |
| 3,798,679 A | 3/1974 | Ewald ..................... 3/1 |
| 3,808,606 A | 5/1974 | Tronzo .................... 3/1 |
| 3,816,855 A | 6/1974 | Saleh ...................... 3/1 |
| 3,843,975 A | 10/1974 | Tronzo .................... 3/1 |
| 3,852,830 A | 12/1974 | Marmor ................... 3/1 |
| 3,855,638 A | 12/1974 | Pilliar ..................... 3/1 |
| 3,938,198 A | 2/1976 | Kahn et al. ............... 3/1.912 |
| 3,987,499 A | 10/1976 | Scharbach et al. ........ 3/1.91 |
| 3,991,425 A | 11/1976 | Martin et al. ............. 3/1.91 |
| 4,052,753 A | 10/1977 | Dedo ...................... 3/1 |
| 4,055,862 A | 11/1977 | Farling ................... 3/1.91 |
| 4,085,466 A | 4/1978 | Goodfellow et al. ...... 3/1.91 |
| 4,098,626 A | 7/1978 | Graham et al. ........... 149/19.4 |
| 4,164,793 A | 8/1979 | Swanson .................. 3/1.91 |

(Continued)

FOREIGN PATENT DOCUMENTS

| CN | 86209787 | 11/1987 | ............ A61F 2/38 |
|---|---|---|---|
| CN | 2305966 | 2/1999 | ............ A61F 2/28 |

(Continued)

OTHER PUBLICATIONS

International Searching Authority, International Search Report—International Application No. PCT/US2009/036165, dated May 7, 2009, together with the Written Opinion of the International Searching Authority, 9 pages.

(Continued)

*Primary Examiner* — Howard Weiss
*Assistant Examiner* — Tifney Skyles
(74) *Attorney, Agent, or Firm* — Sunstein Kann Murphy & Timbers LLP

(57) ABSTRACT

Methods and devices for correcting wear pattern defects in joints. The methods and devices described herein allow for the restoration of correcting abnormal biomechanical loading conditions in a joint brought on by wear pattern defects, and also can, in embodiments, permit correction of proper kinematic movement.

52 Claims, 45 Drawing Sheets

(56) References Cited

U.S. PATENT DOCUMENTS

| | | | |
|---|---|---|---|
| 4,178,641 A | 12/1979 | Grundei et al. | 3/1.911 |
| 4,203,444 A | 5/1980 | Bonnell et al. | 128/276 |
| 4,207,627 A | 6/1980 | Cloutier | 3/1.911 |
| 4,211,228 A | 7/1980 | Cloutier | 128/303 R |
| 4,213,816 A | 7/1980 | Morris | 156/245 |
| 4,219,893 A | 9/1980 | Noiles | 3/1.911 |
| 4,280,231 A | 7/1981 | Swanson | 3/1.91 |
| 4,309,778 A | 1/1982 | Buechel et al. | 3/1.911 |
| 4,340,978 A | 7/1982 | Buechel et al. | 3/1.911 |
| 4,344,193 A | 8/1982 | Kenny | 3/1.911 |
| 4,368,040 A | 1/1983 | Weissman | 433/36 |
| 4,436,684 A | 3/1984 | White | 264/138 |
| 4,459,985 A | 7/1984 | McKay et al. | 128/303 R |
| 4,502,161 A | 3/1985 | Wall | 3/1.91 |
| 4,575,805 A | 3/1986 | Moermann et al. | 364/474 |
| 4,586,496 A | 5/1986 | Keller | 128/92 E |
| 4,594,380 A | 6/1986 | Chapin et al. | 524/144 |
| 4,601,290 A | 7/1986 | Effron et al. | 128/305 |
| 4,609,551 A | 9/1986 | Caplan et al. | 424/95 |
| 4,627,853 A | 12/1986 | Campbell et al. | 623/16 |
| 4,655,227 A | 4/1987 | Gracovetsky | 128/781 |
| 4,699,156 A | 10/1987 | Gracovetsky | 128/781 |
| 4,714,472 A | 12/1987 | Averill et al. | 623/20 |
| 4,714,474 A | 12/1987 | Brooks, Jr. et al. | 623/20 |
| 4,769,040 A | 9/1988 | Wevers | 623/20 |
| 4,813,436 A | 3/1989 | Au | 128/779 |
| 4,822,365 A | 4/1989 | Walker et al. | 623/20 |
| 4,823,807 A | 4/1989 | Russell et al. | 128/773 |
| 4,846,835 A | 7/1989 | Grande | 623/11 |
| 4,865,607 A | 9/1989 | Witzel et al. | 623/20 |
| 4,872,452 A | 10/1989 | Alexson | 128/92 VJ |
| 4,880,429 A | 11/1989 | Stone | 623/18 |
| 4,883,488 A | 11/1989 | Bloebaum et al. | |
| 4,888,021 A | 12/1989 | Forte et al. | 623/20 |
| 4,936,862 A | 6/1990 | Walker et al. | 623/23 |
| 4,944,757 A | 7/1990 | Martinez et al. | 623/20 |
| 5,019,103 A | 5/1991 | Van Zile et al. | 623/20 |
| 5,021,061 A | 6/1991 | Wevers et al. | 623/20 |
| 5,041,138 A | 8/1991 | Vacanti et al. | 623/16 |
| 5,047,057 A | 9/1991 | Lawes | 623/20 |
| 5,059,216 A | 10/1991 | Winters | 623/20 |
| 5,067,964 A | 11/1991 | Richmond et al. | 623/18 |
| 5,099,859 A | 3/1992 | Bell | 128/781 |
| 5,108,452 A | 4/1992 | Fallin | 623/23 |
| 5,123,927 A | 6/1992 | Duncan et al. | 623/20 |
| 5,129,908 A | 7/1992 | Peterson | 606/88 |
| 5,133,759 A | 7/1992 | Turner | 623/20 |
| 5,150,304 A | 9/1992 | Berchem et al. | 364/474.24 |
| 5,154,178 A | 10/1992 | Shah | 128/653.2 |
| 5,162,430 A | 11/1992 | Rhee et al. | 525/54.1 |
| 5,171,322 A | 12/1992 | Kenny | 623/18 |
| 5,197,985 A | 3/1993 | Caplan et al. | 623/16 |
| 5,206,023 A | 4/1993 | Hunziker | 424/423 |
| 5,226,914 A | 7/1993 | Caplan et al. | 623/16 |
| 5,234,433 A | 8/1993 | Bert et al. | 606/88 |
| 5,245,282 A | 9/1993 | Mugler, III et al. | 324/309 |
| 5,246,013 A | 9/1993 | Frank et al. | 128/774 |
| 5,246,530 A | 9/1993 | Bugle et al. | 156/643 |
| 5,270,300 A | 12/1993 | Hunziker | 514/12 |
| 5,274,565 A | 12/1993 | Reuben | 364/474.24 |
| 5,282,868 A | 2/1994 | Bahler | 623/20 |
| 5,288,797 A | 2/1994 | Khalil et al. | 524/872 |
| 5,303,148 A | 4/1994 | Mattson et al. | 364/413.01 |
| 5,306,307 A | 4/1994 | Senter et al. | 623/17 |
| 5,306,311 A | 4/1994 | Stone et al. | 623/18 |
| 5,314,478 A | 5/1994 | Oka et al. | 623/18 |
| 5,314,482 A | 5/1994 | Goodfellow et al. | 623/20 |
| 5,320,102 A | 6/1994 | Paul et al. | 128/653.2 |
| 5,326,363 A | 7/1994 | Aikins | 623/20 |
| 5,326,365 A | 7/1994 | Alvine | 623/21 |
| 5,344,459 A | 9/1994 | Swartz | 623/18 |
| 5,360,446 A | 11/1994 | Kennedy | 623/16 |
| 5,365,996 A | 11/1994 | Crook | 164/45 |
| 5,368,858 A | 11/1994 | Hunziker | 424/423 |
| 5,413,116 A | 5/1995 | Radke et al. | 128/777 |
| 5,423,828 A | 6/1995 | Benson | 606/102 |
| 5,433,215 A | 7/1995 | Athanasiou et al. | 128/774 |
| 5,445,152 A | 8/1995 | Bell et al. | 128/653.5 |
| 5,448,489 A | 9/1995 | Reuben | 364/474.05 |
| 5,468,787 A | 11/1995 | Braden et al. | 523/113 |
| 5,478,739 A | 12/1995 | Slivka et al. | 435/240.23 |
| 5,489,309 A | 2/1996 | Lackey et al. | 623/19 |
| 5,501,687 A | 3/1996 | Willert et al. | 606/94 |
| 5,503,162 A | 4/1996 | Athanasiou et al. | 128/774 |
| 5,507,820 A | 4/1996 | Pappas | 623/20 |
| 5,510,121 A | 4/1996 | Rhee et al. | 424/520 |
| 5,522,900 A | 6/1996 | Hollister | 623/18 |
| 5,523,843 A | 6/1996 | Yamane et al. | 356/363 |
| 5,541,515 A | 7/1996 | Tsujita | 324/318 |
| 5,549,690 A | 8/1996 | Hollister et al. | 623/21 |
| 5,554,190 A | 9/1996 | Draenert | 623/16 |
| 5,556,432 A | 9/1996 | Kubein-Meesenburg et al. | 623/20 |
| 5,560,096 A | 10/1996 | Stephens | 29/558 |
| 5,564,437 A | 10/1996 | Bainville et al. | 128/774 |
| 5,571,191 A | 11/1996 | Fitz | 623/17 |
| 5,571,205 A | 11/1996 | James | 623/24 |
| 5,609,640 A | 3/1997 | Johnson | 623/20 |
| 5,611,802 A | 3/1997 | Samuelson et al. | 606/86 |
| 5,616,146 A | 4/1997 | Murray | 606/80 |
| 5,632,745 A | 5/1997 | Schwartz | 606/75 |
| 5,671,741 A | 9/1997 | Lang et al. | 128/653.2 |
| 5,681,354 A | 10/1997 | Eckhoff | 623/20 |
| 5,682,886 A | 11/1997 | Delp et al. | 128/653.1 |
| 5,683,466 A | 11/1997 | Vitale | 623/18 |
| 5,683,468 A | 11/1997 | Pappas | 623/20 |
| 5,684,562 A | 11/1997 | Fujieda | 351/212 |
| 5,687,210 A | 11/1997 | Maitrejean et al. | 378/57 |
| 5,690,635 A | 11/1997 | Matsen, III et al. | 606/88 |
| 5,702,463 A | 12/1997 | Pothier et al. | 623/20 |
| 5,723,331 A | 3/1998 | Tubo et al. | 435/366 |
| 5,728,162 A | 3/1998 | Eckhoff | 623/20 |
| 5,735,277 A | 4/1998 | Schuster | 128/653.1 |
| 5,749,362 A | 5/1998 | Funda et al. | 128/653.1 |
| 5,749,874 A | 5/1998 | Schwartz | 606/75 |
| 5,749,876 A | 5/1998 | Duvillier et al. | 606/88 |
| 5,759,205 A | 6/1998 | Valentini | 623/16 |
| 5,768,134 A | 6/1998 | Swaelens et al. | 364/468.28 |
| 5,769,899 A | 6/1998 | Schwartz et al. | 623/18 |
| 5,772,595 A | 6/1998 | Votruba et al. | 600/415 |
| 5,779,651 A | 7/1998 | Buschmann et al. | 600/587 |
| 5,786,217 A | 7/1998 | Tubo et al. | 435/402 |
| 5,810,006 A | 9/1998 | Votruba et al. | 128/653.2 |
| 5,824,085 A | 10/1998 | Sahay et al. | 623/16 |
| 5,824,102 A | 10/1998 | Buscayret | 623/20 |
| 5,827,289 A | 10/1998 | Reiley et al. | 606/86 |
| 5,832,422 A | 11/1998 | Wiedenhoefer | 702/154 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,871,018 A | 2/1999 | Delp et al. | 128/898 |
| 5,871,540 A | 2/1999 | Weissman et al. | 623/20 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia, III et al. | 364/578 |
| 5,885,296 A | 3/1999 | Masini | 606/86 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,934 A | 5/1999 | Grande et al. | 435/325 |
| 5,913,821 A | 6/1999 | Farese et al. | 600/425 |
| 5,916,220 A | 6/1999 | Masini | 606/88 |
| 5,928,945 A | 7/1999 | Seliktar et al. | 435/395 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,972,385 A | 10/1999 | Liu et al. | 424/486 |
| 5,995,738 A | 11/1999 | DiGioia, III et al. | 395/500.32 |
| 6,002,859 A | 12/1999 | DiGioia, III et al. | 395/500.32 |
| 6,013,103 A | 1/2000 | Kaufman et al. | 623/20 |

(56) References Cited

U.S. PATENT DOCUMENTS

| | | | |
|---|---|---|---|
| 6,046,379 A | 4/2000 | Stone et al. | 623/11 |
| 6,057,927 A | 5/2000 | Lévesque et al. | 356/432 T |
| 6,078,680 A | 6/2000 | Yoshida et al. | 382/128 |
| 6,081,577 A | 6/2000 | Webber | 378/23 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,102,916 A | 8/2000 | Masini | 606/88 |
| 6,102,955 A | 8/2000 | Mendes et al. | 623/20 |
| 6,110,209 A | 8/2000 | Stone | 623/16.11 |
| 6,112,109 A | 8/2000 | D'Urso | 600/407 |
| 6,120,541 A | 9/2000 | Johnson | 623/14.12 |
| 6,126,690 A | 10/2000 | Ateshian et al. | 623/18 |
| 6,139,578 A | 10/2000 | Lee et al. | 623/16.11 |
| 6,146,422 A | 11/2000 | Lawson | 623/17.16 |
| 6,151,521 A | 11/2000 | Guo et al. | 600/407 |
| 6,152,960 A | 11/2000 | Pappas | 623/20.31 |
| 6,156,069 A | 12/2000 | Amstutz | 623/22.11 |
| 6,161,080 A | 12/2000 | Aouni-Ateshian et al. | 703/11 |
| 6,162,208 A | 12/2000 | Hipps | 606/1 |
| 6,165,221 A | 12/2000 | Schmotzer | 623/20.11 |
| 6,171,340 B1 | 1/2001 | McDowell | 623/18.11 |
| 6,175,655 B1 | 1/2001 | George, III et al. | 382/257 |
| 6,178,225 B1 | 1/2001 | Zur et al. | 378/98.2 |
| 6,187,010 B1 | 2/2001 | Masini | 606/86 |
| 6,197,064 B1 | 3/2001 | Haines et al. | 623/20.31 |
| 6,197,325 B1 | 3/2001 | MacPhee et al. | 424/426 |
| 6,200,606 B1 | 3/2001 | Peterson et al. | 424/574 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,249,692 B1 | 6/2001 | Cowin | 600/407 |
| 6,251,143 B1 | 6/2001 | Schwartz et al. | 623/23.72 |
| 6,254,639 B1 | 7/2001 | Peckitt | 623/11.11 |
| 6,261,296 B1 | 7/2001 | Aebi et al. | 606/90 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,289,115 B1 | 9/2001 | Takeo | 382/130 |
| 6,289,753 B1 | 9/2001 | Basser et al. | 73/866 |
| 6,299,645 B1 | 10/2001 | Ogden | 623/20.21 |
| 6,299,905 B1 | 10/2001 | Peterson et al. | 424/486 |
| 6,302,582 B1 | 10/2001 | Nord et al. | 378/207 |
| 6,310,477 B1 | 10/2001 | Schneider | 324/307 |
| 6,310,619 B1 | 10/2001 | Rice | 345/420 |
| 6,316,153 B1 | 11/2001 | Goodman et al. | 430/8 |
| 6,319,712 B1 | 11/2001 | Meenen et al. | 435/395 |
| 6,322,588 B1 | 11/2001 | Ogle et al. | 623/1.46 |
| 6,328,765 B1 | 12/2001 | Hardwick et al. | 623/23.72 |
| 6,334,006 B1 | 12/2001 | Tanabe | 385/12 |
| 6,334,066 B1 | 12/2001 | Rupprecht et al. | 600/411 |
| 6,342,075 B1 | 1/2002 | MacArthur | 623/20.14 |
| 6,344,059 B1 | 2/2002 | Krakovits et al. | 623/20.31 |
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,379,388 B1 | 4/2002 | Ensign et al. | 623/20.34 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,429,013 B1 | 8/2002 | Halvorsen et al. | 435/377 |
| 6,443,988 B2 | 9/2002 | Felt et al. | 623/17.12 |
| 6,443,991 B1 | 9/2002 | Running | 623/20.27 |
| 6,444,222 B1 | 9/2002 | Asculai et al. | 424/484 |
| 6,450,978 B1 | 9/2002 | Brosseau et al. | 600/595 |
| 6,459,948 B1 | 10/2002 | Ateshian et al. | 700/117 |
| 6,468,314 B2 | 10/2002 | Schwartz et al. | 623/23.72 |
| 6,479,996 B1 | 11/2002 | Hoogeveen et al. | 324/309 |
| 6,482,209 B1 | 11/2002 | Engh et al. | 606/79 |
| 6,510,334 B1 | 1/2003 | Schuster et al. | 600/407 |
| 6,514,514 B1 | 2/2003 | Atkinson et al. | 424/423 |
| 6,520,964 B2 | 2/2003 | Tallarida et al. | 396/567 |
| 6,533,737 B1 | 3/2003 | Brosseau et al. | 600/595 |
| 6,556,855 B2 | 4/2003 | Thesen | 600/419 |
| 6,558,421 B1 | 5/2003 | Fell et al. | 623/14.12 |
| 6,560,476 B1 | 5/2003 | Pelletier et al. | 600/410 |
| 6,575,980 B1 | 6/2003 | Robie et al. | 606/88 |
| 6,591,581 B2 | 7/2003 | Schmieding | 53/396 |
| 6,592,624 B1 | 7/2003 | Fraser et al. | 623/17.16 |
| 6,623,526 B1 | 9/2003 | Lloyd | 623/20.28 |
| 6,626,945 B2 | 9/2003 | Simon et al. | 623/17.19 |
| 6,632,235 B2 | 10/2003 | Weikel et al. | 606/192 |
| 6,652,587 B2 | 11/2003 | Felt et al. | 623/20.16 |
| 6,679,917 B2 | 1/2004 | Ek | 623/20.14 |
| 6,690,816 B2 | 2/2004 | Aylward et al. | 382/128 |
| 6,692,448 B2 | 2/2004 | Tanaka et al. | 600/587 |
| 6,702,821 B2 | 3/2004 | Bonutti | 606/88 |
| 6,712,856 B1 | 3/2004 | Carignan et al. | 623/20.35 |
| 6,719,794 B2 | 4/2004 | Gerber et al. | 623/17.11 |
| 6,770,078 B2 | 8/2004 | Bonutti | 606/88 |
| 6,772,026 B2 | 8/2004 | Bradbury et al. | 700/98 |
| 6,799,066 B2 | 9/2004 | Steines et al. | 600/407 |
| 6,816,607 B2 | 11/2004 | O'Donnell et al. | 382/131 |
| 6,835,377 B2 | 12/2004 | Goldberg et al. | 424/93.7 |
| 6,855,165 B2 | 2/2005 | Fell et al. | 623/14.12 |
| 6,873,741 B2 | 3/2005 | Li | 382/266 |
| 6,893,463 B2 | 5/2005 | Fell et al. | 623/14.12 |
| 6,893,467 B1 | 5/2005 | Bercovy | 623/20.14 |
| 6,905,514 B2 | 6/2005 | Carignan et al. | 623/20.35 |
| 6,911,044 B2 | 6/2005 | Fell et al. | 623/14.12 |
| 6,916,341 B2 | 7/2005 | Rolston | 623/20.3 |
| 6,923,831 B2 | 8/2005 | Fell et al. | 623/14.12 |
| 6,932,842 B1 | 8/2005 | Litschko et al. | 623/16.11 |
| 6,964,687 B1 | 11/2005 | Bernard et al. | 623/17.16 |
| 6,966,928 B2 | 11/2005 | Fell et al. | 623/14.12 |
| 6,984,981 B2 | 1/2006 | Tamez-Peña et al. | 324/309 |
| 6,998,841 B1 | 2/2006 | Tamez-Peña et al. | 324/302 |
| 7,020,314 B1 | 3/2006 | Suri et al. | 382/130 |
| 7,050,534 B2 | 5/2006 | Lang | 378/54 |
| 7,058,159 B2 | 6/2006 | Lang et al. | 378/54 |
| 7,058,209 B2 | 6/2006 | Chen et al. | 382/117 |
| 7,060,101 B2 | 6/2006 | O'Connor et al. | 623/20.32 |
| 7,105,026 B2 | 9/2006 | Johnson et al. | 623/20.14 |
| 7,115,131 B2 | 10/2006 | Engh et al. | 606/79 |
| 7,174,282 B2 | 2/2007 | Hollister et al. | 703/2 |
| 7,184,814 B2 | 2/2007 | Lang et al. | 600/416 |
| 7,204,807 B2 | 4/2007 | Tsoref | 600/438 |
| 7,238,203 B2 | 7/2007 | Bagga et al. | 623/17.11 |
| 7,239,908 B1 | 7/2007 | Alexander et al. | 600/427 |
| 7,244,273 B2 | 7/2007 | Pedersen et al. | 623/14.12 |
| 7,245,697 B2 | 7/2007 | Lang | 378/54 |
| 7,292,674 B2 | 11/2007 | Lang | 378/54 |
| 7,326,252 B2 | 2/2008 | Otto et al. | 623/20.15 |
| 7,379,529 B2 | 5/2008 | Lang | 378/54 |
| 7,438,685 B2 | 10/2008 | Burdette et al. | 600/439 |
| 7,467,892 B2 | 12/2008 | Lang et al. | 378/207 |
| 7,468,075 B2 | 12/2008 | Lang et al. | 623/16.11 |
| 7,520,901 B2 | 4/2009 | Engh et al. | 623/20.21 |
| 7,534,263 B2 | 5/2009 | Burdulis, Jr. et al. | 623/14.12 |
| 7,603,192 B2 | 10/2009 | Martin et al. | 700/98 |
| 7,611,519 B2 | 11/2009 | Lefevre et al. | 606/102 |
| 7,611,653 B1 | 11/2009 | Elsner et al. | 264/255 |
| 7,615,054 B1 | 11/2009 | Bonutti | 606/88 |
| 7,618,451 B2 | 11/2009 | Berez et al. | 623/14.12 |
| 7,634,119 B2 | 12/2009 | Tsougarakis et al. | 382/128 |
| 7,796,791 B2 | 9/2010 | Tsougarakis et al. | 382/128 |
| 7,799,077 B2 | 9/2010 | Lang et al. | 623/14.12 |
| 7,806,896 B1 | 10/2010 | Bonutti | 606/86 R |
| 7,842,092 B2 | 11/2010 | Otto et al. | 623/18.11 |
| 7,881,768 B2 | 2/2011 | Lang et al. | 600/407 |
| 7,914,582 B2 | 3/2011 | Felt et al. | 623/20.16 |
| 7,981,158 B2 | 7/2011 | Fitz et al. | 623/17.16 |
| 7,983,777 B2 | 7/2011 | Melton et al. | 700/98 |
| 8,036,729 B2 | 10/2011 | Lang et al. | 600/407 |

(56) References Cited

U.S. PATENT DOCUMENTS

| | | | |
|---|---|---|---|
| 8,062,302 B2 | 11/2011 | Lang et al. | 606/87 |
| 8,066,708 B2 | 11/2011 | Lang et al. | 606/88 |
| 8,070,821 B2 | 12/2011 | Roger | 623/20.17 |
| 8,077,950 B2 | 12/2011 | Tsougarakis et al. | 382/128 |
| 8,083,745 B2 | 12/2011 | Lang et al. | 606/87 |
| 8,094,900 B2 | 1/2012 | Steines et al. | 382/128 |
| 8,105,330 B2 | 1/2012 | Fitz et al. | 606/88 |
| 8,112,142 B2 | 2/2012 | Alexander et al. | 600/407 |
| RE43,282 E | 3/2012 | Alexander et al. | 600/427 |
| 8,192,498 B2 | 6/2012 | Wagner et al. | 623/20.21 |
| 8,211,181 B2 | 7/2012 | Walker | 623/20.21 |
| 8,234,097 B2 | 7/2012 | Steines et al. | 703/1 |
| 8,236,061 B2 | 8/2012 | Heldreth et al. | 623/20.31 |
| 8,265,730 B2 | 9/2012 | Alexander et al. | 600/410 |
| 8,306,601 B2 | 11/2012 | Lang et al. | 600/407 |
| 8,337,501 B2 | 12/2012 | Fitz et al. | 606/86 R |
| 8,337,507 B2 | 12/2012 | Lang et al. | 606/102 |
| 8,343,218 B2 | 1/2013 | Lang et al. | 623/16.11 |
| 8,366,771 B2 | 2/2013 | Burdulis, Jr. et al. | 623/14.12 |
| 8,369,926 B2 | 2/2013 | Lang et al. | 600/407 |
| 8,377,129 B2 | 2/2013 | Fitz et al. | 623/14.12 |
| 8,439,926 B2 | 5/2013 | Bojarski et al. | 606/88 |
| 8,460,304 B2 | 6/2013 | Fitz et al. | 606/88 |
| 2001/0001120 A1 | 5/2001 | Masini | 606/86 |
| 2001/0010023 A1 | 7/2001 | Schwartz et al. | 623/23.72 |
| 2001/0039455 A1 | 11/2001 | Simon et al. | 623/23.51 |
| 2002/0013626 A1 | 1/2002 | Geistlich et al. | 623/23.57 |
| 2002/0016543 A1 | 2/2002 | Tyler | 600/410 |
| 2002/0022884 A1 | 2/2002 | Mansmann | 623/14.12 |
| 2002/0045940 A1 | 4/2002 | Giannetti et al. | 623/11.11 |
| 2002/0059049 A1 | 5/2002 | Bradbury et al. | 703/11 |
| 2002/0067798 A1 | 6/2002 | Lang et al. | 378/54 |
| 2002/0068979 A1 | 6/2002 | Brown et al. | 623/20.3 |
| 2002/0072821 A1 | 6/2002 | Baker | 700/98 |
| 2002/0082703 A1 | 6/2002 | Repicci | 623/20.29 |
| 2002/0087274 A1 | 7/2002 | Alexander et al. | 702/19 |
| 2002/0106625 A1 | 8/2002 | Hung et al. | 435/1.1 |
| 2002/0111694 A1 | 8/2002 | Ellingsen et al. | 623/23.57 |
| 2002/0115647 A1 | 8/2002 | Halvorsen et al. | 514/171 |
| 2002/0120274 A1 | 8/2002 | Overaker et al. | 606/72 |
| 2002/0120281 A1 | 8/2002 | Overaker | 606/151 |
| 2002/0127264 A1 | 9/2002 | Felt et al. | 424/423 |
| 2002/0133230 A1 | 9/2002 | Repicci | 623/14.12 |
| 2002/0147392 A1 | 10/2002 | Steines et al. | 600/407 |
| 2002/0151986 A1 | 10/2002 | Asculai et al. | 424/484 |
| 2002/0156150 A1 | 10/2002 | Williams et al. | 523/113 |
| 2002/0173852 A1 | 11/2002 | Felt et al. | 623/20.32 |
| 2002/0177770 A1 | 11/2002 | Lang et al. | 600/410 |
| 2002/0183850 A1 | 12/2002 | Felt et al. | 623/20.16 |
| 2003/0015208 A1 | 1/2003 | Lang et al. | 128/922 |
| 2003/0031292 A1 | 2/2003 | Lang | 378/54 |
| 2003/0035773 A1 | 2/2003 | Totterman et al. | 424/9.1 |
| 2003/0045935 A1 | 3/2003 | Angelucci et al. | 623/17.11 |
| 2003/0055500 A1 | 3/2003 | Fell et al. | 623/14.12 |
| 2003/0055501 A1 | 3/2003 | Fell et al. | 623/14.12 |
| 2003/0055502 A1 | 3/2003 | Lang et al. | 623/16.11 |
| 2003/0060882 A1 | 3/2003 | Fell et al. | 623/14.12 |
| 2003/0060883 A1 | 3/2003 | Fell et al. | 623/14.12 |
| 2003/0060884 A1 | 3/2003 | Fell et al. | 623/14.12 |
| 2003/0060885 A1 | 3/2003 | Fell et al. | 623/14.12 |
| 2003/0063704 A1 | 4/2003 | Lang | 378/54 |
| 2003/0069591 A1 | 4/2003 | Carson et al. | 606/130 |
| 2003/0100953 A1 | 5/2003 | Rosa et al. | 623/20.3 |
| 2003/0158606 A1 | 8/2003 | Coon et al. | 623/20.15 |
| 2003/0216669 A1 | 11/2003 | Lang et al. | 600/587 |
| 2003/0225457 A1 | 12/2003 | Justin et al. | 623/20.14 |
| 2003/0236473 A1 | 12/2003 | Dore et al. | 600/587 |
| 2004/0006393 A1 | 1/2004 | Burkinshaw | 623/20.3 |
| 2004/0062358 A1 | 4/2004 | Lang et al. | 378/207 |
| 2004/0081287 A1 | 4/2004 | Lang et al. | 378/210 |
| 2004/0098132 A1 | 5/2004 | Andriacchi et al. | 623/20.35 |
| 2004/0098133 A1 | 5/2004 | Carignan et al. | 623/20.35 |
| 2004/0102851 A1 | 5/2004 | Saladino | 623/20.15 |
| 2004/0102852 A1 | 5/2004 | Johnson et al. | 623/20.15 |
| 2004/0117015 A1 | 6/2004 | Biscup | 623/16.11 |
| 2004/0117023 A1 | 6/2004 | Gerbec et al. | 623/18.11 |
| 2004/0122521 A1 | 6/2004 | Lee et al. | 623/20.15 |
| 2004/0133276 A1 | 7/2004 | Lang et al. | 623/14.12 |
| 2004/0138754 A1 | 7/2004 | Lang et al. | 623/20.14 |
| 2004/0138755 A1 | 7/2004 | O'Connor et al. | 623/20.32 |
| 2004/0147927 A1 | 7/2004 | Tsougarakis et al. | 606/53 |
| 2004/0153079 A1 | 8/2004 | Tsougarakis et al. | 606/77 |
| 2004/0153162 A1 | 8/2004 | Sanford et al. | 623/20.3 |
| 2004/0153164 A1 | 8/2004 | Sanford et al. | 623/20.29 |
| 2004/0167390 A1 | 8/2004 | Alexander et al. | 600/410 |
| 2004/0167630 A1 | 8/2004 | Rolston | 623/20.14 |
| 2004/0193280 A1 | 9/2004 | Webster et al. | 623/20.33 |
| 2004/0204644 A1 | 10/2004 | Tsougarakis et al. | 600/410 |
| 2004/0204760 A1 | 10/2004 | Fitz et al. | 623/14.12 |
| 2004/0204766 A1 | 10/2004 | Siebel | 623/20.31 |
| 2004/0236424 A1 | 11/2004 | Berez et al. | 623/14.12 |
| 2005/0010106 A1 | 1/2005 | Lang et al. | 600/425 |
| 2005/0015153 A1 | 1/2005 | Goble et al. | 623/23.46 |
| 2005/0021042 A1 | 1/2005 | Marnay et al. | 606/99 |
| 2005/0033424 A1 | 2/2005 | Fell | 623/14.12 |
| 2005/0043807 A1 | 2/2005 | Wood | 623/20.14 |
| 2005/0055028 A1 | 3/2005 | Haines | 606/79 |
| 2005/0078802 A1 | 4/2005 | Lang et al. | 387/207 |
| 2005/0107883 A1 | 5/2005 | Goodfried et al. | 623/20.15 |
| 2005/0107884 A1 | 5/2005 | Johnson et al. | 623/20.15 |
| 2005/0119664 A1 | 6/2005 | Carignan et al. | 606/96 |
| 2005/0125029 A1 | 6/2005 | Bernard et al. | 606/205 |
| 2005/0154471 A1 | 7/2005 | Aram et al. | 623/20.15 |
| 2005/0171612 A1 | 8/2005 | Rolston | 623/20.19 |
| 2005/0203384 A1 | 9/2005 | Sati et al. | 600/426 |
| 2005/0216305 A1 | 9/2005 | Funderud | 705/2 |
| 2005/0226374 A1 | 10/2005 | Lang et al. | 378/54 |
| 2005/0234461 A1 | 10/2005 | Burdulis, Jr. et al. | 606/79 |
| 2005/0267584 A1 | 12/2005 | Burdulis et al. | 623/20.19 |
| 2005/0278034 A1 | 12/2005 | Johnson et al. | 623/20.15 |
| 2006/0069318 A1 | 3/2006 | Keaveny et al. | 600/300 |
| 2006/0111722 A1 | 5/2006 | Bouadi | 606/79 |
| 2006/0111726 A1 | 5/2006 | Felt et al. | 606/86 |
| 2006/0149374 A1 | 7/2006 | Winslow et al. | 623/17.11 |
| 2006/0210017 A1 | 9/2006 | Lang | 378/54 |
| 2006/0210018 A1 | 9/2006 | Lang | 378/54 |
| 2006/0265078 A1 | 11/2006 | McMinn | 623/20.14 |
| 2007/0015995 A1 | 1/2007 | Lang et al. | 600/407 |
| 2007/0047794 A1 | 3/2007 | Lang et al. | 378/132 |
| 2007/0067032 A1 | 3/2007 | Felt et al. | 623/14.12 |
| 2007/0083266 A1 | 4/2007 | Lang | 623/17.11 |
| 2007/0100462 A1 | 5/2007 | Lang et al. | 623/20.29 |
| 2007/0118055 A1 | 5/2007 | McCombs | 600/587 |
| 2007/0118222 A1 | 5/2007 | Lang | 623/17.12 |
| 2007/0118243 A1 | 5/2007 | Schroeder et al. | 700/118 |
| 2007/0156171 A1 | 7/2007 | Lang et al. | 606/205 |
| 2007/0190108 A1 | 8/2007 | Datta et al. | 424/423 |
| 2007/0198022 A1 | 8/2007 | Lang et al. | 606/88 |
| 2007/0203430 A1 | 8/2007 | Lang et al. | 600/587 |
| 2007/0233156 A1 | 10/2007 | Metzger | 606/130 |
| 2007/0233269 A1 | 10/2007 | Steines et al. | 623/20.21 |
| 2007/0250169 A1 | 10/2007 | Lang | 623/17.12 |
| 2007/0255288 A1 | 11/2007 | Mahfouz et al. | 606/102 |
| 2007/0274444 A1 | 11/2007 | Lang | 378/54 |
| 2007/0276224 A1 | 11/2007 | Lang et al. | 600/410 |
| 2007/0276501 A1 | 11/2007 | Betz et al. | 623/17.16 |
| 2008/0009950 A1 | 1/2008 | Richardson | 623/20.29 |
| 2008/0015433 A1 | 1/2008 | Alexander et al. | 600/427 |
| 2008/0025463 A1 | 1/2008 | Lang | 378/54 |
| 2008/0031412 A1 | 2/2008 | Lang et al. | 378/54 |
| 2008/0058613 A1 | 3/2008 | Lang et al. | 600/300 |
| 2008/0058945 A1 | 3/2008 | Hajaj et al. | 623/20.14 |
| 2008/0119940 A1 | 5/2008 | Otto et al. | 623/20.31 |
| 2008/0147072 A1 | 6/2008 | Park et al. | 606/87 |
| 2008/0170659 A1 | 7/2008 | Lang et al. | 378/56 |
| 2008/0172125 A1 | 7/2008 | Ek | 623/14.12 |
| 2008/0195108 A1 | 8/2008 | Bhatnagar et al. | 606/87 |
| 2008/0195216 A1 | 8/2008 | Philipp | 623/18.11 |
| 2008/0215059 A1 | 9/2008 | Carignan et al. | 606/96 |
| 2008/0219412 A1 | 9/2008 | Lang | 378/207 |
| 2008/0243127 A1 | 10/2008 | Lang et al. | 606/87 |
| 2008/0262624 A1 | 10/2008 | White et al. | 623/20.32 |
| 2008/0275452 A1 | 11/2008 | Lang et al. | 606/88 |
| 2008/0281328 A1 | 11/2008 | Lang et al. | 606/87 |

(56) References Cited

U.S. PATENT DOCUMENTS

| | | | | |
|---|---|---|---|---|
| 2008/0281329 A1 | 11/2008 | Fitz et al. | | 623/17.16 |
| 2008/0281426 A1 | 11/2008 | Fitz et al. | | 623/17.16 |
| 2008/0319448 A1 | 12/2008 | Lavallee et al. | | 606/102 |
| 2009/0076371 A1 | 3/2009 | Lang et al. | | 600/407 |
| 2009/0076508 A1* | 3/2009 | Weinans et al. | | 606/62 |
| 2009/0118830 A1* | 5/2009 | Fell | | 623/14.12 |
| 2009/0131941 A1 | 5/2009 | Park et al. | | 606/87 |
| 2009/0228111 A1 | 9/2009 | Otto | | 623/20.19 |
| 2009/0276045 A1 | 11/2009 | Lang | | 623/14.12 |
| 2009/0306676 A1 | 12/2009 | Lang et al. | | 606/102 |
| 2009/0312805 A1 | 12/2009 | Lang et al. | | 606/86 R |
| 2009/0326666 A1 | 12/2009 | Wyss et al. | | 623/20.39 |
| 2010/0054572 A1 | 3/2010 | Tsougarakis et al. | | 382/131 |
| 2010/0274534 A1 | 10/2010 | Steines et al. | | 703/1 |
| 2010/0303313 A1 | 12/2010 | Lang et al. | | 382/128 |
| 2010/0303317 A1 | 12/2010 | Tsougarakis et al. | | 382/128 |
| 2010/0303324 A1 | 12/2010 | Lang et al. | | 382/131 |
| 2010/0305708 A1 | 12/2010 | Lang et al. | | 623/20.18 |
| 2010/0305907 A1 | 12/2010 | Fitz et al. | | 703/1 |
| 2010/0329530 A1 | 12/2010 | Lang et al. | | 382/131 |
| 2010/0331991 A1 | 12/2010 | Wilkinson et al. | | 623/20.32 |
| 2011/0029091 A1 | 2/2011 | Bojarski et al. | | 623/20.32 |
| 2011/0029093 A1 | 2/2011 | Bojarski et al. | | 623/20.35 |
| 2011/0066245 A1 | 3/2011 | Lang et al. | | 623/18.11 |
| 2011/0071645 A1 | 3/2011 | Bojarski et al. | | 623/20.35 |
| 2011/0071802 A1 | 3/2011 | Bojarski et al. | | 703/1 |
| 2011/0087332 A1 | 4/2011 | Bojarski et al. | | 623/20.32 |
| 2011/0125009 A1 | 5/2011 | Lang et al. | | 600/425 |
| 2011/0144760 A1 | 6/2011 | Wong et al. | | 623/20.14 |
| 2011/0266265 A1 | 11/2011 | Lang | | 219/121.72 |
| 2011/0295378 A1 | 12/2011 | Bojarski et al. | | 623/20.35 |
| 2012/0093377 A1 | 4/2012 | Tsougarakis et al. | | 382/128 |
| 2012/0191205 A1 | 7/2012 | Bojarski et al. | | 623/20.32 |
| 2012/0191420 A1 | 7/2012 | Bojarski et al. | | 703/1 |
| 2012/0197408 A1 | 8/2012 | Lang et al. | | 623/18.11 |
| 2012/0201440 A1 | 8/2012 | Steines et al. | | 382/131 |
| 2012/0209394 A1 | 8/2012 | Bojarski et al. | | 623/20.32 |
| 2012/0232669 A1 | 9/2012 | Bojarski et al. | | 623/20.3 |
| 2012/0232670 A1 | 9/2012 | Bojarski et al. | | 623/20.35 |
| 2012/0232671 A1 | 9/2012 | Bojarski et al. | | 623/20.35 |
| 2013/0006598 A1 | 1/2013 | Alexander et al. | | 703/11 |
| 2013/0071828 A1 | 3/2013 | Lang et al. | | 434/274 |
| 2013/0079781 A1 | 3/2013 | Fitz et al. | | 606/80 |
| 2013/0079876 A1 | 3/2013 | Fitz et al. | | 623/14.12 |
| 2013/0081247 A1 | 4/2013 | Fitz et al. | | 29/407.09 |
| 2013/0103363 A1 | 4/2013 | Lang et al. | | 703/1 |
| 2013/0110471 A1 | 5/2013 | Lang et al. | | 703/1 |

FOREIGN PATENT DOCUMENTS

| | | | | |
|---|---|---|---|---|
| DE | 2306552 | 8/1974 | | A61F 1/00 |
| DE | 3516743 | 11/1986 | | A61F 2/36 |
| DE | 8909091 | 9/1989 | | A61F 2/35 |
| DE | 44 34 539 | 4/1996 | | A61F 2/38 |
| DE | 19803673 | 8/1999 | | A61L 27/54 |
| DE | 19926083 | 12/2000 | | A61L 27/54 |
| DE | 10135771 | 2/2003 | | A61B 17/70 |
| EP | 0528080 | 2/1993 | | A61F 2/30 |
| EP | 0600806 | 6/1994 | | A61L 25/00 |
| EP | 0672397 | 9/1995 | | A61F 2/38 |
| EP | 0 704 193 | 4/1996 | | A61F 2/30 |
| EP | 0626156 | 7/1997 | | A61F 2/38 |
| EP | 0613380 | 12/1999 | | A61L 27/00 |
| EP | 1074229 | 2/2001 | | A61F 2/38 |
| EP | 1077253 | 2/2001 | | C12N 5/00 |
| EP | 1120087 | 8/2001 | | A61B 17/06 |
| EP | 1129675 | 9/2001 | | A61F 2/30 |
| EP | 0732091 | 12/2001 | | A61F 2/38 |
| EP | 0896825 | 7/2002 | | A61L 27/00 |
| EP | 0814731 | 8/2002 | | A61F 2/30 |
| EP | 1234552 | 8/2002 | | A61F 2/00 |
| EP | 1234555 | 8/2002 | | A61F 2/30 |
| EP | 0809987 | 10/2002 | | A61F 2/38 |
| EP | 0833620 | 10/2002 | | A61K 9/22 |
| EP | 1327423 | 7/2003 | | A61F 2/38 |
| EP | 0530804 | 6/2004 | | A61L 25/00 |
| EP | 1437101 | 7/2004 | | A61F 2/08 |
| EP | 1070487 | 9/2005 | | A61F 2/08 |
| EP | 1886640 | 2/2008 | | A61B 19/00 |
| EP | 2324799 | 5/2011 | | A61F 2/38 |
| FR | 2589720 | 11/1985 | | A61F 2/38 |
| FR | 2740326 | 4/1997 | | A61F 2/38 |
| GB | 1451283 | 9/1976 | | A61F 1/24 |
| GB | 2291355 | 1/1996 | | A61F 2/38 |
| GB | 2304051 | 3/1997 | | A61F 2/38 |
| GB | 2348373 | 10/2000 | | A61F 2/38 |
| JP | 56-083343 | 7/1981 | | A61F 1/03 |
| JP | 61-247448 | 11/1986 | | A61F 2/30 |
| JP | 1-249049 | 10/1989 | | A61F 2/38 |
| JP | 05-184612 | 7/1993 | | A61F 2/30 |
| JP | 7-236648 | 9/1995 | | A61F 2/28 |
| JP | 8-173465 | 7/1996 | | A61F 2/38 |
| JP | 9-206322 | 8/1997 | | A61F 2/36 |
| JP | 11-19104 | 1/1999 | | A61F 2/28 |
| JP | 11-276510 | 10/1999 | | A61F 2/28 |
| JP | 2007-521881 | 8/2007 | | A61F 2/44 |
| WO | WO 87/02882 | 5/1987 | | A61F 2/38 |
| WO | WO 90/09769 | 9/1990 | | A61F 2/28 |
| WO | WO 93/04710 | 3/1993 | | A61L 25/00 |
| WO | WO 93/09819 | 5/1993 | | A61L 27/00 |
| WO | WO 93/25157 | 12/1993 | | A61B 17/56 |
| WO | WO 95/27450 | 10/1995 | | A61F 2/38 |
| WO | WO 95/28688 | 10/1995 | | G06T 15/00 |
| WO | WO 95/30390 | 11/1995 | | A61F 2/38 |
| WO | WO 95/32623 | 12/1995 | | A01N 1/02 |
| WO | WO 96/24302 | 8/1996 | | A61B 17/90 |
| WO | WO 97/25942 | 7/1997 | | A61F 2/32 |
| WO | WO 97/27885 | 8/1997 | | A61L 27/00 |
| WO | WO 97/38676 | 10/1997 | | A61K 9/10 |
| WO | WO 97/46665 | 12/1997 | | C12N 5/06 |
| WO | WO 98/08469 | 3/1998 | | A61F 2/30 |
| WO | WO 98/12994 | 4/1998 | | A61F 2/28 |
| WO | WO 98/20816 | 5/1998 | | A61F 2/38 |
| WO | WO 98/30617 | 7/1998 | | C08G 63/12 |
| WO | WO 98/52498 | 11/1998 | | A61F 2/28 |
| WO | WO 99/02654 | 1/1999 | | C12N 5/00 |
| WO | WO 99/08598 | 2/1999 | | A61B 8/00 |
| WO | WO 99/08728 | 2/1999 | | A61L 27/00 |
| WO | WO 99/42061 | 8/1999 | | A61F 2/38 |
| WO | WO 99/47186 | 9/1999 | | A61L 27/00 |
| WO | WO 99/51719 | 10/1999 | | C12M 3/00 |
| WO | WO 00/09179 | 2/2000 | | A61L 25/00 |
| WO | WO 00/15153 | 3/2000 | | A61F 2/38 |
| WO | WO 00/19911 | 4/2000 | | A61B 17/02 |
| WO | WO 00/35346 | 6/2000 | | A61B 5/11 |
| WO | WO 00/48550 | 8/2000 | | |
| WO | WO 00/59411 | 10/2000 | | A61F 2/38 |
| WO | WO 00/68749 | 11/2000 | | G05B 19/4099 |
| WO | WO 00/74554 | 12/2000 | | |
| WO | WO 00/74741 | 12/2000 | | A61L 27/00 |
| WO | WO 00/76428 | 12/2000 | | A61F 2/38 |
| WO | WO 01/10356 | 2/2001 | | A61F 2/46 |
| WO | WO 01/17463 | 3/2001 | | A61F 2/30 |
| WO | WO 01/19254 | 3/2001 | | A61B 17/00 |
| WO | WO 01/35968 | 5/2001 | | A61K 35/00 |
| WO | WO 01/45764 | 6/2001 | | A61L 27/36 |
| WO | WO 01/68800 | 9/2001 | | C12M 3/00 |
| WO | WO 01/70142 | 9/2001 | | A61F 2/38 |
| WO | WO 01/77988 | 10/2001 | | G06F 19/00 |
| WO | WO 01/82677 | 11/2001 | | |
| WO | WO 01/91672 | 12/2001 | | A61F 2/36 |
| WO | WO 02/02021 | 1/2002 | | A61B 17/56 |
| WO | WO 02/22013 | 3/2002 | | A61B 5/55 |
| WO | WO 02/22014 | 3/2002 | | A61B 5/55 |
| WO | WO 02/23483 | 3/2002 | | A61B 5/55 |
| WO | WO 02/34310 | 5/2002 | | A61L 31/04 |
| WO | WO 02/36147 | 5/2002 | | A61K 31/04 |
| WO | WO 02/37423 | 5/2002 | | G06T 17/00 |
| WO | WO 02/096268 | 12/2002 | | |
| WO | WO 03/007788 | 1/2003 | | |
| WO | WO 03/037192 | 5/2003 | | A61B 17/15 |
| WO | WO 03/047470 | 6/2003 | | A61F 2/34 |
| WO | WO 03/051210 | 6/2003 | | A61B 17/58 |

(56) References Cited

FOREIGN PATENT DOCUMENTS

| WO | WO 03/061522 | 7/2003 | |
|----|----|----|----|
| WO | WO 03/099106 | 12/2003 | |
| WO | WO 2004/006811 | 1/2004 | A61F 2/46 |
| WO | WO 2004/032806 | 4/2004 | A61F 2/30 |
| WO | WO 2004/043305 | 5/2004 | A61F 2/30 |
| WO | WO 2004/049981 | 6/2004 | A61F 2/46 |
| WO | WO 2004/051301 | 6/2004 | G01R 33/56 |
| WO | WO 2004/073550 | 9/2004 | |
| WO | WO 2005/016175 | 2/2005 | |
| WO | WO 2005/020850 | 3/2005 | |
| WO | WO 2005/051239 | 6/2005 | A61F 2/08 |
| WO | WO 2005/051240 | 6/2005 | A61F 2/08 |
| WO | WO 2005/067521 | 7/2005 | |
| WO | WO 2005/076974 | 8/2005 | |
| WO | WO 2006/058057 | 6/2006 | A61F 2/38 |
| WO | WO 2006/060795 | 6/2006 | A61B 17/17 |
| WO | WO 2006/065774 | 6/2006 | A61F 2/44 |
| WO | WO 2007/041375 | 4/2007 | A61F 2/38 |
| WO | WO 2007/062079 | 5/2007 | A61F 2/30 |
| WO | WO 2007/092841 | 8/2007 | A61B 17/15 |
| WO | WO 2007/109641 | 9/2007 | A61F 2/30 |
| WO | WO 2008/021494 | 2/2008 | G06F 19/00 |
| WO | WO 2008/055161 | 5/2008 | A61F 2/44 |
| WO | WO 2008/157412 | 12/2008 | A61B 17/17 |
| WO | WO 2009/140294 | 11/2009 | A61F 2/30 |
| WO | WO 2010/099231 | 9/2010 | A61B 2/38 |
| WO | WO 2010/099353 | 9/2010 | A61F 2/38 |
| WO | WO 2010/140036 | 12/2010 | A61F 2/38 |
| WO | WO 2010/151564 | 12/2010 | A61F 2/38 |
| WO | WO 2011/028624 | 3/2011 | A61F 2/38 |
| WO | WO 2011/056995 | 5/2011 | A61F 2/38 |
| WO | WO 2011/072235 | 6/2011 | A61F 2/38 |
| WO | WO 2012/112694 | 8/2012 | A61B 6/00 |
| WO | WO 2012/112702 | 8/2012 | A61F 2/30 |
| WO | WO 2013/020026 | 2/2013 | A61F 2/30 |
| WO | WO 2013/056036 | 4/2013 | A61F 2/38 |

OTHER PUBLICATIONS

Adam et al., "NMR tomography of the cartilage structures of the knee joint with 3-D volume image combined with a rapid optical-imaging computer," ROFO Fortschr. Geb. Rontgenstr. Nuklearmed., 150(1): 44-48 (1989) Abstract Only.

Adam et al., "MR Imaging of the Knee: Three-Dimensional Volume Imaging Combined with Fast Processing,"J. Compt. Asst. Tomogr., 13(6): 984-988 (1989).

Adams et al., "Quantitative Imaging of Osteoarthritis," Semin Arthritis Rheum, 20(6) Suppl. 2: 26-39 (Jun. 1991).

Ahmad et al., "Biomechanical and Topographic Considerations for Autologous Osteochondral Grafting in the Knee," Am J Sports Med, 29(2): 201-206 (Mar.-Apr. 2001).

Alexander, "Estimating the motion of bones from markers on the skin," University of Illinois at Chicago (Doctoral Dissertation) (1998).

Alexander et al., "Correcting for deformation in skin-based marker systems," Proceedings of the 3rd Annual Gait and Clinical Movement Analysis Meeting, San Diego, CA (1998).

Alexander et al., "Internal to external correspondence in the analysis of lower limb bone motion," Proceedings of the 1999 ASME Summer Bioengineering Conference, Big Sky, Montana (1999).

Alexander et al., "State estimation theory in human movement analysis," Proceedings of the ASME International Mechanical Engineering Congress (1998).

Alexander et al., "Optimization techniques for skin deformation correction," International Symposium on 3-D Human Movement Conference, Chattanooga, TN, (1998).

Alexander et al., "Dynamic Functional Imaging of the Musculoskeletal System," ASME Winter International Congress and Exposition, Nashville, TN (1999).

Allen et al., "Late degenerative changes after meniscectomy 5 factors affecting the knee after operations," J Bone Joint Surg 66B: 666-671 (1984).

Alley et al., "Ultrafast contrast-enhanced three dimensional MR Aagiography: State of the art," Radiographics 18: 273-285 (1998).

Andersson et al., "MacIntosh Arthroplasty in Rheumatoid Arthritis," Acta. Orthrop. Scand. 45(2):245-259 (1974).

Andriacchi, "Dynamics of knee Malalignment," Orthop Clin North Am 25: 395-403 (1994).

Andriacchi, et al., "A point cluster method for in vivo motion analysis: Applied to a study of knee kinematics," J. Biomech Eng 120(12): 743-749 (1998).

Andriacchi, et al., "Methods for evaluating the progression of Osterarthiritis," Journal of Rehabilitation Research and Development 37(2): 163-170 (2000).

Andriacchi et al., "Gait analysis as a tool to assess joint kinetics biomechanics of normal and pathological human articulating joints," Nijhoff, Series E 93: 83-102 (1985).

Andriacchi et al., "In vivo measurement of six-degrees-of-freedom knee movement during functional testing," Transactions of the Orthopedic Research Society 698 (1995).

Argenson et al., "Is There a Place for Patellofemoral Arthroplasty?," Clinical Orthopaedics and Related Research No. 321, pp. 162-167 (1995).

Aro et al., "Clinical Use of Bone Allografts," Ann Med 25:403-412 (1993).

Bashir, "Validation of Gadolinium-Enhanced MRI of FAF Measurement in Human Cartilage," Intl. Soc. Mag. Resonance Med. (1998).

Beaulieu et al., "Glenohumeral relationships during physiological shoulder motion and stress testing: Initial experience with open MRI and active Scan-25 plane registration," Radiology (1999).

Beaulieu et al., "Dynamic imaging of glenohumeral instability with open MRI," Int. Society for Magnetic Resonance in Medicine Sydney, Australia (1998).

Beckmann et al., "Noninvasive 3D MR Microscopy as Tool in Pharmacological Research: Application to a Model of Rheumatoid Arthritis," Magn Reson Imaging 13(7): 1013-1017 (1995).

Billet, Philippe, French Version—"Gliding Knee Prostheses—Analysis of Mechanical Failures", Thesis, Medical School of Marseilles, 1982, 64 pages.

Billet, Philippe, Translated Version—"Gliding Knee Prostheses—Analysis of Mechanical Failures", Thesis, Medical School of Marseilles, 1982, 93 pages.

Blazina et al., "Patellofemoral replacement: Utilizing a customized femoral groove replacement," 5(1)53-55 (1990).

Blum et al., "Knee Arthroplasty in Patients with Rheumatoid Arthritis," Ann. Rheum. Dis. 33 (1): 1-11 (1974).

Bobic, "Arthroscopic osteochondral autogaft transplantation in anterior cruciate ligament reconstruction: a preliminary clinical study," Knee Surg Sports Traumatol Arthrosc 3(4): 262-264 (1996).

Boe et al., "Arthroscopic partial meniscectomy in patients aged over 50," J. Bone Joint Surg 68B: 707 (1986).

Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).

Borthakur et al., "In Vivo Triple Quantum Filtered Sodium MRI of Human Articular Cartilage," Proc. Intl. Soc. Mag. Resonance Med., 7:549 (1999).

Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).

Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).

Bregler et al., "Recovering non-rigid 3D shape from image streams," Proc. IEEE Conference on Computer Vision and Pattern Recognition (Jun. 2000).

Brett et al., "Quantitative Analysis of Biomedical Images," Univ. of Manchester, Zeneca Pharmaceuticals, IBM UK, http://www.wiau.man.ac.uk/~ads/imv (1998).

Brittberg et al., "A critical analysis of cartilage repair," Acta Orthop Scand 68(2): 186-191 (1997).

(56) References Cited

OTHER PUBLICATIONS

Brittberg et al., "Treatment of deep cartilage defects in the knee with autologous chrondrocyte transplantation," N Engl J Med 331(14): 889-895 (1994).
Broderick et al., "Severity of articular cartilage abnormality in patients with osteoarthritis: evaluation with fast spin-echo MR vs. arthroscopy," AJR 162: 99-103 (1994).
Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).
Burgkart et al., "Magnetic Resonance Imaging-Based Assessment of Cartilage Loss in Severe Osteoarthritis," Arth Rheum; 44(9): 2072-2077 (Sep. 2001).
Butterworth et al., "A T1O2 Dielectric-Filled Toroidal Resonator," Depts of Biomedical Engineering, Medicine, Neurology, & Center for Nuclear Imaging Research, U. of Alabama at Birmingham, USA, 1 Page (1999).
Butts et al., "Real-Time MR imaging of joint motion on an open MR imaging scanner," Radiological Society of North America, 83rd Scientific Assembly and Annual Meeting, Chicago, IL (1997).
Cameron, et al., "Review of a Failed Knee Replacement and Some Observations on the Design of a Knee Resurfacing Prosthesis," Arch. Orthop Trauma Surg. 97(2):87-89 (1980).
CAOS, "MIS meets CAOS Spring 2005 Symposium Schedule", *CAOS Spring 2005 Symposium*, pp. 1-9, May 19, 2005.
Carano et al., "Estimation of Erosive Changes in Rheumatoid Arthritis by Temporal Multispectral Analysis," Proc. Intl. Soc. Mag. Resonance Med., 7:408 (1999).
Carr et al., "Surface Interpolation with Radial Basis Functions for Medical Imaging," IEEE Transactions on Medical Imaging, IEEE, Inc. New York, vol. 16, pp. 96-107 (Feb. 1997).
Castriota-Scanderbeg et al., "Precision of Sonographic Measurement of Articular Cartilage: Inter-and Intraobserver Analysis," Skeletal Radiol 25: 545-549 (1996).
Chan et al., "Osteoarthritis of the Knee: Comparison of Radiography, CT and MR Imaging to Asses Extent and Severity," AJR Am J Roentgenol 157(4): 799-806 (1991).
Chelule et al., "Patient-Specific Template to Preserve Bone Stock in Total Knee Replacement: Preliminary Results", *15th Annual ISTA Symposium*, Sep. 2002, 1 page.
Clarke et al., "Human Hip Joint Geometry and Hemiarthroplasty Selection," The Hip. C.V. Mosby, St. Louis 63-89 (1975).
Clary et al., "Experience with the MacIntosh Knee Prosthesis," South Med. J. 65(3):265-272 (1972).
Cohen et al., "Knee cartilage topography, thickness, and contact areas from MRI: in-vitro calibration and in-vivo measurements," Osteoarthritis and Cartilage 7: 95-109 (1999).
Conaty, et al., "Surgery of the Hip and Knee in Patients with Rheumatoid Arthritis," J. Bone Joint Surg. Am. 55(2):301-314 (1973).
Creamer et al., "Quantitative Magnetic Resonance Imaging of the Knee: A Method of Measuring Response to Intra-Articular Treatments," Ann Rheum Dis. 378-381 (1997).
Daniel et al., "Breast cancer-gadolinium-enhanced MR imaging with a 0.5T open imager and three-point Dixon technique," Radiology 207(1): 183-190 (1998).
Dardzinski et al., "Entropy Mapping of Articular Cartilage", ISMRM Seventh Scientific Meeting, Philadelphia, PA (1999) T. 41, V. II.
Dardzinski et al., "T1-T2 Comparison in Adult Articular Cartilage," ISMRM Seventh Scientific Meeting, Philadelphia, PA (May 22-28, 1999).
DeWinter et al., "The Richards Type II Patellofemoral Arthroplasty", Acta Orthop Scand 2001; 72 (5): 487-490.
Disler, "Fat-suppressed three-dimensional spoiled gradient-recalled MR imaging: assessment of articular and physeal hyaline cartilage," AJR 169: 1117-1123 (1997).
Disler et al., "Fat-suppressed three-dimensional spoiled gradient-echo MR imaging of hyaline cartilage defects in the knee: comparison with standard MR imaging and arthroscopy," AJR 167: 127-132 (1996).
Disler et al., "Detection of knee hyaline cartilage defects using fat-suppressed three-dimensional spoiled gradient-echo MR imaging: comparison with standard MR imaging and correlation with arthroscopy," AJR 165: 377-382 (1995).
Doherty et al., Osteoarthritis, Oxford Textbook of Theumatology, Oxford University Press 959-983 (1993).
Dougados et al., "Longitudinal radiologic evaluation of osteoarthritis of the knee," J Theumatol 19: 378-384 (1992).
Du et al., "Vessel enhancement filtering in three-dimensional MR angiography," J. Magn Res Imaging 5: 151-157 (1995).
Du et al., "Reduction of partial-volume artifacts with zero filled interpolation in three-dimensional MR Angiography," J Magn Res Imaging 4: 733-741 (1994).
Dufour et al., "A Technique for the Dynamical Evaluation of the Acromiohumeral Distance of the Shoulder in the Seated Position under Open-field MRI," Proc. Intl. Soc. Mag. Resonance Med., 7:406 (1999).
Dumoulin et al., "Real-time position monitoring of invasive devises using magnetic resonance," Magn Reson Med 29: 411-5 (1993).
Dupuy et al., "Quantification of Articular Cartilage in the Knee with Three-Dimensional MR Imaging," Acad Radiol 3: 919-924 (1996).
Eckstein et al., "Determination of Knee Joint Cartilage Thickness Using Three-Dimensional Magnetic Resonance Chondro-Crassometry (3D MR-CCM)," Magn. Reson. Med. 36(2):256-265, (1996).
Eckstein et al., "Effect of Gradient and Section Orientation on Quantitative Analyses of Knee Joint Cartilage," Journal of Magnetic Resonance Imaging 11: 161-167 (2000).
Eckstein et al., "Effect of Physical Exercise on Cartilage Volume and Thickness In Vivo: An MR Imaging Study," Radiology 207: 243-248 (1998).
Eckstein et al., "Functional Analysis of Articular Cartilage Deformation, Recovery, and Fluid Flow Following Dynamic Exercise In Vivo," Anatomy and Embryology 200: 419-424 (1999).
Eckstein et al., "In Vivo Reproducibility of Three-Dimensional Cartilage Volume and Thickness Measurements With MR Imaging", AJR 170(3): 593-597 (1998).
Eckstein et al., "New Quantitative Approaches With 3-D MRI: Cartilage Morphology, Function and Degeneration", Medical Imaging International, Nov.-Dec. 1998.
Eckstein et al., "Side Differences of Knee Joint Cartilage Volume, Thickness, and Surface Area, and Correlation With Lower Limb Dominance—An MRI-Based Study," Osteoarthritis and Cartilage 10: 914-921 (2002).
Eckstein et al., Accuracy of Cartilage Volume and Thickness Measurements with Magnetic Resonance Imaging, Clin. Orthop. 1998; 352: 137-148 T. 60 V. II.
Eckstein et al., "Magnetic Resonance Chondro-Crassometry (MR CCM): A Method for Accurate Determination of Articular Cartilage Thickness?" Magn. Reson. Med. 35: 89-96 (1996).
Eckstein et al., "The Influence of Geometry on the Stress Distribution in Joints—A Finite Element Analysis," Anat Embryol, 189: 545-552 (1994).
Eckstein et al., "The Morphology of Articular Cartilage Assessed by Magnetic Resonance Imaging: Reproducibility and Anatomical Correlation," Sur. Radiol Anat 16: 429-438 (1994).
Elting et al., "Unilateral frame distraction: proximal tibial valgus osteotomy for medial gonarthritis," Contemp Orthrop 27(6): 522-524 (1993).
Faber et al., "Gender Differences in Knee Joint Cartilage Thickness, Volume and Articular Surface Areas: Assessment With Quantitative Three-Dimensional MR Imaging," Skeletal Radiology 30 (3): 144-150 (2001).
Faber et al., "Quantitative Changes of Articular Cartilage Microstructure During Compression of an Intact Joint," Proc. Intl. Soc. Mag. Resonance Med., 7:547 (1999).
Falcao et al., "User-steered image segmentation paradigms. Live wire and live lane," Graphical Models and Image Processing 60: 233-260 (1998).
Felson et al., "Weight Loss Reduces the risk for symptomatic knee osteoarthritis in women: the Framingham study," Ann Intern Med 116: 535-539 (1992).

(56) References Cited

OTHER PUBLICATIONS

Gandy et al., "One-Year Longitudinal Study of Femoral Cartilage Lesions in Knee Arthritis," Proc. Intl. Soc. Mag. Resonance Med., 7:1032 (1999).
Garrett, "Osteochondral allografts for reconstruction of articular defects of the knee," Instr Course Lect 47: 517-522 (1998).
Gerscovich, "A Radiologist's Guide to the Imaging in the Diagnosis and Treatment of Developmental Dysplasia of the Hip," Skeletal Radiol 26: 447-456 (1997).
Ghelman et al., "Kinematics of the Knee After Prosthetic Replacements", Clin. Orthop. May 1975: (108): 149-157.
Ghosh et al., "Watershed Segmentation of High Resolution Articular Cartilage Images for Assessment of Osteoarthritis," International Society for Magnetic Resonance in Medicine, Philadelphia, (1999).
Glaser et al., "Optimization and Validation of a Rapid Highresolution T1-W 3-D Flash Waterexcitation MR Sequence for the Quantitative Assessment of Articular Cartilage Volume and Thickness," Magnetic Resonance Imaging 19: 177-185 (2001).
Goodwin et al., "MR Imaging of Articular Cartilage: Striations in the Radial Layer Reflect the Fibrous Structure of Cartilage," Proc. Intl. Soc. Mag. Resonance Med., 7:546 (1999).
Gouraud, "Continuous shading of curved surfaces," IEEE Trans on Computers C-20(6) (1971).
Graichen et al., "Three-Dimensional Analysis of the Width of the Subacromial Space in Healthy Subjects and Patients With Impingement Syndrome," American Journal of Roentgenology 172: 1081-1086 (1999).
Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).
Hafez et al., "Computer-assisted Total Knee Arthroplasty Using Patient-specific Templating," *Clinical Orthopaedics and Related Research*, No. 444, pp. 184-192 (Mar. 2006).
Hall et al., "Quantitative MRI for Clinical Drug Trials of Joint Diseases; Virtual Biopsy of Articular Cartilage" NIH-FDA Conf. on Biomarkers and Surrogate Endpoints: Advancing Clinical Research and Applications (1998).
Hardy et al., "Measuring the Thickness of Articular Cartilage From MR Images," J. Magnetic Resonance Imaging 13: 120-126 (2001).
Hardy et al., "The Influence of the Resolution and Contrast on Measuring the Articular Cartilage Volume In Magnetic Resonance Images" Magn Reson Imaging. 18(8): 965-972 (Oct. 2000).
Hargreaves et al., "MR Imaging of Articular Cartilage Using Driven Equilibrium," Magnetic Resonance in Medicine 42(4): 695-703 (Oct. 1999).
Hargreaves et al., "Technical considerations for DEFT imaging," International Society for Magnetic Resonance in Medicine, Sydney, Australia (Apr. 17-24, 1998).
Hargreaves et al., "Imaging of articular cartilage using driven equilibrium," International Society for Magnetic Resonance in Medicine, Sydney, Australia (Apr. 17-24, 1998).
Hastings et al., "Double Hemiarthroplasty of the Knee in Rheumatoid Arthritis," A Survey of Fifty Consecutive Cases, J. Bone Joint Surg. Br. 55(1):112-118 (1973).
Haubner M, et al., "A Non-Invasive Technique for 3-Dimensional Assessment of Articular Cartilage Thickness Based on MRI Part @: Validation Using CT Arthrography," Magn Reson Imaging; 15(7): 805-813 (1997).
Haut et al., "A High Accuracy Three-Dimensional Coordinate Digitizing System for Reconstructing the Geometry of Diarthrodial Joints," J. Biomechanics 31: 571-577 (1998).
Hayes et al., "Evaluation of Articular Cartilage: Radiographic and Cross-Sectional Imaging Techniques," Radiographics 12: 409-428 (1992).
Henderson et al., "Experience with the Use of the Macintosh Prosthesis in Knees of Patients with Pheumatoid Arthritis," South. Med. J. 62(11):1311-1315 (1969).
Henkelman, "Anisotropy of NMR Properties of Tissues", Magn Res Med. 32: 592-601 (1994).

Herberhold et al., "An MR-Based Technique for Quantifying the Deformation of Articular Cartilage During Mechanical Loading in an Intact Cadaver Joint," Magnetic Resonance in Medicine 39(5): 843-850 (1998).
Herberhold, "In Situ Measurement of Articular Cartilage Deformation in Intact Femorapatellar Joints Under Static Loading", Journal of biomechanics 32: 1287-1295 (1999).
Herrmann et al., "High Resolution Imaging of Normal and Osteoarthritic Cartilage with Optical Coherence Tomogrqaphy," J. Rheumatoil 26: 627-635 (1999).
High et al., "Early Macromolecular Collagen Changes in Articular Cartilage of Osteoarthritis (OA): An In Vivo MT-MRI and Histopathologic Study," Proc. Intl. Soc. Mag. Resonance Med., 7:550 (1999).
Hohe, "Surface Size, Curvature Analysis, and Assessment of Knee Joint Incongruity With MR Imaging in Vivo", Magnetic Resonance in Medicine, 47: 554-561 (2002).
Holdsworth et al., "Benefits of Articular Cartilage Imaging at 4 Tesla: An In Vivo Study of Normal Volunteers," Proc. Intl. Soc. Mag. Resonance Med., 7:1028 (1999).
Hughes et al., "Technical Note: A Technique for Measuring the Surface Area of Articular Cartilage in Acetabular Fractures," Br. J. Radiol; 67: 584-588 (1994).
Husmann et al., "Three-Dimensional Morphology of the Proximal Femur," J. Arthroplasty; 12(4): 444-450 (Jun. 1997).
Hyhlik-Durr et al., "Precision of Tibial Cartilage Morphometry with a coronal water-excitation MR sequence," European Radiology 10(2): 297-303 (2000).
Ihara H., "Double-Contrast CT Arthrography of the Cartilage of the Patellofemoral Joint," Clin. Orthop.; 198: 50-55 (Sep. 1985).
Iida et al., "Socket Location in Total Hip Replacement: Preoperative Computed Tomography and Computer Simulation" Acta Orthop Scand; 59(1): 1-5 (1998).
Irarrazabal et al., "Fast three-dimensional magnetic resonance imaging," Mag Res. Med. 33: 656-662 (1995).
Jessop et al., "Follow-up of the MacIntosh Arthroplasty of the Knee Joint," Rheumatol Phys. Med. 11(5):217-224 (1972).
Johnson et al., "The distribution of load across the knee. A comparison of static and dynamic measurements," J. Bone Joint Surg 62B: 346-349 (1980).
Johnson, "In vivo contact kinematics of the knee joint: Advancing the point cluster technique," Ph.D. Thesis, University of Minnesota (1999).
Johnson et al., "Development of a knee wear method based on prosthetic in vivo slip velocity," Transaction of the Orthopedic Research Society, 46th Annual Meeting (Mar. 2000).
Jonsson et al., "Precision of Hyaline Cartilage Thickness Measurements," Acta Radiol 1992; 33(3): 234-239 (1992).
Kaneuji et al., "Three Dimensional Morphological Analysis of the Proximal Femoral Canal, Using Computer-Aided Design System, in Japanese Patients with Osteoarthrosis of the Hip," J. Orthop Sci; 5(4): 361-368 (2000).
Karvonen et al., "Articular Cartilage Defects of the Knee: Correlation Between Magnetic Resonance Imaging and Gross Pathology," Ann Rheum Dis. 49: 672-675 (1990).
Kass et al., "Snakes: Active contour models.," Int J Comput Vision 1: 321-331 (1988).
Kates, et al., "Experiences of Arthroplasty of the Rheumatoid Knee Using MacIntosh Prostheses," Ann. Rheum. Dis. 28(3):328 (1969).
Kaufman et al., "Articular Cartilage Sodium content as a function of compression" Seventh Scientific Meeting of ISMRM, p. 1022, 1999 T. 105, V. III.
Kay et al., The MacIntosh Tibial Plateau Hemiprosthesis for the Rheumatoid Knee, J. Bone Joint Surg. Br. 54(2):256-262 (1972).
Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).
Klosterman et al., "T2 Measurements in Adult Patellar Cartilage at 1.5 and 3.0 Tesla," ISMRM Seventh Scientific Meeting, Philadelphia, PA, (May 22-28, 1999).

(56) References Cited

OTHER PUBLICATIONS

Knauss et al., "Self-Diffusion of Water in Cartilage and Cartilage Components as Studied by Pulsed Field Gradient NMR," Magnetic Resonance in Medicine 41:285-292 (1999).
Koh et al., "Visualization by Magnetic Resonance Imaging of Focal Cartilage Lesions in the Excised Mini-Pig Knee," J. Orthop. Res; 14(4): 554-561 (Jul. 1996).
Korhonen et al., "Importance of the Superficial Tissue Layer for the Indentation Stiffness of Articular Cartilage," Med. Eng. Phys; 24(2): 99-108 (Mar. 2002).
Korkala et al., "Autogenous Osteoperiosteal Grafts in the Reconstruction of Full-Thickness Joint Surface Defects," Int. Orthop.; 15(3): 233-237 (1991).
Kshirsagar et al., "Measurement of Localized Cartilage Volume and Thickness of Human Knee Joints by Computer Analysis of Three-Dimensional Magnetic Resonance Images," Invest Radiol. 33(5): 289-299 (May 1998).
Kwak et al., "Anatomy of Human Patellofemoral Joint Articular Cartilage: Surface Curvature Analysis," J. Orthop. Res.; 15: 468-472 (1997).
LaFortune et al., "Three dimensional kinematics of the human knee during walking," J. Biomechanics 25: 347-357 (1992).
Lam et al., "X-Ray Diagnosis: A Physician's Approach", Editor Lam, 1998, Springer-Verlag publishers, Title page and Index Only (ISBN 9813083247).
Lang et al., "Functional joint imaging: a new technique integrating MRI and biomotion studies," International Society for Magnetic Resonance in Medicine, Denver (Apr. 18-24, 2000).
Lang et al., Risk factors for progression of cartilage loss: a longitudinal MRI study. European Society of Musculoskeletal Radiology, 6th Annual Meeting, Edinburgh, Scotland (1999).
Lang et al., Cartilage imaging: comparison of driven equilibrium with gradient-echo, SPAR, and fast spin-echo sequences. International Society for Magnetic Resonance in Medicine, Sydney, Australia, (Apr. 17-24, 1998).
Ledingham et al., "Factors affecting radiographic progression of knee osteoarthritis," Ann Rheum Dis 54: 53-58 (1995).
Leenslag et al., "A Porous Composite for Reconstruction of Meniscus Lesions," Biological and Biomechanical Perform. of Biomaterials, Elsevier Science Publishers Amsterdam pp. 147-152 (1986).
Lefebvre et al., "Automatic Three-Dimensional Reconstruction and Characterization of Articular Cartilage from High-Resolution Ultrasound Acquisitions," Ultrasound Med. Biol.; 24(9): 1369-1381 (Nov. 1998).
Li et al., A Boundary Optimization Algorithm for Delineating Brain Objects from CT Scans: Nuclear Science Symposium and Medical Imaging Conference 1993 IEEE Conference Record, San Francisco, CA (1993).
Lin et al., "Three-Dimensional Characteristics of Cartilagenous and Bony Components of Dysplastic Hips in Children: Three-Dimensional Computed Tomography Quantitative Analysis," J. Pediatr. Orthop.; 17: 152-157 (1997).
Lorensen et al., "Marching cubes: a high resolution 3d surface construction algorithm," Comput Graph 21: 163-169 (1987).
Losch et al., "A non-invasive technique for 3-dimensional assessment of articular cartilage thickness based on MRI part 1: development of a computational method," Magn Res Imaging 15(7): 795-804 (1997).
Lu et al., "Bone position estimation from skin marker co-ordinates using globals optimization with joint constraints," J Biomechanics 32: 129-134 (1999).
Lu et al., "In vitro degradation of porous poly(L-lactic acid) foams", Biomaterials, 21(15):1595-1605, Aug. 2000.
Lucchetti et al., "Skin movement artifact assessment and compensation in the estimation of knee-joint kinematics," J Biomechanics 31: 977-984 (1998).
Lusse et al., "Measurement of Distribution of Water Content of Human Articular Cartilage Based on Transverse Relaxation Times: An In Vitro Study," Seventh Scientific Meeting of ISMRM, p. 1020 (1999).
Lynch et al., "Cartilage segmentation of 3D MRI scans of the osteoarthritic knee combining user knowledge and active contours," Proc. SPIE 3979 Medical Imaging, San Diego pp. 925-935 (Feb. 2000).
MacIntosh, "Arthroplasty of the Knee in Rheumatoid Arthritis," Proceedings and Reports of Councils and Assotions, J. Bone & Joint Surg., vol. 48B No. (1): 179 (Feb. 1966).
MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).
MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).
MacIntosh, "Hemiarthroplasty of the Knee Using a Space Occupying Prosthesis for Painful Varus and Valgus Deformities," J. Bone Joint Surg. Am. Dec. 1958:40-A:1431.
Maki et al., "SNR improvement in NMRr microscopy using DEFT," J Mag Res; pp. 482-492 (1988).
Marler et al., "Soft-Tissue Augmentation with Injectable Alginate and Syngeneic Fibroblasts", Plastic & Reconstructive Surgery, 105(6):2049-2058, May 2000.
Marshall et al., "Quantitation of Articular Cartilage Using Magnetic Resonance Imaging and Three-Dimensional Reconstruction," J. Orthop. Res.; 13: 814-823 (1995).
Matsen, III et al., "Robotic Assistance in Orthopaedic Surgery: A Proof of Principle Using Distal Femoral Arthroplasty", Clinical Ortho. and Related Research, 296:178-186 (1993).
Mattila et al., "Massive Osteoarticular Knee Allografts: Structural Changes Evaluated with CT," Radiology; 196: 657-660 (1995).
McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).
Merkle et al., "A Transceiver Coil Assembly for Hetero-Nuclear Investigations of Human Breast at 4T," Proc. Intl. Soc. Mag. Resonance Med., 7:170 (1999).
Meyer et al., "Simultaneous spatial and spectral selective excitation," Magn Res Med 15: 287-304 (1990).
Mills et al., "Magnetic Resonance Imaging of the Knee: Evaluation of Meniscal Disease," Curr. Opin. Radiol. 4(6): 77-82 (1992).
Milz et al., "The Thickness of the Subchondral Plate and Its Correlation with the thickness of the Uncalcified Articular Cartilage in the Human Patella," Anat. Embryol.; 192: 437-444 (1995).
Minas, "Chondrocyte Implantation in the Repair of Chondral Lesions of the Knee: Economics and Quality of Life", Am. J. Orthop. Nov. 1998; 27: 739-744.
Modest et al., "Optical Verification of a Technique for In Situ Ultrasonic Measurement of Articular Cartilage Thickness," J. Biomechanics 22(2): 171-176 (1989).
Mollica et al., "Surgical treatment of arthritic varus knee by tibial corticotomy and angular distraction with an external fixator," Ital J Orthrop Traumatol 18(1): 17-23 (1992).
Moussa, "Rotational Malalignment and Femoral Torsion in Osteoarthritic Knees with Patellofemoral Joint Imvolvement: A CT Scan Study," Clin. Orthop.; 304: 176-183 (Jul. 1994).
Mundinger et al., "Magnetic Resonance Tomography in the Diagnosis of Peripheral Joints," Schweiz Med. Wochenschr. 121(15): 517-527 (1991) (Abstract Only).
Myers et al., "Experimental Assessment by High Frequency Ultrasound of Articular Cartilage Thickness and Osteoarthritic Changes," J. Rheumatol; 22: 109-116 (1995).
Nelson et al., "Arthroplasty and Arthrodesis of the Knee Joint," Orthop. Clin. North Am. 2 (1): 245-64 (1971).
Nieminen et al., "T2 Indicates Incompletely the Biomechanical Status of Enzymatically Degraded Articular Cartilage of 9.4T," Proc. Intl. Soc. Mag. Resonance Med., 7:551 (1999).
Nishii et al., "Three Dimensional Evaluation of the Acetabular and Femoral Articular Cartilage in the Osteoarthritis of the Hip Joint," Proc. Intl. Soc. Mag. Resonance Med., 7:1030 (1999).
Nizard, "Role of tibial osteotomy in the treatment of medical femorotibial osteoarthritis," Rev Rhum Engl Ed 65(7-9): 443-446 (1998).

(56) References Cited

OTHER PUBLICATIONS

Noll et al., "Homodyne detection in magnetic resonance imaging," IEEE Trans Med Imag 10(2): 154-163 (1991).
Ogilvie-Harris et al., "Arthroscopic management of the degenerative knee," Arthroscopy 7: 151-157 (1991).
Parkkinen et al., "A Mechanical Apparatus With Microprocessor Controlled Stress Profile for Cyclic Compression of Cultured Articular Cartilage Explants," J. Biomech.; 22 (11-12): 1285-1290 (1989).
Pearle et al., "Use of an external MR-tracking coil for active scan plane registration during dynamic Musculoskeletal MR imaging in a vertically open MR unit," American Roentgen Ray Society, San Francisco, CA (1998).
Peterfy et al., "Quantification of the volume of articular cartilage in the carpophalangeal joints of the hand: accuracy and precision of three-dimensional MR imaging," AJR 165: 371-375 (1995).
Peterfy et al., "MR Imaging of the arthritic knee: improved discrimination of cartilage, synovium, and effusion with pulsed saturation transfer and fat-suppressed TI-weighted sequences," Radiology 191(2): 413-419 (1994).
Peterfy et al., "Quantification of articular cartilage in the knee with pulsed saturation transfer subtraction and fat-suppressed MR imaging: optimization and validation," Radiology 192(2): 485-491 (1994).
Peterfy et al., "Emerging Applications of Magnetic Resonance Imaging in the Evaluation of Articular Cartilage," Radiol Clin North Am.; 34(2): 195-213 (Mar. 1996).
Pilch et al., "Assessment of Cartilage Volume in the Femorotibial Joint With Magnetic Resonance Imaging and 3D Computer Reconstruction," J. Rheumatol. 21(12): 2307-2319 (1994).
Piplani et al., "Articular cartilage volume in the knee: semi-automated determination from three-dimensional reformations of MR images," Radiology 198: 855-859 (1996).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Potter et al., "Magnetic resonance imaging of articular cartilage in the knee: an evaluation with use of fast-spin-echo imaging," J Bone Joint Surg 80-A(9): 1276-1284 (1998).
Potter et al., "Sensitivity of Quantitative NMR Imaging to Matrix Composition in Engineered Cartilage Tissue" Proc. Intl. Soc. Mag. Resonance Med., 7:552 (1999).
Probst et al., "Technique for Measuring the Area of Canine Articular Surfaces," Am. J. Vet. Res. 48(4): 608-609 (1987).
Prodromos et al., "A relationship between gait and clinical changes following high tibial osteotomy," J Bone Joint Surg 67A: 1188-1194 (1985).
Radermacher et al., "Computer Assisted Orthopedic Surgery by Means of Individual Templates •Aspects and Analysis of Potential Applications •" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).

Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher, "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." in Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.
Radin et al., "Mechanical Determination of Osteoarthrosis," Sem Arthr Rheum 21(3): 12-21 (1991).
Radin et al., Characteristics of Joint Loading as it Applies to Osteoarthrosis in: Mow VC, Woo S.Y., Ratcliffe T., eds. Symposium on Biomechanics of Diathrodial Joints, vol. 2, New York, NY: Springer-Verlag, pp. 437-451 (1990).
Ranawat et al., "MacIntosh Hemiarthroplasty in Rheumatoid Knee," Acta Orthop Belg., 39 (1): 1-11 (1973).
Recht et al., "Accuracy of fat-suppressed three-dimensional spoiled gradient-echo FLASH MR imaging in the detection of patellofemoral articular cartilage abnormalities," Radiology 198: 209-212 (1996).
Recht et al., "MR imaging of articular cartilage: current status and future directions," AJR 163: 283-290 (1994).
Reiser et al., "Magnetic Resonance in Cartilaginous Lesions of the Knee Joint With Three-Dimensional Gradient-Echo Imaging," Skeletal Radiol. 17(7): 465-471, (1988).
Ritter et al., "Postoperative alignment of total knee replacement," Clin Orthop 299: 153-156 (1994).
Robarts Research Institute, Abstract #1028 (1999).
Robson et al., "A Combined Analysis and Magnetic Resonance Imaging Technique for Computerized Automatic Measurement of Cartilage Thickness in Distal Interphalangeal Joint," Magnetic Resonance Imaging 13(5): 709-718 (1995).
Rushfeldt et al., "Improved Techniques for Measuring In Vitro the Geometry and Pressure Distribution in the Human Acetabulum—1. Ultrasonic Measurement of Acetabular Surfaces, Sphericity and Cartilage Thickness," J. Biomech; 14(4): 253-260 (1981).
Saied, "Assessment of Articular Cartilage and Subchondral Bone: Subtle and Progressive Changes in Experimental Osteoarthritis Using 50 MHz Echography In Vitro", J. Bone Miner Res. 1997; 12(9): 1378-1386.
Saito et al., "New algorithms for Euclidean distance transformation of an—dimensional digitized picture with applications," Pattern Recognition 27(11): 1551-1565 (1994).
Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Schipplein et al., "Interaction between active and passive knee stabilizers during level walking," J Orthop Res 9: 113-119 (1991).

(56) References Cited

OTHER PUBLICATIONS

Schorn et al., "MacIntosh Arthroplasty in Rheumatoid Arthritis," Rheumatol Rehabil. Aug. 1978:17(3):155-163.

Schouten et al., "A 12 year follow up study in the general population on prognostic factors of cartilage loss in osteoarthritis of the knee," Ann Rheum Dis 51: 932-937 (1992).

Shapiro et al., "In-Vivo Evaluation of Human Cartilage Compression and Recovery using 1H and 23Na MRI," Proc. Intl. Soc. Mag. Resonance Med., 7:548 (1999).

Sharif et al., "Serum hyaluronic acid level as a predictor of disease progression in osteoarthritis of the knee," Arthritis Rheum 38: 760-767 (1995).

Sharma et al., "Knee adduction moment, serum hyaluronic acid level, and disease severity in medial tibiofemoral osteoarthritis," Arthritis and Rheumatism 41(7): 1233-40 (1998).

Shoup et al., "The driven equilibrium Fourier transform NMR technique: an experimental study," J Mag Res p. 298-310 (1972).

Sittek et al., "Assessment of Normal Patellar Cartilage Volume and Thickness Using MRI: an Analysis of Currently Available Pulse Sequences", Skeletal Radiol 1996; 25: 55-61.

Slemenda et al., "Lower extremity lean tissue mass strength predict increases in pain and in functional impairment in knee osteoarthritis," Arthritis Rheum 39(suppl): S212 (1996).

Slemenda et al., "Lower extremity strength, lean tissue mass and bone density in progression of knee osteoarthritis," Arthritis Rheum 39(suppl): S169 (1996).

Slone et al., "Body CT: A Practical Approach", Editor Slone, 1999 McGraw-Hill publishers, Title page and Table of Contents pgs. Only (ISBN 007058219).

Solloway et al., "The use of active shape models for making thickness measurements of articular cartilage from MR images," Mag Res Med 37: 943-952 (1997).

Soslowsky et al., "Articular Geometry of the Glenohumeral Joint," Clin. Orthop.; 285: 181-190 (Dec. 1992).

Spoor et al., "Rigid body motion calculated from spatial coordinates of markers," J. Biomechanics 13: 391-393 (1980).

Stammberger et al., "A Method for Quantifying Time Dependent Changes in MR Signal Intensity of Articular Cartilage As a Function of Tissue Deformation in Intact Joints" Medical Engineering & Physics 20: 741-749 (1998).

Stammberger et al., "A New Method for 3D Cartilage Thickness Measurement with MRI, Based on Euclidean Distance Transformation, and its Reproducibility in the Living," Proc. Intl. Soc. Mag. Resonance Med., 6:562 (1998).

Stammberger et al., "Elastic Registration of 3D Cartilage Surfaces From MR Image Data for Detecting Local Changes of the Cartilage Thickness," Magnetic Resonance in Medicine 44: 592-601 (2000).

Stammberger et al., "Determination of 3D cartilage thickness data from MR imaging: computational method and reproducibility in the living," Mag Res Med 41: 529-536 (1999).

Stammberger et al., "Interobserver to reproducibility of quantitative cartilage measurements: Comparison of B-spline snakes and manual segmentation," Mag Res Imaging 17: 1033-1042 (1999).

Stauffer et al., "The MacIntosh Prosthesis. Prospective Clinical and Gait Evaluation," Arch. Surg. 110(6):717-720 (1975).

Steines et al., Segmentation of osteoarthritic femoral cartilage using live wire, Proc. Intl. Soc. Mag. Resonance Med., 8:220 (2000).

Steines et al., "Segmentation of osteoarthritis femoral cartilage from MR images," CARS—Computer-Assisted Radiology and Surgery, pp. 578-583, San Francisco (2000).

Steines et al., "Measuring volume of articular cartilage defects in osteoarthritis using MRI," ACR 64th Annual Scientific Meeting, Philadelphia, (Oct. 2000).

Stevenson et al., "The fate of articular cartilage after transplantation of fresh and cryopreserved tissue-antigen-matched and mismatched osteochondral allografts in dogs," J. Bone Joint Surg 71(9): 1297-1307 (1989).

Stout et al., "X-Ray Structure Determination: A Practical Guide", 2$^{nd}$ Ed. Editors Stout and Jensen, 1989, John Wiley & Sons, Title page and Table of Contents pgs. Only (ISBN 0471607118).

Taha et al., "Modeling and Design of a Custom Made Cranium Implant for Large Skull Reconstruction Before a Tumor Removal", Phidias Newsletter No. 6, pp. 3, Jun. 6, 2001. Retrieved from the Internet: URL:http://www.materialise.com/medical/files/pdf.

Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.

Tebben et al., "Three-Dimensional Computerized Reconstruction. Illustration of Incremental Articular Cartilage Thinning," Invest. Radiol. 32(8): 475-484 (1997).

Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).

Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).

Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).

Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).

Tieschky et al., "Repeatability of patellar cartilage thickness patterns in the living, using a fat-suppressed magnetic resonance imaging sequence with short acquisition time and three-dimensional data processing," J. Orthop Res 15(6): 808-813 (1997).

Tomasi et al., "Shape and motion from image streams under orthography—a factorization method," Proc. Nat. Acad. Sci. 90(21): 9795-9802 (1993).

Tsai et al., "Application of a flexible loop-gap resonator for MR imaging of articular cartilage at 3.TO," International Society for Magnetic Resonance in Medicine, Denver (Apr. 24-28, 2000) 8:2127.

Tyler et al., "Detection and Monitoring of Progressive Degeneration of Osteoarthritic Cartilage by MRI," Acta Orthop Scand 1995; 66 Suppl. 266: 130-138 (1995).

Van Leersum et al., "Thickness of Patellofemoral Articular Cartilage as Measured on MR Imaging: Sequence Comparison of accuracy, reproducibility, and interobserver variation," Skeletal Radiol 1995; 24: 431-435 (1995).

Vandeberg et al., "Assessment of Knee Cartilage in Cadavers with Dual-Detector Sprial CT ARthrography and MR Imaging", Radiology, Feb. 2002: 222(2): 430-435 T. 195, V.V.

Van der Linden et al., "MR Imaging of Hyaline Cartilage at 0.5 T: A Quantitative and Qualitative in vitro Evaluation of Three Types of Sequences" pp. 297-305 (Jun. 1998).

Velyvis et al., "Evaluation of Articular Cartilage with Delayed Gd(DTPA)2-Enhanced MRI: Promise and Pitfalls," Proc. Intl. Soc. Mag. Resonance Med., 7:554 (1999).

Wang et al., "The influence of walking mechanics and time on the results of proximal tibial osteotomy," J. Bone Joint Surg 72A: 905-909 (1990).

Warfield et al., "Automatic Segmentation of MRI of the Knee," ISMRM Sixth Scientific Meeting and Exhibition p. 563, Sydney, Australia (Apr. 17-24, 1998).

Warfield et al., "Adaptive Template Moderated Spatially Varying Statistical Classification," Proc. First International Conference on Medical Image Computing and Computer Assisted, MICCAI, pp. 231-238 (1998).

Warfield et al., "Adaptive, Template Moderated Spatially Varying Statistical Classification," Medical Image Analysis 4(1): 43-55 (2000).

Waterton et al., "Diurnal variation in the femoral articular cartilage of the knee in young adult humans," Mag Res Med 43: 126-132 (2000).

Waterton et al., "Magnetic Resonance Methods for Measurement of Disease Progression in Rheumatoid Arthritis," Mag. Res. Imaging; 11: 1033-1038 (1993).

(56) References Cited

OTHER PUBLICATIONS

Watson et al., "MR Protocols for Imaging the Guinea Pig Knee," Mag. Res. Imaging 15(8): 957-970 (1997).
Wayne et al., "Measurement of Articular Cartilage Thickness in the Articulated Knee," ANN Biomed Eng.; 26(1): 96-102 (1998).
Wayne et al., "Finite Element Analyses of Repaired Articular Surfaces," Proc. Instn. Mech. Eng.; 205(3): 155-162 (1991).
Wiese et al., "Biomaterial properties and biocompatibility in cell culture of a novel self-inflating hydrogel tissue expander", J. Biomedical Materials Research Part A, 54(2):179-188, Nov. 2000.
Wolff et al., "Magnetization transfer contrast: MR imaging of the knee," Radiology 179: 623-628 (1991).
Wordsworth et al., "MacIntosh Arthroplasty for the Rheumatoid Knee: A 10-year Follow Up," Ann. Rheum. Dis. 44(11):738-741 (1985).
Worring et al., "Digital curvature estimation. CVGIP," Image Understanding 58(3): 366-382 (1993).
Yan, "Measuring changes in local volumetric bone density," new approaches to quantitative computed tomography, Ph.D. thesis, Dept. of Electrical Engineering, Stanford University (1998).
Yao et al., "Incidental magnetization transfer contrast in fast spin-echo imaging of cartilage," J. Magn Reson Imaging 6(1): 180-184 (1996).
Yao et al., "MR imaging of joints: analytic optimization of GRE techniques at 1.5T," AJR 158(2): 339-345 (1992).
Yasuda et al., "A 10 to 15 year follow up observation of high tibial osteotomy in medial compartment osteoarthritis," Clin Orthop 282: 186-195 (1992).
Yusof et al., "Preparation and characterization of chitin beads as a wound dressing precursor", J. Biomedical Materials Research Part A, 54(1):59-68, Oct. 2000.
Zimmer, Inc., "There's a New Addition to the Flex Family! The Zimmer® Unicompartmental Knee System", pp. 1-8 (2004).
International Searching Authority, International Search Report—International Application No. PCT/US02/16945, dated Mar. 26, 2003, 6 pages.
European Patent Office, Supplementary European Search Report—Application No. 03713907.8, dated Dec. 6, 2006, 3 pages.
European Patent Office, Supplementary Partial European Search Report—Application No. 02737254.9, dated Mar. 2, 2007, 5 pages.
International Searching Authority, International Search Report—International Application No. PCT/US03/38158, dated Feb. 23, 2005, 7 pages.
European Patent Office, European Search Report—Application No. EP 03790194, dated Jul. 13, 2006, 7 pages.
International Searching Authority, International Search Report—International Application No. PCT/US03/32123, dated Mar. 17, 2004, 7 pages.
International Searching Authority, International Search Report—International Application No. PCT/US03/36079, dated Apr. 15, 2004, 7 pages.
International Searching Authority, International Search Report—International Application No. PCT/US04/39714, dated May 13, 2005, together with the Written Opinion of the International Searching Authority, 8 pages.
International Searching Authority, International Search Report—International Application No. PCT/US2005/042421, dated May 18, 2006, together with the Written Opinion of the International Searching Authority, 7 pages.
European Patent Office, Supplementary European Search Report—Application No. 04812273.3, dated Oct. 8, 2007, 5 pages.
International Searching Authority, Invitation to Pay Additional Fees—International Application No. PCT/US2007/064349 dated Aug. 7, 2007, 8 pages.
International Searching Authority, International Search Report—International Application No. PCT/US2007/064349, dated Oct. 12, 2007, together with the Written Opinion of the International Searching Authority, 20 pages.
European Patent Office, Supplementary European Search Report—Application No. 04812273.3-2310, dated Dec. 10, 2007, 7 pages.
International Searching Authority, International Search Report—International Application No. PCT/US06/45131, dated Jul. 11, 2007, together with the Written Opinion of the International Searching Authority, 6 pages.
International Searching Authority, International Search Report—International Application No. PCT/US06/38212, dated Apr. 22, 2008, together with the Written Opinion of the International Searching Authority, 7 pages.
International Searching Authority, International Preliminary Report on Patentability—International Application No. PCT/US2006/045131, dated Jun. 5, 2008, together with the Written Opinion of the International Searching Authority, 6 pages.
International Searching Authority, International Search Report—International Application No. PCT/US2009/043656, dated Jul. 9, 2009, together with the Written Opinion of the International Searching Authority, 8 pages.
United States Patent and Trademark Office, Office Action dated Jul. 30, 2009, pertaining to U.S. Appl. No. 11/537,318, 56 pages.
Sunstein Kann Murphy & Timbers LLP, Request for Continued Examination and Response dated Aug. 27, 2009 pertaining to U.S. Appl. No. 10/752,438, 22 pages.
United States Patent and Trademark Office, Office Action dated Nov. 10, 2009 pertaining to U.S. Appl. No. 10/752,438, 8 pages.
Sunstein Kann Murphy & Timbers LLP, Request for Continued Examination and Response dated Jul. 27, 2009 pertaining to U.S. Appl. No. 10/997,407, 26 pages.
United States Patent and Trademark Office, Office Action dated Nov. 24, 2009 pertaining to U.S. Appl. No. 10/997,407, 14 pages.
United States Patent and Trademark Office, Office Action dated Jan. 9, 2009, pertaining to U.S. Appl. No. 10/764,010 (US Patent Publication No. US 2004/0167390), 11 pages.
Bromberg & Sunstein LLP, Response to Office Action dated Jan. 9, 2009, pertaining to U.S. Appl. No. 10/764,010 (US Patent Publication No. US 2004/0167390), 25 pages.
United States Patent and Trademark Office, Office Action dated Oct. 23, 2009, pertaining to U.S. Appl. No. 10/764,010 (US Patent Publication No. US 2004/0167390), 13 pages.
United States Patent and Trademark Office, Office Action dated Jul. 9, 2009, pertaining to U.S. Appl. No. 10/160,667, 5 pages.
Sunstein Kann Murphy & Timbers LLP, Amendment dated Jan. 11, 2010, pertaining to U.S. Appl. No. 10/160,667, 12 pages.
United States Patent and Trademark Office, Office Action dated Aug. 6, 2009, pertaining to U.S. Appl. No. 10/681,749, 6 pages.
Sunstein Kann Murphy & Timbers LLP, Response to Office Action dated Aug. 6, 2009, pertaining to U.S. Appl. No. 10/681,749, 18 pages.
United States Patent and Trademark Office, Office Action dated Nov. 25, 2008, pertaining to U.S. Appl. No. 10/681,750, 21 pages.
Sunstein Kann Murphy & Timbers LLP, Response to Office Action dated Nov. 25, 2008, pertaining to U.S. Appl. No. 10/681,750, 17 pages.
United States Patent and Trademark Office, Office Action dated Sep. 22, 2009, pertaining to U.S. Appl. No. 10/681,750, 21 pages.
European Patent Office, European Search Report—International Application No. PCT/US2006/045131 dated Mar. 3, 2010, 6 pages.
United States Patent and Trademark Office, Office Action dated Apr. 24, 2009, pertaining to U.S. Appl. No. 10/704,208, 23 pages.
Sunstein Kann Murphy & Timbers LLP, Request for Continued Examination and Response dated Oct. 26, 2009, pertaining to U.S. Appl. No. 10/704,208, 17 pages.
United States Patent and Trademark Office, Office Action dated Dec. 30, 2009, pertaining to U.S. Appl. No. 10/704,208, 10 pages.
International Searching Authority, International Search Report—International Application No. PCT/US2010/025459, dated Apr. 20, 2010, together with the Written Opinion of the International Searching Authority, 15 pages.
Bromberg & Sunstein LLP, Request for Continued Examination dated May 24, 2007, pertaining to U.S. Appl. No. 10/305,652, 21 pages.
United States Patent and Trademark Office, Office Action dated Aug. 13, 2007, pertaining to U.S. Appl. No. 10/305,652, 6 pages.
Bromberg & Sunstein LLP, Response to Office Action dated Aug. 13, 2007, pertaining to U.S. Appl. No. 10/305,652, 10 pages.

(56) References Cited

OTHER PUBLICATIONS

United States Patent and Trademark Office, Office Action dated Dec. 19, 2007, pertaining to U.S. Appl. No. 10/305,652, 6 pages.
Bromberg & Sunstein LLP, Response to Office Action dated Dec. 19, 2007, pertaining to U.S. Appl. No. 10/305,652, 17 pages.
Bromberg & Sunstein LLP, Supplemental Response dated May 2, 2008, pertaining to U.S. Appl. No. 10/305,652, 12 pages.
United States Patent and Trademark Office, Office Action dated Jul. 29, 2008, pertaining to U.S. Appl. No. 10/305,652, 10 pages.
Bromberg & Sunstein LLP, Amendment After Final Rejection dated Aug. 26, 2008, pertaining to U.S. Appl. No. 10/305,652, 17 pages.
United States Patent and Trademark Office, Office Action dated Aug. 4, 2009, pertaining to U.S. Appl. No. 10/704,325, 11 pages.
Sunstein Kann Murphy & Timbers LLP, Response to Office Action dated Aug. 4, 2009, pertaining to U.S. Appl. No. 10/704,325, 15 pages.
United States Patent and Trademark Office, Notice of Allowance dated May 17, 2010, pertaining to U.S. Appl. No. 10/704,325, 20 pages.
United States Patent and Trademark Office, Office Action dated Jul. 23, 2010, pertaining to U.S. Appl. No. 12/317,416, 7 pages.
United States Patent and Trademark Office, Office Action dated Apr. 26, 2010, pertaining to U.S. Appl. No. 10/160,667, 11 pages.
United States Patent and Trademark Office, Office Action dated Aug. 2, 2010, pertaining to U.S. Appl. No. 12/317,472, 7 pages.
United States Patent and Trademark Office, Office Action dated Aug. 5, 2010, pertaining to U.S. Appl. No. 10/997,407, 12 pages.
United States Patent and Trademark Office, Office Action dated May 26, 2010, pertaining to U.S. Appl. No. 11/602,713, 10 pages.
United States Patent and Trademark Office, Office Action dated Jun. 28, 2010, pertaining to U.S. Appl. No. 10/752,438, 9 pages.
United States Patent and Trademark Office, Office Action dated Mar. 4, 2010, pertaining to U.S. Appl. No. 11/688,340, 15 pages.
Sunstein Kann Murphy & Timbers LLP, Response to Office Action dated Jul. 30, 2009, pertaining to U.S. Appl. No. 11/537,318, 9 pages.
United States Patent and Trademark Office, Office Action dated Jun. 3, 2010, pertaining to U.S. Appl. No. 11/537,318, 10 pages.
International Searching Authority, International Search Report—International Application No. PCT/US2010/039587, dated Aug. 19, 2010, together with the Written Opinion of the International Searching Authority, 15 pages.
European Patent Office, Extended European Search Report—European Application No. 06815884.9-2310, dated Sep. 14, 2010, 7 pages.
United States Patent and Trademark Office, Office Action dated Sep. 15, 2010, pertaining to U.S. Appl. No. 10/704,208, 13 pages.
International Searching Authority, International Search Report—International Application No. PCT/US2010/025274, dated Sep. 20, 2010, together with the Written Opinion of the International Searching Authority, 18 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10/764,010, 21 pages.
United States Patent and Trademark Office, Notice of Allowance dated Dec. 16, 2010, pertaining to U.S. Appl. No. 10/764,010, 11 pages.
Sunstein Kann Murphy & Timbers LLP, Response to Office Action dated Aug. 2, 2010, pertaining to U.S. Appl. No. 12/317,472, 15 pages.
United States Patent and Trademark Office, Office Action dated Feb. 10, 2011, pertaining to U.S. Appl. No. 12/317,416, 10 pages.
International Searching Authority, International Search Report—International Application No. PCT/US2010/046868, dated Jan. 7, 2011, together with the Written Opinion of the International Searching Authority, 11 pages.
United States Patent and Trademark Office, Office Action dated Feb. 22, 2011, pertaining to U.S. Appl. No. 11/602,713, 10 pages.
United States Patent and Trademark Office, Office Action dated Feb. 24, 2011, pertaining to U.S. Appl. No. 12/317,472, 12 pages.
United States Patent and Trademark Office, Office Action dated Mar. 2, 2011, pertaining to U.S. Appl. No. 10/752,438, 8 pages.
European Patent Office, Extended European Search Report—European Application No. 10012404.9-2310, dated Apr. 1, 2011, 7 pages.
United States Patent and Trademark Office, Office Action dated Apr. 18, 2011, pertaining to U.S. Appl. No. 12/464,763, 13 pages.
United States Patent and Trademark Office, Notice of Allowance dated Aug. 5, 2011, pertaining to U.S. Appl. No. 10/764,010, 14 pages.
United States Patent and Trademark Office, Office Action dated Sep. 15, 2011, pertaining to U.S. Appl. No. 10/997,407, 13 pages.
United States Patent and Trademark Office, Office Action dated Dec. 6, 2010, pertaining to U.S. Appl. No. 12/853,599, 11 pages.
Sunstein Kann Murphy & Timbers LLP, Response to Office Action dated Dec. 6, 2010, pertaining to U.S. Appl. No. 12/853,599, 16 pages.
United States Patent and Trademark Office, Notice of Allowance dated Sep. 14, 2011, pertaining to U.S. Appl. No. 12/853,599, 9 pages.
International Searching Authority, International Search Report—International Application No. PCT/US2010/055483, dated Jul. 28, 2011, together with the Written Opinion of the International Searching Authority, 9 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Preliminary Amendment dated Aug. 12, 2011, pertaining to U.S. Appl. No. 13/017,886, 13 pages.
United States Patent and Trademark Office, Office Action dated Jun. 23, 2011 pertaining to U.S. Appl. No. 11/410,515, 13 pages.
International Searching Authority, International Search Report—International Application No. PCT/US2010/059910 dated Oct. 25, 2011, together with the Written Opinion of the International Searching Authority, 9 pages.

(56) References Cited

OTHER PUBLICATIONS

International Searching Authority, International Search Report—International Application No. PCT/US2012/025269 dated Aug. 31, 2012, together with the Written Opinion of the International Searching Authority, 14 pages.
International Searching Authority, International Search Report—International Application No. PCT/US2012/049472 dated Oct. 16, 2012, together with the Written Opinion of the International Searching Authority, 12 pages.
International Searching Authority, International Search Report—International Application No. PCT/US2012/050964 dated Oct. 22, 2012, together with the Written Opinion of the International Searching Authority, 13 pages.
European Patent Office, European Search Report—Application No. 12170854.9-1526 dated Oct. 9, 2012, 6 pages.
International Searching Authority, International Search Report—International Application No. PCT/US12/59936 dated Jan. 9, 2013, together with the Written Opinion of the International Searching Authority, 11 pages.
European Patent Office, Extended European Search Report—Application No. 10792589.3-2310 dated Feb. 7, 2013, 9 pages.
European Patent Office, European Search Report—Application No. 10192339.9-1257 dated Jan. 23, 2013, 5 pages.
European Patent Office, Extended European Search Report—Application No. 10746859.7-1654 dated Mar. 4, 2013, 7 pages.
European Patent Office, Extended European Search Report—Application No. 12192903.8-1654 dated Apr. 17, 2013, 8 pages.
International Searching Authority, International Search Report—International Application No. PCT/US2012/025280 dated Oct. 25, 2012, together with the Written Opinion of the International Searching Authority, 11 pages.

* cited by examiner

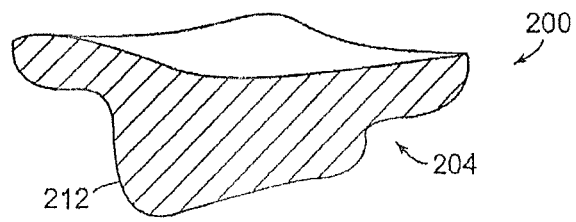
FIG. 2K
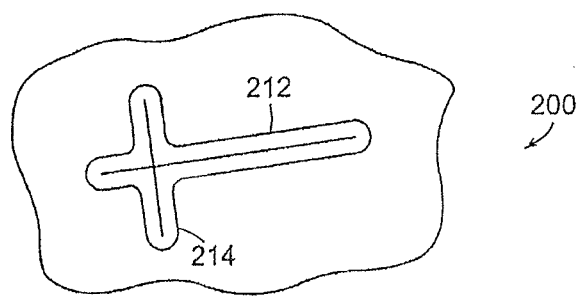
FIG. 2L
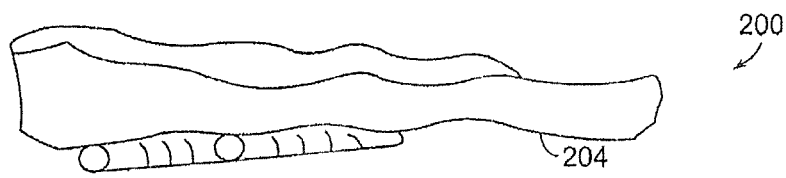
FIG. 2M
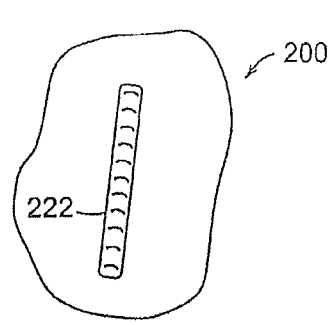 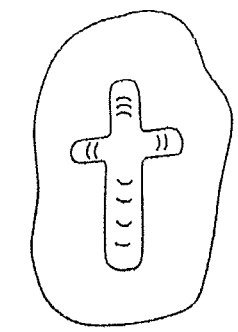
FIG. 2N 1    FIG. 2O 1

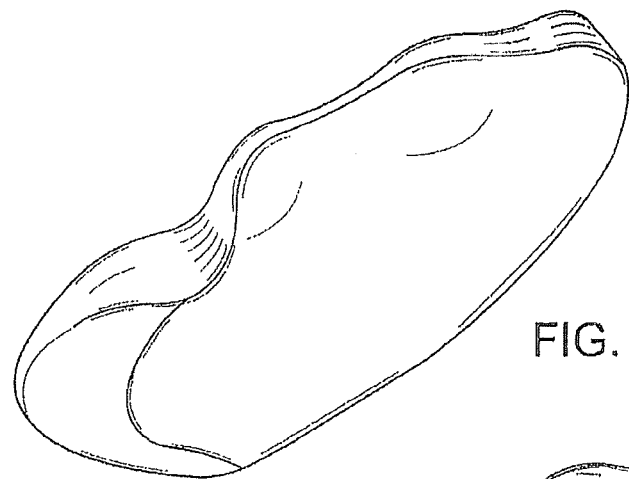
FIG. 2s-7
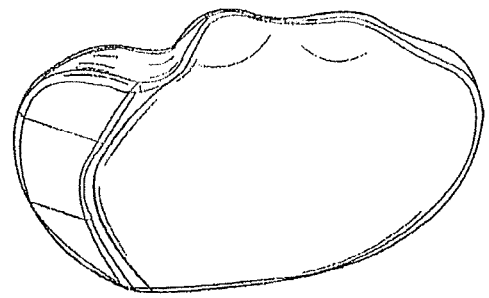
FIG. 2s-8
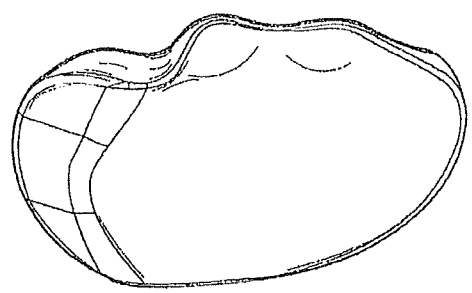
FIG. 2s-9
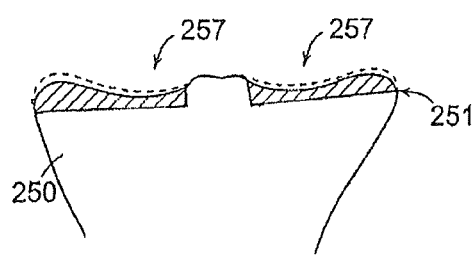
FIG. 2T(1)
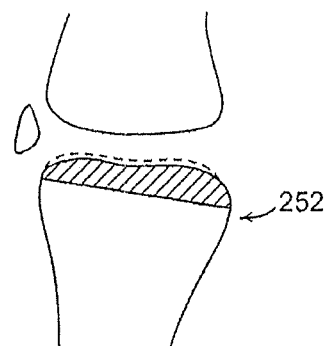
FIG. 2T(2)

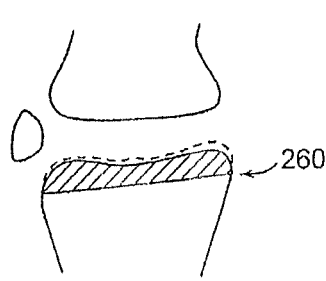
FIG. 2T(3)
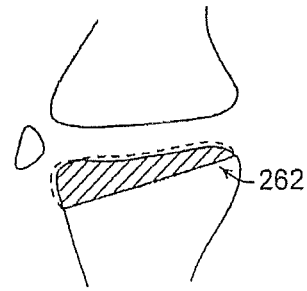
FIG. 2T(4)
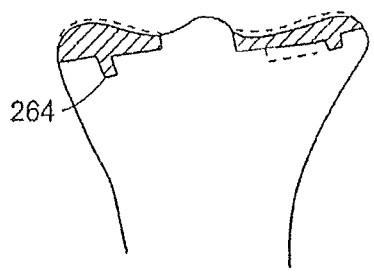
FIG. 2T(5)
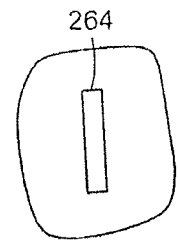
FIG. 2T(6)
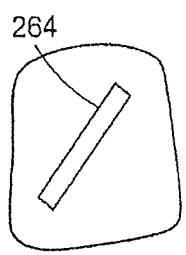 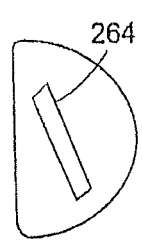
FIG. 2T(7)
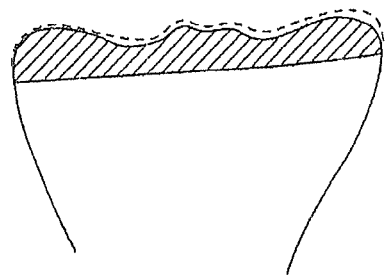
FIG. 2T(8)

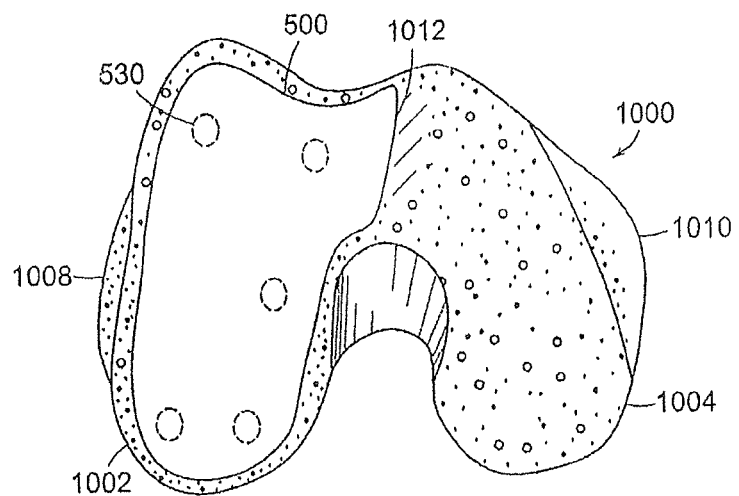
FIG. 5J
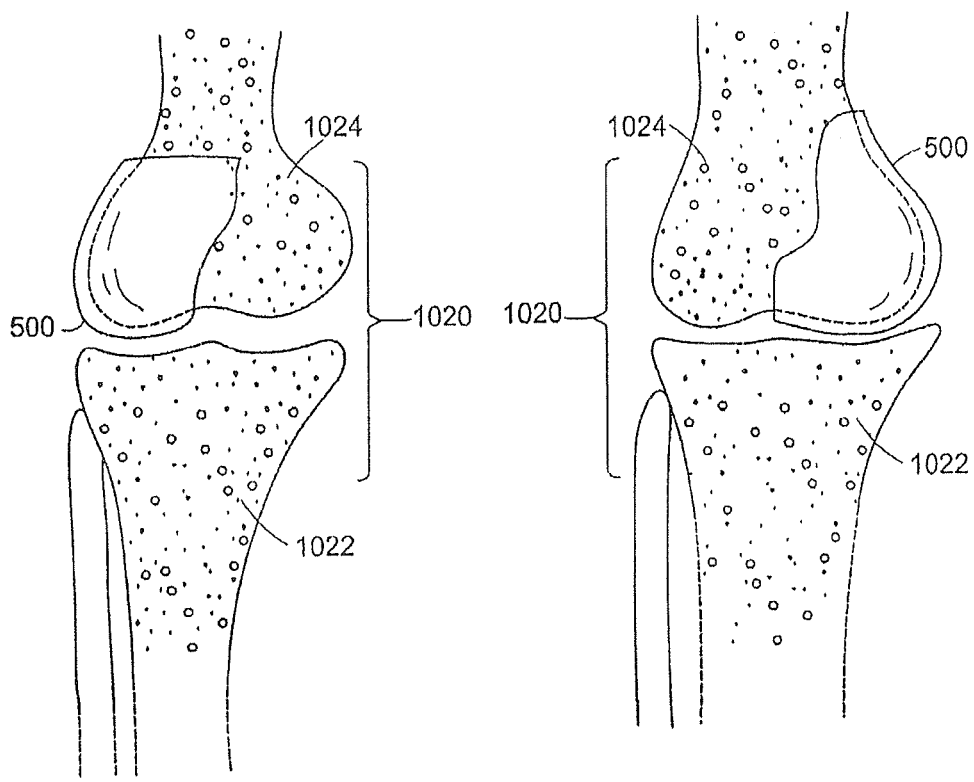
FIG. 5K
FIG. 5L

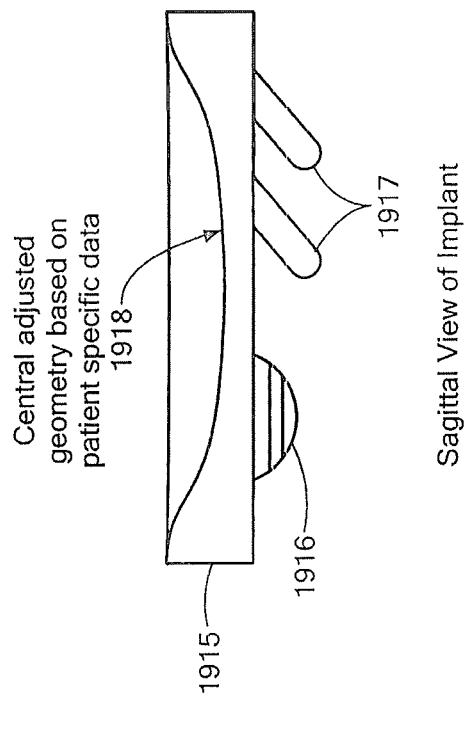
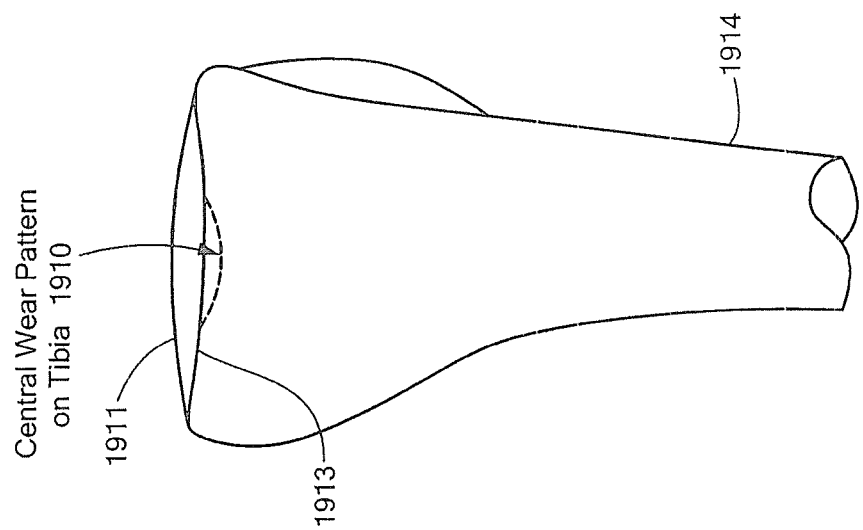
FIG. 19

IMPLANTS FOR ALTERING WEAR PATTERNS OF ARTICULAR SURFACES

CROSS-REFERENCE TO RELATED APPLICATIONS

This application claims priority to U.S. Provisional Application 61/034,035 filed Mar. 5, 2008 and entitled Wear Pattern-Optimized Articular Implants, which is incorporated herein by reference.

FIELD OF THE INVENTION

The embodiments described herein relate to orthopedic methods, systems and devices. In particular, new methods, systems and devices for articular resurfacing in joints including the knee are provided.

BACKGROUND

There are various types of cartilage, e.g., hyaline, elastic and fibrocartilage. Hyaline cartilage is found at the articular surfaces of bones, e.g., in the joints, and is responsible for providing the smooth gliding motion characteristic of moveable joints. Articular cartilage is firmly attached to the underlying bones and measures typically less than 5 mm in thickness in human joints, with considerable variation depending on the joint and the site within the joint.

Adult cartilage has a limited ability of repair; thus, damage to cartilage produced by disease, such as rheumatoid and/or osteoarthritis, or trauma, can lead to serious physical deformity and debilitation. Furthermore, as human articular cartilage ages, its tensile properties change and the cartilage tends to wear away. The superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

In osteoarthritis, human joints such as the knee, hip, ankle, foot joints, shoulder, elbow, wrist, hand joints, and spinal joints tend to wear away the articular cartilage. The wear is frequently not uniform, but localized to a defined region within a joint. For example, in a knee joint, the wear can be on a medial or lateral femoral condyle, a medial or lateral tibial plateau, a medial or lateral trochlea, a medial facet, lateral facet or median ridge of the patella. In a hip joint, the wear can be on an acetabulum or a femoral head or both.

Generally, wear can be limited to one articular surface or it can affect multiple articular surfaces. Wear can occur in one or more subregions on the same articular surface or multiple articular surfaces.

In a medial femoral condyle or medial tibial plateau, wear can occur in an anterior, central or posterior portion of the articular surface. Wear can also occur in a medial or lateral portion of an articular surface. In a lateral femoral condyle or lateral tibial plateau, wear can occur in an anterior, central or posterior portion of the articular surface. Wear can also occur in a medial or lateral portion of an articular surface. In a femoral head or acetabulum, wear can occur in an anterior, posterior, medial or lateral, superior or inferior location.

In short, any location of wear is possible, and any combination of wear patterns on the same articular surface and opposing articular surfaces is possible.

Wear starts typically in the articular cartilage, but it can then extend into the subchondral bone and marrow cavity. Wear can be accompanied by cartilage loss, subchondral sclerosis, subchondral cyst formation, osteophyte formation, bone marrow edema.

Wear is frequently the result of an abnormal biomechanical loading condition in a joint. While modern arthroplasty surgery attempts to correct such abnormal biomechanical loading conditions in a joint, some residual biomechanical loading abnormality or new biomechanical loading abnormality is frequently present after partial or total joint replacement surgery.

Abnormal biomechanical loading of joint implants is a frequent cause for implant failure since current implants cannot account for the increased loads and stresses resulting from such abnormal loading.

Usually, severe damage or cartilage loss is treated by replacement of the joint with a suitable prosthetic material, most frequently metal alloys. See, e.g., U.S. Pat. Nos. 6,383,228; 6,203,576; and 6,126,690. As can be appreciated, joint arthroplasties are highly invasive and require surgical resection of the entire (or a majority of) the articular surface of one or more bones involved in the repair. Typically with these procedures, the marrow space is fairly extensively reamed in order to fit the stem of the prosthesis within the bone. Reaming results in a loss of the patient's bone stock, and over time subsequent osteolysis will frequently lead to loosening of the prosthesis. Further, the area where the implant and the bone mate degrades over time requiring the prosthesis to eventually be replaced. Since the patient's bone stock is limited, the number of possible replacement surgeries is also limited for joint arthroplasty. In short, over the course of 15 to 20 years, and in some cases even shorter time periods, the patient can run out of therapeutic options ultimately resulting in a painful, nonfunctional joint.

SUMMARY

The embodiments described herein are directed to providing methods and devices for correcting wear pattern defects in joints. They provide for improved, and, in some embodiments, optimized or ideal, implant systems to correct or manage abnormal wear patterns. Some of the methods and devices described herein allow for the correction of abnormal biomechanical loading conditions in a joint brought on by wear pattern defects, and also can, in embodiments, permit correction of proper kinematic movement. Abnormal biomechanical loading of conventional joint implants is a frequent cause for implant failure, since current implant designs are unable to account for the increased loads and stresses resulting from such abnormal loading. Alternatively, the methods and devices described herein allow for the accommodation of abnormal biomechanical loading conditions in the shape of the implant system, thus reducing the forces on the implant that can lead to implant failure.

One embodiment is a method for designing an orthopedic device that alters a wear pattern on an articular surface of a joint. The method may include receiving image data associated with the joint, e.g., via a computer network; determining a wear pattern of an articular surface at least in part from the image data; and designing an orthopedic device based at least in part on the image data. The orthopedic device can be designed to alter the wear pattern of the articular surface to a revised wear pattern.

Other embodiments may include one or more of the following. The alteration may be a change to or an improvement over the existing wear pattern, or the wear pattern can be optimized to provide an ideal wear pattern. The image data may be derived from a technique selected from the group consisting of arthroscopy, arthrotomic examination, gait analysis, and imaging analysis; or a combination thereof.

The step of designing can include, for example, altering the wear pattern at least in part by adjusting the location of the wear pattern on the articular surface; altering the wear pattern at least in part by distributing the load that will be placed on the articular surface; or altering the wear pattern at least in part by reducing point loading on the articular surface.

The wear pattern can be determined automatically, semi-automatically, or manually.

The method can further include determining a second wear pattern of a second articular surface of the joint from the image data. The orthopedic device can be designed based at least in part on the image data associated with the second articular surface, and the orthopedic device can be designed to alter the second wear pattern of the second articular surface to a second revised wear pattern. The orthopedic device can be, for example, a bicompartmental resurfacing device for a knee.

A second wear pattern of a second articular surface of the joint can be determined from the image data. A second orthopedic device can be based at least in part on the image data associated with the second articular surface, and the second orthopedic device can be designed to alter the second wear pattern of the second articular surface to a second revised wear pattern. For example, the first orthopedic device can be a tibial tray for a knee and the second orthopedic device can be a second tibial tray for another compartment of the knee.

A second orthopedic device can be designed based at least in part on the image data, and it can be designed to alter the wear pattern of the articular surface to the revised wear pattern. For example, the first orthopedic device can be a tibial tray for a knee joint and the second orthopedic device can be a unicompartmental femoral resurfacing device for the knee joint. The two implants can be designed to be complimentary and thereby affect the alteration in the wear pattern as designed.

The orthopedic device can be many different types of devices such as a replacement hip joint or a knee replacement device including a femoral component and a tibial component. The orthopedic device can be designed using a library of design elements.

The orthopedic device can be designed to include at least one surface that conforms to an existing surface of the joint (see, e.g., U.S. patent application Ser. No. 10/997,407, filed Nov. 24, 2004, which is incorporated herein by reference in its entirety). The orthopedic device can be designed to include at least one surface that is derived from an existing surface of the joint. For example, the derived surface can exclude a defect of the existing surface, it can approximate an ideal surface of the joint, and it can approximate a healthy surface of the joint. Similarly, the orthopedic device can be designed to include at least one curve derived from an existing surface of the joint. For example, the curve can exclude a defect of the existing joint, it can approximate an ideal curve of the joint, and it can approximate a healthy surface of the joint. The orthopedic device also can be designed to include at least one dimension that is derived from an existing dimension of the joint. For example, the derived dimension can exclude a defect of the existing joint, it can approximate an ideal dimension of the joint, and it can approximate a dimension associated with a healthy joint.

The orthopedic device can be designed to be placed at least in part on cartilage associated with the joint, and it can be designed to be placed at least in part on subchondral bone associated with the joint. It can also be designed to be placed on other types of tissue or combinations of tissue.

The method can also include the production of the orthopedic device. For example, the orthopedic device can be produced using traditional methods such as casting or newer technologies, such as direct digital manufacturing. As an alternate example, the orthopedic device can be produced by tailoring a precursor orthopedic device, which may be, e.g., selected from a library of orthopedic devices. Similarly, the orthopedic device can be produced by altering a standard orthopedic device, which may be, e.g., selected from an inventory of orthopedic devices Another embodiment is a method for preparing an implant for correcting an articular surface wear pattern that includes obtaining an image of an articular surface; analyzing the image for the presence or absence of wear pattern indicia; determining a wear pattern from the wear pattern indicia; and providing an implant having a characteristic topography for correcting the wear pattern. The implant can have an interior surface and an outer surface. The interior surface may be a mirror image of the articular surface.

An implant for correcting an articular surface wear pattern, comprising an implant body having a characteristic topography, an interior surface, and an outer surface, where the implant body topography is derived from a wear pattern analysis of the articular surface. The implant can include an interior surface is a mirror image of the articular surface.

Another embodiment is a method of joint arthroplasty that includes: obtaining an image of a surface of a joint; the surface of the joint including a wear pattern; deriving a shape of the joint surface based, at least in part, on the image; and providing an implant having a surface based on the surface of the joint. The implant can be configured to alter the wear pattern of the joint.

Other embodiments may include one or more of the following. Obtaining the image can include an imaging technique selected from the group consisting of x-ray imaging and processing; fluoroscopy; digital tomosynthesis; ultrasound; optical coherence, conventional, cone beam, or spiral computed tomography (CT); single photon emission tomography (SPECT); bone scan; positron emission tomography (PET); magnetic resonance imaging (MRI); thermal imaging; and optical imaging, or a combination thereof. The joint can be any joint with an articular surface, for example, a knee, a shoulder, a hip, a vertebrae, an elbow, an ankle, a foot, a toe, a hand, a wrist and a finger. The wear pattern can be based, at least in part, on one of a presence, absence, location, distribution, depth, area, or dimensions of cartilage loss; presence, absence, location, distribution, depth, area, or dimensions of subchondral cysts; presence, absence, location, distribution, depth, area, or dimensions of subchondral sclerosis; presence, absence, location, distribution, volume, area, depth or dimensions of a subchondral bone plate abnormality; presence, absence, location, distribution, or dimensions of a subchondral bone deformity; presence, absence, or severity of a varus or valgus deformity; presence, absence or severity of recurvatum or antecurvatum; and presence, absence, location, distribution, volume, depth or dimensions of bone marrow edema. The surface of the implant can be substantially at least one of rigid, non-pliable, non-flexible and non-resilient, and can be made of various suitable materials or combinations of materials, e.g., polymer, a cross-linked polymer, a ceramic, a metal, an alloy, and a ceramic-metal composite.

In another embodiment, a wear pattern is determined preoperatively or intraoperatively. Wear patterns may be assessed by, e.g., arthroscopy; arthrotomy; imaging tests such as x-ray imaging; fluoroscopy; digital tomosynthesis; cone beam, conventional and spiral CT; bone scan; SPECT scan; PET; MRI; thermal imaging; optical imaging; and any other current and future technique for detecting articular wear; optical coherence tomography; gait analysis; and techniques merging information from one or more of these tests. Many modifications and derivatives of these imaging tests can be used. For example, with MRI, images can be visually interpreted for assessing cartilage loss or bone deformity. Alternatively, computer methods including maps of cartilage thickness can be utilized for this purpose. Alternatively, a scan reflecting biomechanical composition of the articular cartilage can be performed. These include, but are not limited to, dGEMRIC, T1Rho, and T2 scans.

Different scanning methods within the same modalities and/or different modalities can be combined in order to determine one or more wear patterns.

In one embodiment, a wear pattern can be determined and an implant can be designed or selected that is adapted or optimized for a patient's wear pattern. Such adaptations or optimizations can include in the area of the wear pattern or areas adjacent to a wear pattern: decrease in material thickness; increase in material thickness; change in material composition; change in cross-linking properties, e.g., via local exposure to Gamma radiation or other cross-linking reagents; change in implant shape, e.g., change in convexity or concavity of one or more surface in one or more dimensions; enhanced matching of shape between two mating articular surfaces (enhanced constraint); decreased matching of shape between two mating articular surfaces (decreased constraint).

In one embodiment, an implant can be designed for a wear pattern measured in a patient.

In another embodiment, a wear pattern can be measured in a patient and an implant with a matching wear pattern design can be selected from a library of pre-manufactured implants.

In yet another embodiment, a wear pattern-specific implant shape or geometry is achieved using a number of manufacturing techniques, including, but not limited to: polishing; milling; machining; casting; rapid protocasting; laser sintering; laser melting, and electro abrasion.

In one embodiment, the wear pattern-adapted articular surface is formed de novo. In another embodiment, the wear pattern-adapted articular surface of the implant is achieved by processing an implant with a standard shape of the articular surface (a "blank") and adapting the shape for a patients' wear pattern, e.g., using machining or electroabrasion.

In another embodiment, methods for preparing an implant for correcting or accommodating an articular surface wear pattern are disclosed, wherein an image of an articular surface is obtained; the image is analyzed for the presence or absence of wear pattern indicia; a wear pattern is determined from the wear pattern indicia; and an implant with an inferior surface and a superior surface is provided, having a characteristic topography for correcting or accommodating the wear pattern.

In yet another embodiment, an implant is disclosed for correcting or accommodating an articular surface wear pattern, including an implant body having a characteristic topography, an inferior surface, and a superior surface, where the implant body topography is derived from a wear pattern analysis of the articular surface.

In another embodiment, a method of joint arthroplasty includes obtaining an image of a surface of a joint, the surface of the joint including a wear pattern. A shape of the joint surface is derived based, at least in part, on the image. An implant is provided having a surface that either conforms with or duplicates the surface of the joint.

In related embodiments, obtaining the image may include x-ray imaging and processing; fluoroscopy; digital tomosynthesis; ultrasound; optical coherence, conventional, cone beam, or spiral computed tomography (CT); single photon emission tomography (SPECT); bone scan; positron emission tomography (PET); magnetic resonance imaging (MRI); thermal imaging; or optical imaging, or a combination thereof. The joint may be a knee, shoulder, hip, vertebrae, elbow, ankle, foot, toe, hand, wrist or finger. The wear pattern may be determined based, at least in part, on: a presence, absence, location, distribution, depth, area, or dimensions of cartilage loss; presence, absence, location, distribution, depth, area, or dimensions of subchondral cysts; presence, absence, location, distribution, depth, area, or dimensions of subchondral sclerosis; presence, absence, location, distribution, volume, area, depth or dimensions of a subchondral bone plate abnormality; presence, absence, location, distribution, or dimensions of a subchondral bone deformity; presence, absence, or severity of a varus or valgus deformity; presence, absence or severity of recurvatum or antecurvatum; and/or presence, absence, location, distribution, volume, depth or dimensions of bone marrow edema. The surface of the implant may be substantially rigid, non-pliable, non-flexible and/or non-resilient. The surface of the implant may include a polymer, a cross-linked polymer, a ceramic, a metal, an alloy and/or a ceramic-metal composite. Providing the surface of the implant may include rapid prototyping, laser cutting, laser sintering, electron beam melting, casting and/or milling. The method may further include positioning the implant adjacent an implantation site. The surface of the implant may be shaped prior to positioning the implant adjacent the implantation site.

In accordance with another embodiment, an implant for joint arthroplasty includes an implant surface that either conforms to or duplicates a joint surface, the joint surface including a wear pattern.

In related embodiments, the implant surface may be substantially rigid, non-flexible, and/or non-pliable. The surface of the implant maybe a polymer, a cross-linked polymer, a ceramic, a metal, an alloy and/or a ceramic-metal composite. The implant surface may reflect a surface of the joint obtained from an image.

Novel devices and methods for correcting or accommodating wear patterns in joint surfaces, e.g., cartilage, meniscus and/or bone, are thus described. Advantageously, the implant has an anatomic or near-anatomic fit with the surrounding structures and tissues, thus minimizing bone cutting. In embodiments, devices provided herein also improve the anatomic functionality of the repaired joint by restoring the natural knee joint anatomy and kinematics. This, in turn, leads to an improved functional result for the repaired joint.

BRIEF DESCRIPTION OF THE DRAWINGS

FIG. 2K is a side view of an alternate embodiment of the joint implant of FIG. 2A showing an anchor in the form of a keel. FIG. 2L is a bottom view of an alternate embodiment of the joint implant of FIG. 2A showing an anchor. FIG. 2M shows an anchor in the form of a cross-member. FIG. 2T(1-8) illustrate an alternate embodiment of the tibial implant wherein the surface of the joint is altered to create a flat or angled surface for the implant to mate with.

FIG. 4B is a slightly perspective view of the implant from the superior surface. FIG. 4C is a side view of the implant of FIG. 4B. FIG. 4D is a top view of the inferior surface of the implant; FIGS. 4E and F are perspective side views of the implant. FIG. 4G is an axial view of a femur with the implant installed thereon. FIG. 4H is an anterior view of the knee joint without the patella wherein the implant is installed on the femoral condyle. FIG. 4I is an anterior view of the knee joint with an implant of FIG. 4B implanted on the femoral condyle along with an implant suitable for the tibial plateau, such as that shown in FIG. 2.

FIG. 5A is a top view of the inferior surface of the implant showing a chamfer cut. FIG. 5J is an axial view of a femur with the implant installed on the femoral condyles. FIG. 5K is an anterior view of the knee joint without the patella wherein the implant is installed on the femoral condyle. FIG. 5L is an anterior view of the knee joint with an implant of FIG. 5A implanted on the femoral condyles along with an implant suitable for the tibial plateau, such as that shown in FIG. 2. FIG. 5O depicts an alternate embodiment of the device which accommodates an partial removal of the condyle. FIGS. 5P-S illustrate alternative embodiments of the implant having one or more chamfer cuts.

FIGS. 8E-F illustrate the implant superimposed over a patella. FIGS. 8G-J illustrate an alternate design for the patella implant based on a blank (FIG. 8G).

FIG. 9A depicts the knee with a condyle implant and a patella implant. FIG. 9B depicts an alternate view of the knee with a condyle implant and a patella implant wherein the condyle implant covers a greater portion of the surface of the condyle in the posterior direction. FIG. 9C illustrates a knee joint wherein the implant is provided on the condyle, the patella and the tibial plateau.

FIG. 10A depicts the knee with a tibial implant. FIG. 10B depicts the knee with a condyle implant. FIG. 10C depicts a knee with a tibial implant and a condyle implant. FIG. 10C depicts a knee with a bicompartmental condyle implant and a tibial implant.

FIGS. 17-19 illustrate, in simplified sagittal view, a tibia with medial, lateral and central lateral tibial plateau wear patterns, and a lateral tibial plateau implant featuring a wear pattern correcting surface for each respective type of wear pattern.

DETAILED DESCRIPTION

Figure 1A:
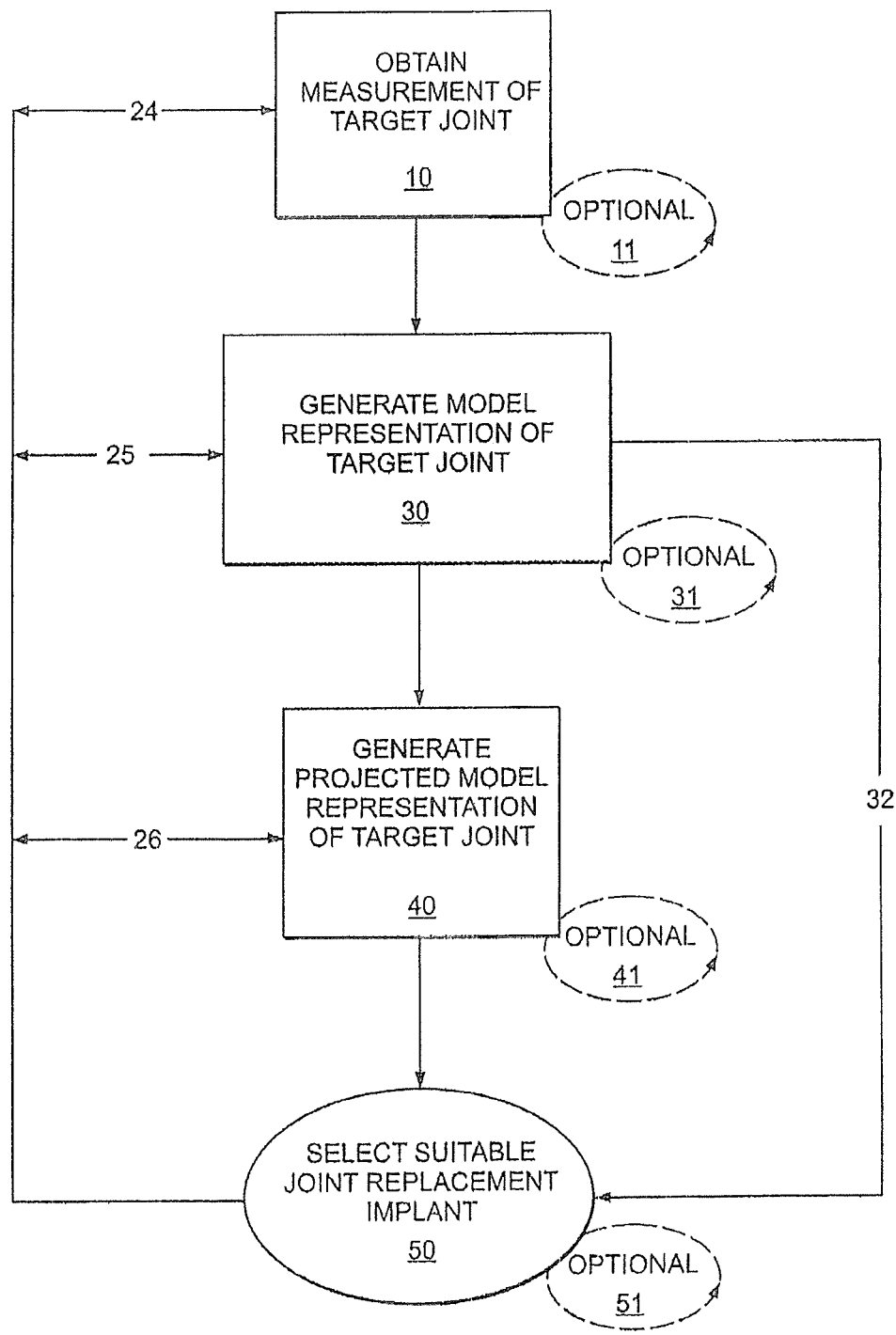
FIG. 1A is a block diagram of a method for assessing a joint in need of repair wherein the existing joint surface is unaltered, or substantially unaltered, prior to receiving the selected implant.

The devices and methods described herein may replace all or a portion (e.g., diseased area and/or area slightly larger than the diseased area) of the articular surface, and achieve an anatomic or near anatomic fit with the surrounding structures and tissues. Where the devices and/or methods include an element associated with the underlying articular bone, the bone-associated element can achieve a near anatomic alignment with the bone. The articular surface may include the superior bone surface of bone ends. For example, the articular surfaces of the knee would include the femoral condyles and the tibial plateau. Healthy articular surfaces would generally be covered by cartilage, but in diseased or worn joints, the articular surface may include areas of exposed bone.

Some embodiments provide methods and devices for repairing joints (including bone end interfaces of the knee, hip, ankle, foot, shoulder, elbow, wrist, hand and spine), particularly for repairing articular surfaces and for facilitating integration of an articular surface repair implant into a subject. The repair may be, without limitation, a cartilage repair/resurfacing implant, a partial joint implant and/or a total joint implant on a single joint surface or multiple joint surfaces. Among other things, the techniques described herein allow for the customization of the implant to suit a particular subject, particularly in terms of correcting or accommodating a wear pattern on the articular size, cartilage thickness and/or curvature. In selected embodiments, the interior surface of the implant is a mirror image of the articular surface, i.e., it is an exact or near anatomic fit, further enhancing the success of repair is enhanced. The implant is designed to incorporate a wear pattern analysis based, on, e.g., electronic images of the articular surface. Some embodiments provide, e.g., minimally invasive methods for partial joint replacement, requiring only minimal or, in some instances, no loss in bone stock. Additionally, unlike with current techniques, the methods described herein will help to restore the integrity of the articular surface by achieving an exact or near anatomic match between the implant and the surrounding or adjacent cartilage and/or subchondral bone.

Methods for Measuring a Wear Pattern

In one embodiment, a wear pattern is determined preoperatively or intraoperatively. Wear patterns may be assessed by, e.g., arthroscopy; arthrotomy; imaging tests such as x-ray imaging; fluoroscopy; digital tomosynthesis; cone beam, conventional and spiral CT; bone scan; SPECT scan; PET; MRI; thermal imaging; optical imaging; and any other current and future technique for detecting articular wear; optical coherence tomography; gait analysis; and techniques merging information from one or more of these tests.

Many modifications and derivatives of these imaging tests can be used. For example, with MRI, images can be visually interpreted for assessing cartilage loss or bone deformity. Alternatively, computer methods including maps of cartilage thickness can be utilized for this purpose. Alternatively, a scan reflecting biomechanical composition of the articular cartilage can be performed. These include, but are not limited to, dGEMRIC, T1Rho, and T2 scans.

Different scanning methods within the same modalities and/or different modalities can be combined in order to determine one or more wear patterns.

Wear patterns may include individual or continuous areas of surface wear, disease or degradation. In some instances the wear pattern may be likened to a map of the articular surface wherein wear pattern indicia are highlighted, marked or otherwise denoted, to indicate the wear pattern. Wear pattern indicia may include the: presence, absence, location, distribution, depth, area, or dimensions of cartilage loss; presence, absence, location, distribution, depth, area, or dimensions of subchondral cysts; presence, absence, location, distribution, depth, area, or dimensions of subchondral sclerosis; presence (e.g., thickening or thinning), absence, location, distribution, volume, area, depth or dimensions of a subchondral bone plate abnormality; presence, absence, location, distribution, or dimensions of a subchondral bone deformity; presence, absence, or severity of a varus or valgus deformity; presence, absence or severity of another articular axis deformity, e.g., recurvatum, antecurvatum; or presence, absence, location, distribution, volume, depth or dimensions of bone marrow edema.

Parameters for Determining a Wear Pattern

A wear pattern can be detected, for example, by determining: presence or absence of cartilage loss; location of cartilage loss; distribution of cartilage loss; depth of cartilage loss; area of cartilage loss; width or dimensions of cartilage loss; presence or absence of subchondral cysts; location of subchondral cysts; distribution of subchondral cysts; volume of subchondral cysts; area of subchondral cysts; presence or absence of subchondral sclerosis; location of subchondral sclerosis; distribution of subchondral sclerosis; volume of subchondral sclerosis; area of subchondral sclerosis; depth or width or dimensions of subchondral sclerosis; presence or absence of abnormality of subchondral bone plate (e.g., thickening or thinning); location of abnormality of subchondral bone plate; distribution of abnormality of subchondral bone plate; volume of abnormality of subchondral bone plate; area of abnormality of subchondral bone plate; depth of abnormality of subchondral bone plate; width or dimensions of abnormality of subchondral bone plate; presence or absence of deformity of subchondral bone; location of deformity of subchondral bone; distribution of deformity of subchondral bone; area of deformity of subchondral bone; dimensions of deformity of subchondral bone; presence of absence of varus or valgus deformity; severity of varus or valgus deformity; presence or absence of other articular axis deformity, e.g., recurvatum, antecurvatum; severity of other articular axis deformity, e.g., recurvatum, antecurvatum; presence or absence of bone marrow edema; location of bone marrow edema; distribution of bone marrow edema; volume of bone marrow edema; area of bone marrow edema; depth of bone marrow edema; or dimensions of bone marrow edema.

One or more of these parameters can be measured preoperatively or intraoperatively. Combinations of parameters can be measured. Linear or non-linear weightings can be applied. Mathematical and statistical modeling can be used to derive a wear pattern using one or more of these parameters or combinations of parameters.

Other parameters can be measured such as presence and severity of ligament tears, muscle strength, body mass index, anthropometric parameters and the like.

Other parameters can include estimated or measured location of ligaments, e.g., medial or lateral collateral ligaments, ACL and PCL, ligamentum capitis femoris, transverse ligament, rotator cuff, spinous ligaments and the like.

These data can be used to improve the localization of a wear pattern. They can also be used to derive risk models of future implant wear.

The resultant information can be used to change or adapt and implant design or to derive an entirely new implant design adapted to a patient's wear pattern.

Influence on Implant Design or Selection

In one embodiment, a wear pattern can be determined and an implant can be designed or selected that is adapted or optimized for a patient's wear pattern. Such adaptations or optimizations can include in the area of the wear pattern or areas adjacent to a wear pattern: decrease in material thickness; increase in material thickness; change in material composition; change in cross-linking properties, e.g., via local exposure to Gamma radiation or other cross-linking reagents; change in implant shape, e.g., change in convexity or concavity of one or more surface in one or more dimensions; enhanced matching of shape between two mating articular surfaces (enhanced constraint); decreased matching of shape between two mating articular surfaces (decreased constraint). The implant may be strengthened in, without limitation, in the area of the wear pattern or areas adjacent to the wear pattern. The implant may be adapted in shape to more evenly distribute load, for example, to areas of less wear.

Changes in material composition can include the use of different materials, e.g., different metals or plastics or ceramics or select use of one or more of these materials in an area of wear pattern or adjacent to an area of wear pattern. Alternatively, select change in material properties of the same material can be used. For example, when a polymer material is used, select cross-linking of polymers can be performed in an area of or adjacent to a wear pattern. Such select cross-linking can, for example, be achieved, with a focused radiation beam, that is focused on the area of wear pattern, or adjacent to wear pattern.

Gradients in material composition and properties extending from an area of wear pattern to areas outside the wear pattern are possible.

Advantages of the devices and methods disclosed herein include (i) customization of joint repair, thereby enhancing the efficacy and comfort level for the patient following the repair procedure; (ii) in some embodiments, eliminating the need for a surgeon to measure the defect to be repaired intraoperatively; (iii) eliminating the need for a surgeon to shape the material during the implantation procedure; (iv) providing methods of evaluating curvature or shape of the repair material based on bone or tissue images or based on intraoperative probing techniques; (v) providing methods of repairing joints with only minimal or, in some instances, no loss in bone stock; (vi) improving postoperative joint congruity; (vii) improving the postoperative patient recovery in some embodiments, (viii) improving postoperative function, such as range of motion and joint kinematics and (ix) improving loading conditions on the implant and thus reducing risk of implant failure.

I. Assessment of Joints and Alignment

The methods and compositions described herein can be used to treat defects resulting from disease of the cartilage (e.g., osteoarthritis), bone damage, cartilage damage, trauma, and/or degeneration due to overuse or age. The size, volume and shape of the area of interest may include only the region of cartilage that has the defect, but preferably includes contiguous parts of the cartilage surrounding the cartilage defect.

Size, curvature and/or thickness measurements can be obtained using any suitable technique. For example, one-dimensional, two-dimensional, and/or three-dimensional measurements can be obtained using suitable mechanical means, laser devices, electromagnetic or optical tracking systems, molds, materials applied to the articular surface that harden and "memorize the surface contour," and/or one or more imaging techniques known in the art. Measurements can be obtained non-invasively and/or intraoperatively (e.g., using a probe or other surgical device). As will be appreciated, the thickness of the repair device can vary at any given point depending upon patient's anatomy and/or the depth of the damage to the cartilage and/or bone to be corrected at any particular location on an articular surface.

FIG. 1A is a flow chart showing steps taken by a practitioner in assessing a joint. First, a practitioner obtains a measurement of a target joint 10. The step of obtaining a measurement can be accomplished by taking an image of the joint. This step can be repeated, as necessary, 11 to obtain a plurality of images in order to further refine the joint assessment process. Once the practitioner has obtained the necessary measurements, the information is used to generate a model representation of the target joint being assessed 30. This model representation can be in the form of a topographical map or image. The model representation of the joint can be in one, two, or three dimensions, and can include a physical model. More than one model can be created 31, if desired. Either or both the original or a subsequently created model can be used. After the model representation of the joint is generated 30, the practitioner can optionally generate a projected model representation of the target joint in a corrected condition 40, e.g., from the existing cartilage on the joint surface, by providing a mirror of the opposing joint surface, or a combination thereof. Again, this step can be repeated 41, as necessary or desired. Using the difference between the topographical condition of the joint and the projected image of the joint, the practitioner can then select a joint implant 50 that is suitable to achieve the corrected joint anatomy. The selection process 50 can be repeated 51 as often as desired to achieve the desired result. Additionally, it is contemplated that a practitioner can obtain a measurement of a target joint 10 by obtaining, for example, an x-ray, and then select a suitable joint replacement implant 50.

As will be appreciated, the practitioner can proceed directly from the step of generating a model representation of the target joint 30 to the step of selecting a suitable joint replacement implant 50 as shown by the arrow 32. Additionally, following selection of suitable joint replacement implant 50, the steps of obtaining measurement of target joint 10, generating model representation of target joint 30 and generating projected model 40, can be repeated in series or parallel as shown by the flow 24, 25, 26.

Figure 1B:
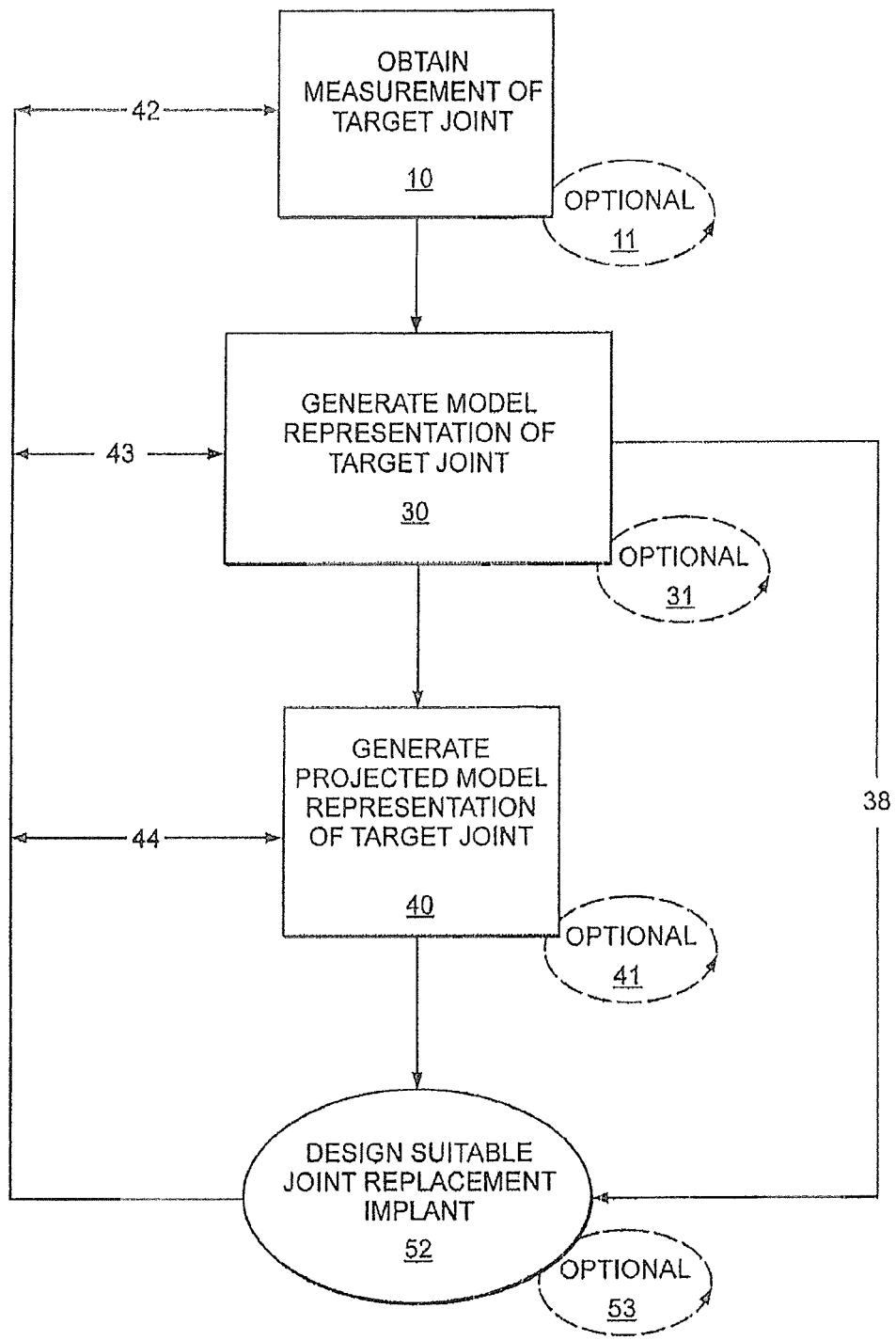
FIG. 1B is a block diagram of a method for assessing a joint in need of repair according wherein the existing joint surface is unaltered, or substantially unaltered, prior to designing an implant suitable to achieve the repair.

FIG. 1B is an alternate flow chart showing steps taken by a practitioner in assessing a joint. First, a practitioner obtains a measurement of a target joint 10. The step of obtaining a measurement can be accomplished by taking an image of the joint. This step can be repeated, as necessary, 11 to obtain a plurality of images in order to further refine the joint assessment process. Once the practitioner has obtained the necessary measurements, the information is used to generate a model representation of the target joint being assessed 30. This model representation can be in the form of a topographical map or image. The model representation of the joint can be in one, two, or three dimensions. The process can be repeated 31 as necessary or desired, and can include a physical model. After the model representation of the joint is assessed 30, the practitioner can optionally generate a projected model representation of the target joint in a corrected condition 40. This step can be repeated 41 as necessary or desired. Using the difference between the topographical condition of the joint and the projected image of the joint, the practitioner can then design a joint implant 52 that is suitable to achieve the corrected joint anatomy, repeating the design process 53 as often as necessary to achieve the desired implant design. The practitioner can also assess whether providing additional features, such as rails, keels, lips, pegs, cruciate stems, or anchors, cross-bars, etc., will enhance the implants' performance in the target joint.

As will be appreciated, the practitioner can proceed directly from the step of generating a model representation of the target joint 30 to the step of designing a suitable joint replacement implant 52 as shown by the arrow 38. Similar to the flow shown above, following the design of a suitable joint replacement implant 52, the steps of obtaining measurement of target joint 10, generating model representation of target joint 30 and generating projected model 40, can be repeated in series or parallel as shown by the flow 42, 43, 44.

Figure 1C:
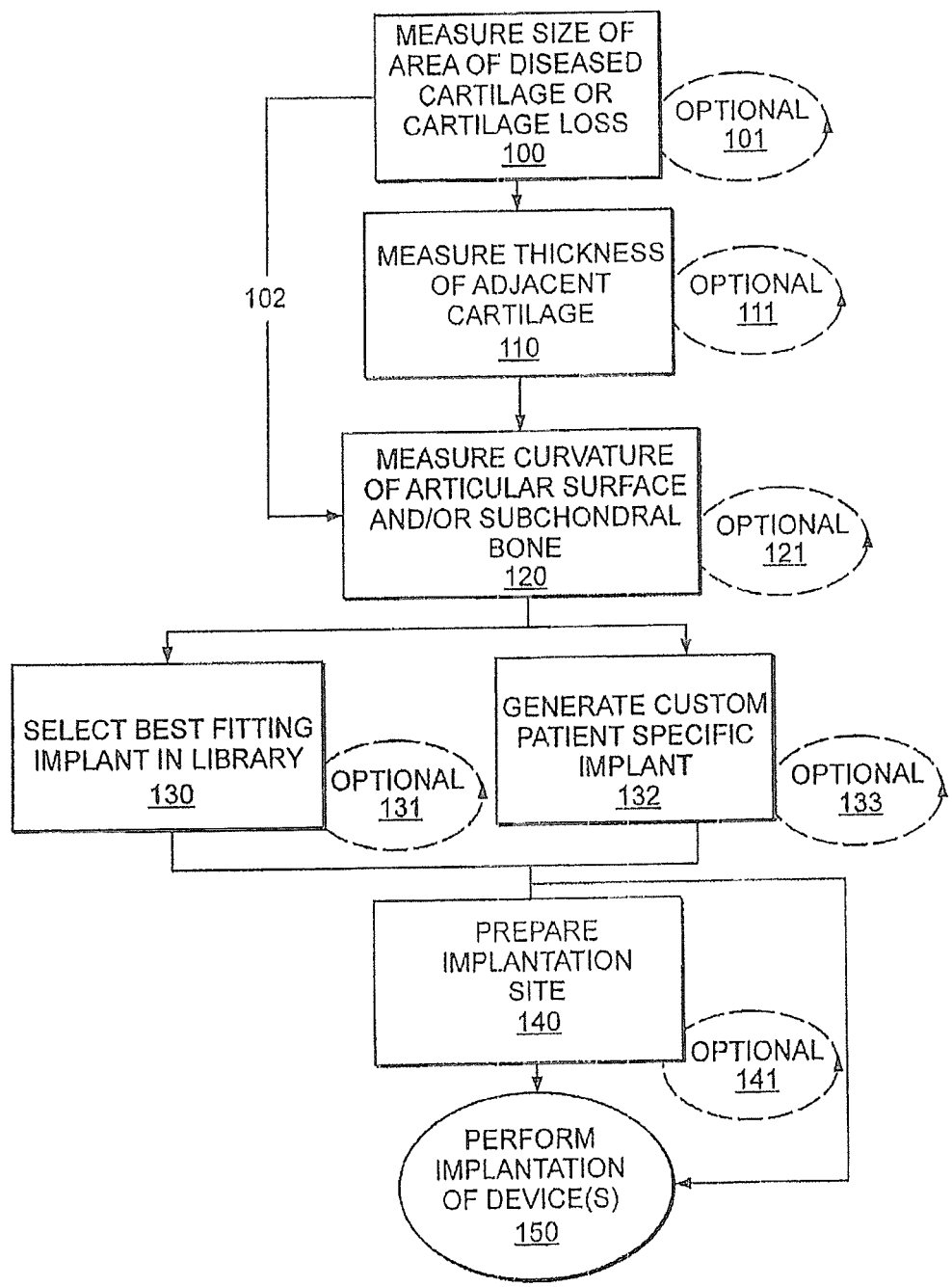
FIG. 1C is a block diagram of a method for developing an implant and using the implant in a patient.

FIG. 1C is a flow chart illustrating the process of selecting an implant for a patient. First, using the techniques described above or those suitable and known in the art, the size of area of diseased cartilage or cartilage loss is measured 100. This step can be repeated multiple times 101, as desired. Once the size of the cartilage defect is measured, the thickness of adjacent cartilage can optionally be measured 110. This process can also be repeated as desired 111. Either after measuring the cartilage loss or measuring the thickness of adjacent cartilage, the curvature of the articular surface is then measured 120. Alternatively, the subchondral bone can be measured. Measurements may also be taken of the surface of the joint being repaired, or of the mating surface in order to facilitate development of the best design for the implant surface.

Once the surfaces have been measured, the user either selects the best fitting implant contained in a library of implants 130, or generates a patient-specific implant 132. These steps can be repeated as desired or necessary, 131, 133, to achieve the best-fitting implant for a patient. As will be appreciated, the process of selecting or designing an implant can be tested against the information contained in the MRI or x-ray of the patient to ensure that the surfaces of the device achieve a good fit relative to the patient's joint surface. Testing can be accomplished by, for example, superimposing the implant image over the image for the patient's joint. Once it has been determined that a suitable implant has been selected or designed, the implant site can be prepared 140, for example by removing cartilage or bone from the joint surface, or the implant can be placed into the joint 150.

The joint implant selected or designed achieves anatomic or near-anatomic fit with the existing surface of the joint while presenting a mating surface for the opposing joint surface that replicates the natural joint anatomy. In this instance, both the existing surface of the joint can be assessed as well as the desired resulting surface of the joint. This technique is particularly useful for implants that are not anchored into the bone.

As will be appreciated, a physician, or other person, can obtain a measurement of a target joint 10 and then either design 52 or select 50 a suitable joint replacement implant.

II. Repair Materials

A wide variety of materials find use in the practice, including, but not limited to, plastics, metals, crystal free metals, ceramics, biological materials (e.g., collagen or other extracellular matrix materials), hydroxyapatite, cells (e.g., stem cells, chondrocyte cells or the like), or combinations thereof. Based on the information (e.g., measurements) obtained regarding the defect and the articular surface and/or the subchondral bone, a repair material can be formed or selected. Further, using one or more of these techniques described herein, a cartilage replacement or regenerating material having a curvature that will fit into a particular cartilage defect, will follow the contour and shape of the articular surface, and will match the thickness of the surrounding cartilage. The repair material can include any combination of materials, and typically includes at least one non-pliable material, for example materials that are not easily bent or changed.

A. Metal and Polymeric Repair Materials

Currently, joint repair systems often employ metal and/or polymeric materials including, for example, prostheses which are anchored into the underlying bone (e.g., a femur in the case of a knee prosthesis). See, e.g., U.S. Pat. Nos. 6,203, 576 and 6,322,588, and references cited therein. A wide variety of metals are useful in the practice, and can be selected based on any criteria. For example, material selection can be based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol™, a nickel-titanium alloy, aluminum, manganese, iron, tantalum, crystal free metals, such as Liquidmetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof.

Suitable synthetic polymers include polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used, such as dextran, hydroxyethyl starch, derivatives of gelatin, polyvinylpyrrolidone, polyvinyl alcohol, poly[N-(2-hydroxypropyl-)methacrylamide], poly(hydroxy acids), poly(epsilon-caprolactone), polylactic acid, polyglycolic acid, poly(dimethyl glycolic acid), poly(hydroxy butyrate), and similar copolymers can also be used.

Other appropriate materials include polyetheretherketone (PEEK™), e.g., PEEK 450G, which is an unfilled PEEK approved for medical implantation available from Victrex (Lancashire, Great Britain, www.matweb.com), Boedeker www.boedeker.com) or Gharda (Panoli, India, www.ghardapolymers.com). The selected material may also be filled. For example, other grades of PEEK are also available, such as 30% glass-filled or 30% carbon filled, provided such materials are cleared for use in implantable devices by the FDA, or other regulatory bodies. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

Other suitable biocompatible thermoplastic or thermoplastic polycondensate materials that resist fatigue, have good memory, are flexible, and/or deflectable have very low moisture absorption, and good wear and/or abrasion resistance, can be used. The implant can also be comprised of other polyketones, e.g., polyetherketoneketone (PEKK), polyetherketone (PEK), polyetherketoneetherketoneketone (PEKEKK), polyetheretherketoneketone (PEEKK), and polyaryletheretherketones. Other suitable polymers include those described in WO 02/02158 A1, WO 02/00275 A1, and WO 02/00270 A1.

Polymers can be prepared by a variety of approaches, including conventional polymer processing methods. Exemplary approaches include injection molding, which is suitable for the production of polymer components with significant structural features; and rapid prototyping, such as reaction injection molding and stereo-lithography. The substrate can be textured or made porous by either physical abrasion or chemical alteration to facilitate incorporation of the metal coating. Other suitable processes include extrusion, injection, compression molding and/or machining techniques. Typically, the polymer is chosen for its physical and mechanical properties and is suitable for carrying and spreading the physical load between the joint surfaces.

More than one metal and/or polymer can be used in combination with each other. For example, one or more metal-containing substrates can be coated with polymers in one or more regions or, alternatively, one or more polymer-containing substrate can be coated in one or more regions with one or more metals.

The system or prosthesis can be porous or porous-coated. The porous surface components can be made of various materials including metals, ceramics, and polymers. These surface components can, in turn, be secured by various means to a multitude of structural cores formed of various metals. Suitable porous coatings include metal, ceramic, polymeric (e.g., biologically neutral elastomers such as silicone rubber, polyethylene terephthalate and/or combinations thereof or combinations thereof. See, e.g., U.S. Pat. Nos. 3,605,123, 3,808, 606, 3,843,975, 3,314,420, 3,987,499 and German Offenlegungsschrift 2,306,552. There can be more than one coating layer, and the layers can have the same or different porosities. See, e.g., U.S. Pat. No. 3,938,198.

The coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See also U.S. Pat. No. 4,213,816. The porous coating can be applied in the form of a powder and the article as a whole subjected to an elevated temperature that bonds the powder to the substrate. Selection of suitable polymers and/or powder coatings can be determined in view of the teachings and references cited herein, for example, based on the melt index of each.

Depending on a wear pattern analysis, it may be advantageous to utilize differing materials or material composition (e.g., varying degrees of polymeric cross linking, or of metal/alloy hardness) in the implant body to address and correct the wear pattern. Variations in material composition throughout the implant body can include the use of different materials, e.g., different metals, plastics or ceramics, or the selection of one or more of these materials in, or adjacent to, the region of the implant corresponding to a wear pattern. As noted above, select changes in material properties of the same material can be used; or, when a polymeric material is employed, selective cross-linking can be performed in an area of or adjacent to a wear pattern to selectively vary the physical properties of the polymer. Selective cross-linking can be achieved, for example with a radiation beam focused on, or adjacent to, the area of the device corresponding to the wear pattern, or by use of selective chemical cross linking.

A wear pattern analysis may include reviewing or analyzing a bone surface to determine the presence of wear pattern indicia. The review or analysis may be determined preoperatively (e.g., via imaging analysis) or intraoperatively, e.g., via arthroscopy, arthrotomic examination, or gait analysis. Linear or non-linear weightings can be applied; and mathematical and statistical modeling can be used to derive a wear pattern from the wear pattern indicia. Other parameters can be considered in determining a wear pattern, including the presence and severity of ligament tears, muscle strength, body mass index, anthropometric parameters, and the estimated or measured location of ligaments, e.g., medial or lateral collateral ligaments, ACL and PCL, ligamentum capitis femoris, transverse ligaments, rotator cuff, and spinous ligaments.

Further considerations in designing the implant body to address and correct the wear pattern include decreasing or increasing material thickness in response to the wear pattern (e.g., part of designing a characteristic topography); change in implant shape, e.g., change in convexity or concavity of one or more surfaces in one or more dimensions; enhanced matching of shape between two mating articular surfaces (enhanced constraint); or decreased matching of shape between two mating articular surfaces (decreased constraint). A characteristic topography may include the relief features of the superior surface, but also variations in thickness of the device from region to region (elevation, in topographic terms.) In an embodiment, an implant can be designed or selected that is adapted or optimized for a patient's wear pattern or areas adjacent to a wear pattern, such adaptations or optimizations resulting in an implant having a characteristic topography.

B. Biological Repair Materials

Repair materials can also include one or more biological material either alone or in combination with non-biological materials. For example, any base material can be designed or shaped and suitable cartilage replacement or regenerating material(s) such as fetal cartilage cells can be applied to be the base. The cells can be then be grown in conjunction with the base until the thickness (and/or curvature) of the cartilage surrounding the cartilage defect has been reached. Conditions for growing cells (e.g., chondrocytes) on various substrates in culture, ex vivo and in vivo are described, for example, in U.S. Pat. Nos. 5,478,739, 5,842,477, 6,283,980, and 6,365,405. Non-limiting examples of suitable substrates include plastic, tissue scaffold, a bone replacement material (e.g., a hydroxyapatite, a bioresorbable material), or any other material suitable for growing a cartilage replacement or regenerating material on it.

Biological polymers can be naturally occurring or produced in vitro, e.g., via fermentation. Suitable biological polymers include collagen, elastin, silk, keratin, gelatin, polyamino acids, cat gut sutures, polysaccharides (e.g., cellulose and starch) and mixtures thereof. Biological polymers can be bioresorbable. Biological materials can be autografts (from the same subject); allografts (from another individual of the same species) and/or xenografts (from another species). See also WO 02/22014 and WO 97/27885. In certain embodiments autologous materials are preferred, as they can carry a reduced risk of immunological complications to the host, including re-absorption of the materials, inflammation and/or scarring of the tissues surrounding the implant site.

Any biological repair material can be sterilized to inactivate biological contaminants such as bacteria, viruses, yeasts, molds, mycoplasmas and parasites. Sterilization can be performed using any suitable technique such as radiation, e.g., gamma radiation.

Any of the biological materials described herein can be harvested with use of a robotic device. The robotic device can use information from an electronic image for tissue harvesting.

III. Device Design

A. Cartilage Models

Using information on thickness and curvature of the cartilage, a physical model of the surfaces of the articular cartilage and of the underlying bone can be created. This physical model can be representative of a limited area within the joint or it can encompass the entire joint. This model can also take into consideration the presence or absence of a meniscus as well as the presence or absence of some or all of the cartilage. For example, in the knee joint, the physical model can encompass only the medial or lateral femoral condyle, both femoral condyles and the notch region, the medial tibial plateau, the lateral tibial plateau, the entire tibial plateau, the medial patella, the lateral patella, the entire patella or the entire joint. The location of a diseased area of cartilage can be determined, for example using a 3D coordinate system or a 3D Euclidian distance as described in WO 02/22014.

In this way, the size of the defect to be repaired can be determined. This process takes into account that, for example, roughly 80% of patients have a healthy lateral component. As will be apparent, some, but not all, defects will include less than the entire cartilage. Thus, in one embodiment, the thickness of the normal or only mildly diseased cartilage surrounding one or more cartilage defects is measured. This thickness measurement can be obtained at a single point or, preferably, at multiple points, for example 2 point, 4-6 points, 7-10 points, more than 10 points or over the length of the entire remaining cartilage. Furthermore, once the size of the defect is determined, an appropriate therapy (e.g., articular repair system) can be selected such that as much as possible of the healthy, surrounding tissue is preserved.

In other embodiments, the curvature of the articular surface can be measured to design and/or shape the repair material. Further, both the thickness of the remaining cartilage and the curvature of the articular surface can be measured to design and/or shape the repair material. Alternatively, the curvature of the subchondral bone can be measured and the resultant measurement(s) can be used to either select or shape a cartilage replacement material. For example, the contour of the subchondral bone can be used to re-create a virtual cartilage surface: the margins of an area of diseased cartilage can be identified. The subchondral bone shape in the diseased areas can be measured. A virtual contour can then be created by copying the subchondral bone surface into the cartilage surface, whereby the copy of the subchondral bone surface connects the margins of the area of diseased cartilage. In shaping the device, the contours can be configured to mate with existing cartilage or to account for the removal of some or all of the cartilage.

Figure 2A:
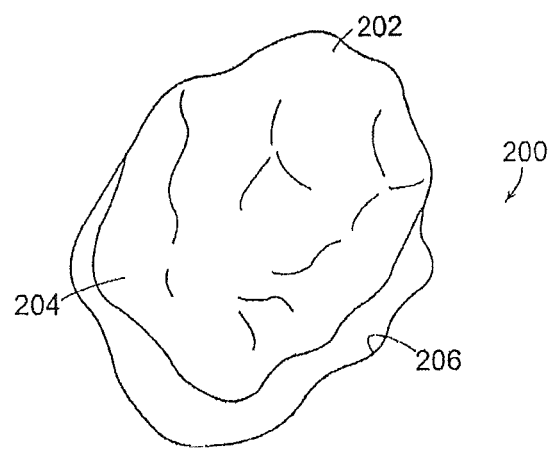
FIG. 2A is a perspective view of a joint implant suitable for implantation at the tibial plateau of the knee joint.

FIG. 2A shows a slightly perspective top view of a joint implant 200 suitable for implantation at the tibial plateau of the knee joint. As shown in FIG. 2A, the implant can be generated using, for example, a dual surface assessment, as described above with respect to FIGS. 1A and B.

The implant 200 has an upper surface 202, a lower surface 204 and a peripheral edge 206. The upper surface 202 is formed so that it forms a mating surface for receiving the opposing joint surface; in this instance partially concave to receive the femur. The concave surface can be variably concave such that it presents a surface to the opposing joint surface, e.g., a negative surface of the mating surface of the femur it communicates with. As will be appreciated, the negative impression need not be a perfect one.

The upper surface 202 of the implant 200 can be shaped by a variety of means. For example, the upper surface 202 can be shaped by projecting the surface from the existing cartilage and/or bone surfaces on the tibial plateau, or it can be shaped to mirror the femoral condyle in order to optimize the complimentary surface of the implant when it engages the femoral condyle. Alternatively, the superior surface 202 (e.g., the outer surface of the implant, i.e., that which will interface with the opposing joint surface, or an implant affixed to the opposing joint surface) can be configured to mate with an inferior surface (e.g., the surface of the implant body that faces the articular surface to which the implant is to be affixed) of an implant configured for the opposing femoral condyle.

The lower surface 204 has a convex surface that matches, or nearly matches, the tibial plateau of the joint such that it creates an anatomic or near anatomic fit with the tibial plateau. Depending on the shape of the tibial plateau, the lower surface can be partially convex as well. Thus, the lower surface 204 presents a surface to the tibial plateau that fits within the existing surface. It can be formed to match the existing surface or to match the surface after articular resurfacing.

As will be appreciated, the convex surface of the lower surface 204 need not be perfectly convex. Rather, the lower surface 204 is more likely consist of convex and concave portions that fit within the existing surface of the tibial plateau or the re-surfaced plateau. Thus, the surface is essentially variably convex and concave.

Figure 2B:
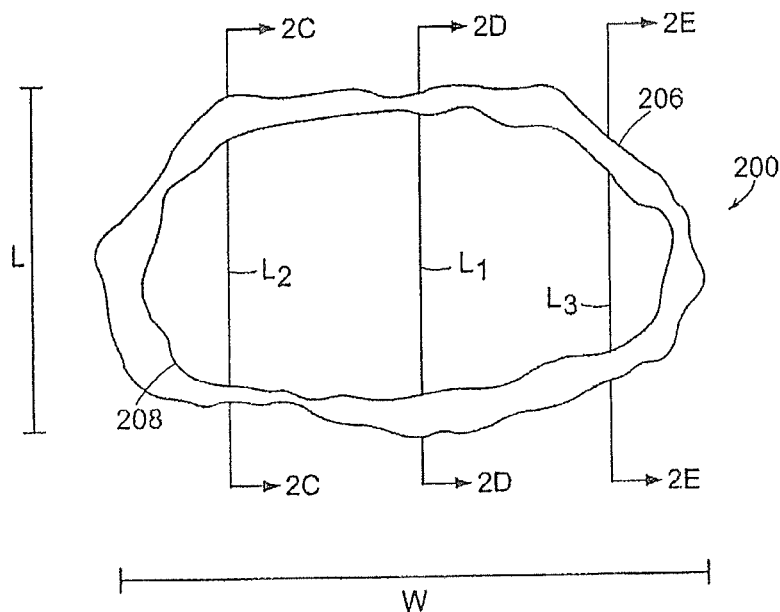
FIG. 2B is a top view of the implant of FIG. 2A.

FIG. 2B shows a top view of the joint implant of FIG. 2A. As shown in FIG. 2B the exterior shape 208 of the implant can be elongated. The elongated form can take a variety of shapes including elliptical, quasi-elliptical, race-track, etc. However, as will be appreciated the exterior dimension is typically irregular thus not forming a true geometric shape, e.g., elliptical. As will be appreciated, the actual exterior shape of an implant can vary depending on the nature of the joint defect to be corrected. Thus the ratio of the length L to the width W can vary from, for example, between 0.25 and 2.0, and more particularly from 0.5 to 1.5. As further shown in FIG. 2B, the length across an axis of the implant 200 varies when taken at points along the width of the implant. For example, as shown in FIG. 2B, $L_1 \neq L_2 \neq L_3$.

Figure 2C:
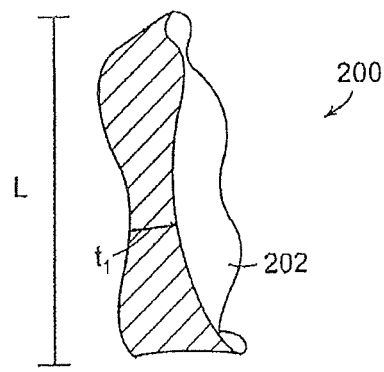
FIG. 2C is a cross-sectional view of the implant of FIG. 2B along the lines C-C shown in FIG. 2B.
Figure 2D:
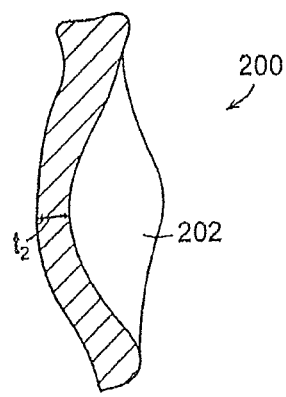
FIG. 2D is a cross-sectional view along the lines D-D shown in FIG. 2B.
Figure 2E:
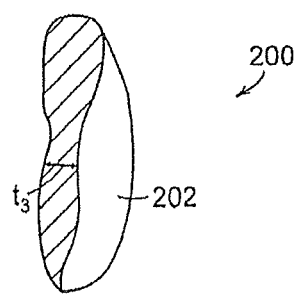
FIG. 2E is a cross-sectional view along the lines E-E shown in FIG. 2B.

Turning now to FIGS. 2C-E, cross-sections of the implant shown in FIG. 2B are depicted along the lines of C-C, D-D, and E-E. The implant has a thickness t1, t2 and t3 respectively. As illustrated by the cross-sections, the thickness of the implant varies along both its length L and width W. The actual thickness at a particular location of the implant 200 is a function of the thickness of the cartilage and/or bone to be replaced and the joint mating surface to be replicated. Further, the profile of the implant 200 at any location along its length L or width W is a function of the cartilage and/or bone to be replaced.

Figure 2F:
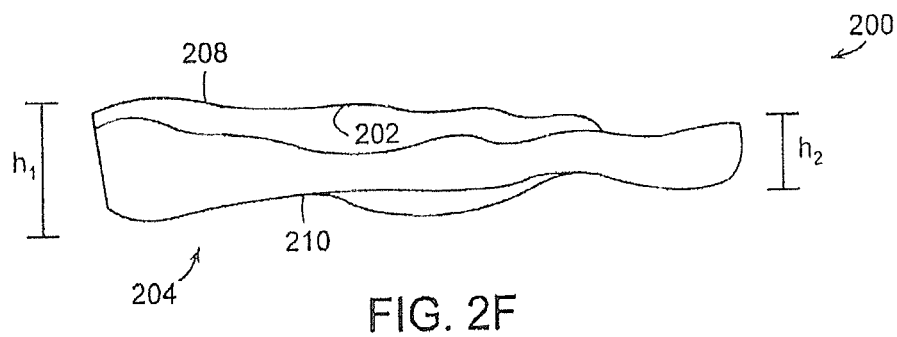
FIG. 2F is a side view of the implant of FIG. 2A.

FIG. 2F is a lateral view of the implant 200 of FIG. 2A. In this instance, the height of the implant 200 at a first end $h_1$ is different than the height of the implant at a second end $h_2$. Further the upper edge 208 can have an overall slope in a downward direction. However, as illustrated the actual slope of the upper edge 208 varies along its length and can, in some instances, be a positive slope. Further the lower edge 210 can have an overall slope in a downward direction. As illustrated the actual slope of the lower edge 210 varies along its length and can, in some instances, be a positive slope. As will be appreciated, depending on the anatomy of an individual patient, an implant can be created wherein $h_1$ and $h_2$ are equivalent or substantially equivalent without departing from the scope.

Figure 2G:
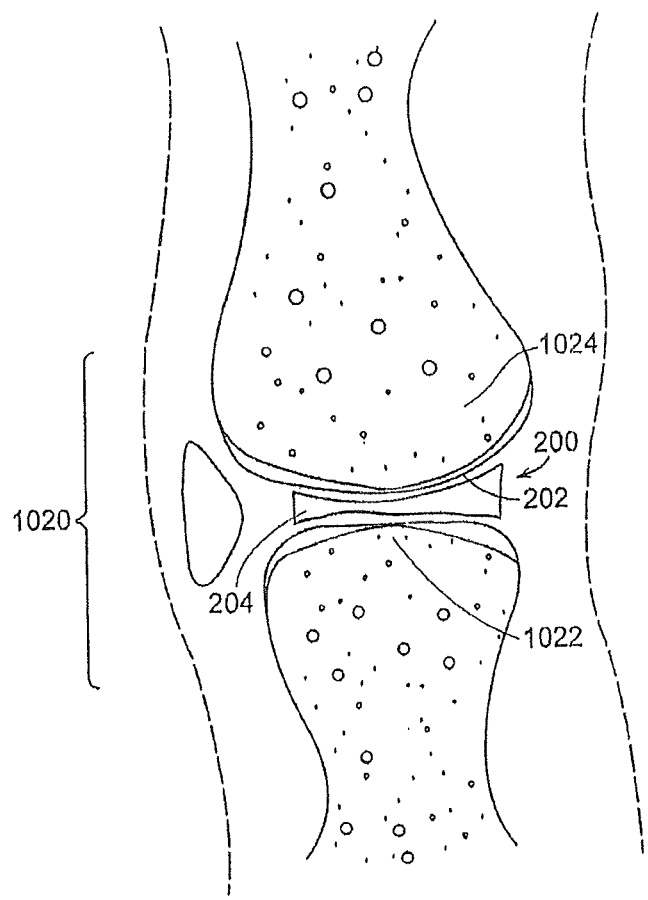
FIG. 2G is a cross-sectional view of the implant of FIG. 2A shown implanted taken along a plane parallel to the sagittal plane.
Figure 2H:
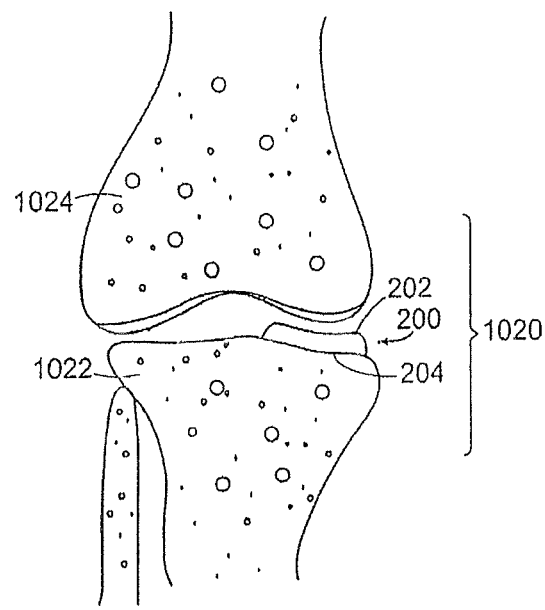
FIG. 2H is a cross-sectional view of the implant of FIG. 2A shown implanted taken along a plane parallel to the coronal plane.

FIG. 2G is a cross-section taken along a sagittal plane in a body showing the implant 200 implanted within a knee joint 1020 such that the lower surface 204 of the implant 200 lies on the tibial plateau 1022 and the femur 1024 rests on the upper surface 202 of the implant 200. FIG. 2H is a cross-section taken along a coronal plane in a body showing the implant 200 implanted within a knee joint 1020. As is apparent from this view, the implant 200 is positioned so that it fits within a superior articular surface 224. As will be appreciated, the articular surface may be the medial or lateral facet, as needed.

Figure 2I:
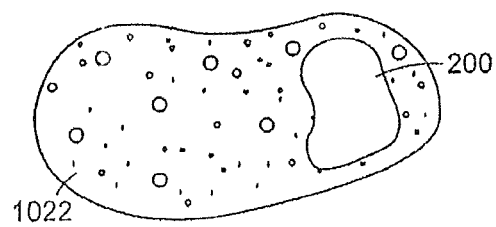
FIG. 2I is a cross-sectional view of the implant of FIG. 2A shown implanted taken along a plane parallel to the axial plane.
Figure 2J:
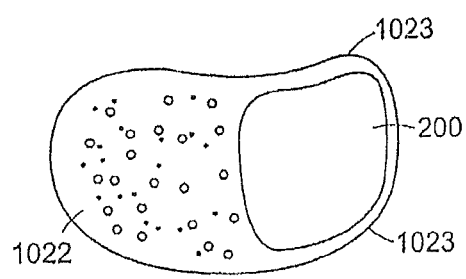
FIG. 2J shows a slightly larger implant that extends closer to the bone medially (towards the edge of the tibial plateau) and anteriorly and posteriorly.

FIG. 2I is a view along an axial plane of the body showing the implant 200 implanted within a knee joint 1020 showing the view taken from an aerial, or upper, view. FIG. 2J is a view of an alternate embodiment where the implant is a bit larger such that it extends closer to the bone medially, i.e., towards the edge 1023 of the tibial plateau, as well as extending anteriorly and posteriorly.

FIG. 2K is a cross-section of an implant 200 according to an alternate embodiment. In this embodiment, the lower surface 204 further includes a joint anchor 212. As illustrated in this embodiment, the joint anchor 212 forms a protrusion, keel or vertical member that extends from the lower surface 204 of the implant 200 and projects into, for example, the bone of the joint. As will be appreciated, the keel can be perpendicular or lie within a plane of the body.

Additionally, as shown in FIG. 2L the joint anchor 212 can have a cross-member 214 so that from a bottom perspective, the joint anchor 212 has the appearance of a cross or an "x." As will be appreciated, the joint anchor 212 may take on a variety of other forms while still accomplishing the same objective of providing increased stability of the implant 200 in the joint. These forms include, but are not limited to, pins, bulbs, balls, teeth, etc. Additionally, one or more joint anchors 212 can be provided as desired. FIGS. 2M and N illustrate cross-sections of alternate embodiments of a dual component implant from a side view and a front view.

Figure 2N:
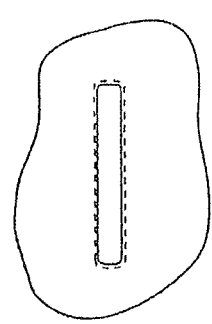
FIGS. 2N-O are alternative embodiments of the implant showing the lower surface have a trough for receiving a cross-bar.
Figure 2O:
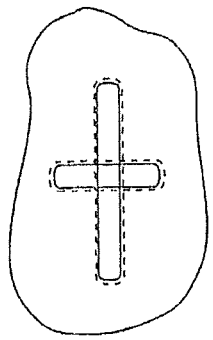
Figure 2P:
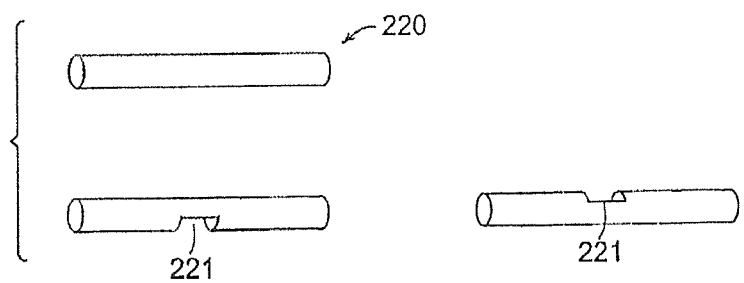
FIG. 2P illustrates a variety of cross-bars.

In an alternate embodiment shown in FIG. 2M it may be desirable to provide a one or more cross-members 220 on the lower surface 204 in order to provide a bit of translation movement of the implant relative to the surface of the femur, or femur implant. In that event, the cross-member can be formed integral to the surface of the implant or can be one or more separate pieces that fit within a groove 222 on the lower surface 204 of the implant 200. The groove can form a single channel as shown in FIG. 2N1, or can have more than one channel as shown in FIG. 2N2. In either event, the cross-bar then fits within the channel as shown in FIGS. 2N1-N2. The cross-bar members 220 can form a solid or hollow tube or pipe structure as shown in FIG. 2P. Where two, or more, tubes 220 communicate to provide translation, a groove 221 can be provided along the surface of one or both cross-members to interlock the tubes into a cross-bar member further stabilizing the motion of the cross-bar relative to the implant 200. As will be appreciated, the cross-bar member 220 can be formed integrally with the implant without departing from the scope.

Figure 2Q:
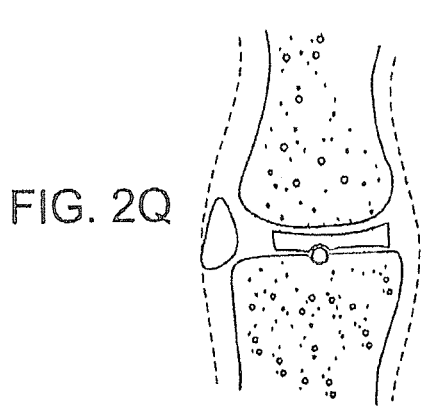
FIGS. 2Q-R illustrate the device implanted within a knee joint.
Figure 2R:
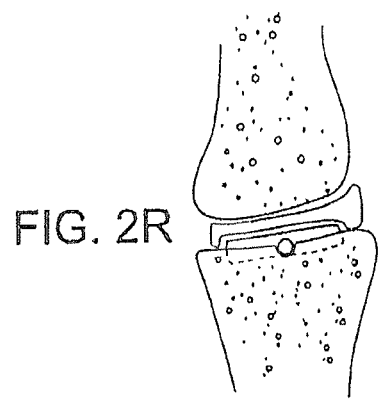
Figures 1, 2S:
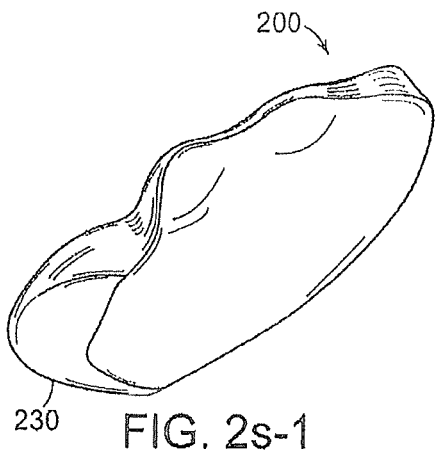
FIGS. 2S(1-9) illustrate another implant suitable for the tibial plateau further having a chamfer cut along one edge.
Figures 2, 2S:
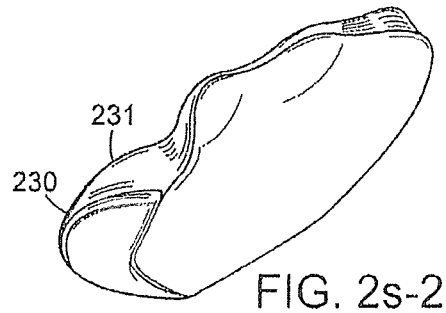

As shown in FIGS. 2Q-R, it is anticipated that the surface of the tibial plateau will be prepared by forming channels thereon to receive the cross-bar members. Thus facilitating the ability of the implant to seat securely within the joint while still providing movement about an axis when the knee joint is in motion.

FIG. 2S(1-9) illustrate an alternate embodiment of implant 200. As illustrated in FIG. 2S the edges are beveled to relax a sharp corner. FIG. 2S(1) illustrates an implant having a single fillet or bevel 230. The fillet is placed on the implant anterior to the posterior portion of the tibial spine. As shown in FIG. 2S(2) two fillets 230, 231 are provided and used for the posterior chamfer. In FIG. 2S(3) a third fillet 234 is provided to create two cut surfaces for the posterior chamfer.

Turning now to FIG. 2S(4) a tangent of the implant is deselected, leaving three posterior curves. FIG. 2S(5) shows the result of tangent propagation. FIG. 2S(6) illustrates the effect on the design when the bottom curve is selected without tangent propagation. The result of tangent propagation and selection is shown in FIG. 2S(7). As can be seen in FIG. 2S(8-9) the resulting corner has a softer edge but sacrifices less than 0.5 mm of joint space. As will be appreciated, additional cutting planes can be added without departing from the scope.

FIG. 2T illustrates an alternate embodiment of an implant 200 wherein the surface of the tibial plateau 250 is altered to accommodate the implant. As illustrated in FIG. 2T(1-2) the tibial plateau can be altered for only half of the joint surface 251 or for the full surface 252. As illustrate in FIG. 2T(3-4) the posterior-anterior surface can be flat 260 or graded 262. Grading can be either positive or negative relative to the anterior surface. Grading can also be used with respect to the implants of FIG. 2T where the grading either lies within a plane or a body or is angled relative to a plane of the body. Additionally, attachment mechanisms can be provided to anchor the implant to the altered surface. As shown in FIG. 2T(5-7) keels 264 can be provided. The keels 264 can either sit within a plane, e.g., sagittal or coronal plane, or not sit within a plane (as shown in FIG. 2T(7)). FIG. 2T(8) illustrates an implant which covers the entire tibial plateau. The upper surface of these implants are designed to conform to the projected shape of the joint as determined under the steps described with respect to FIG. 1, while the lower surface is designed to be flat, or substantially flat to correspond to the modified surface of the joint.

Turning now to FIGS. 3A-I, an implant suitable for providing an opposing joint surface to the implant of FIG. 2A is shown. This implant corrects a defect on an inferior surface of the femur 1024 (e.g., the condyle of the femur that mates with the tibial plateau) and can be used alone, i.e., on the femur 1024, or in combination with another joint repair device. Formation of the surfaces of the devices can be achieved using the techniques described above with respect to the implant of FIG. 2.

Figure 3A:
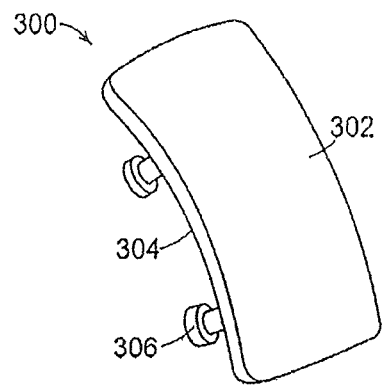
FIGS. 3A and B are perspective views of a joint implant suitable for use on a condyle of the femur from the inferior and superior surface viewpoints, respectively.

FIG. 3A shows a perspective view of an implant 300 having a curved mating surface 302 and convex joint abutting surface 304. The joint abutting surface 304 need not form an anatomic or near anatomic fit with the femur in view of the anchors 306 provided to facilitate connection of the implant to the bone. In this instance, the anchors 306 are shown as pegs having notched heads. The notches facilitate the anchoring process within the bone. However, pegs without notches can be used as well as pegs with other configurations that facilitate the anchoring process or cruciate stems. Pegs and other portions of the implant can be porous-coated. The implant can be inserted without bone cement or with use of bone cement. The implant can be designed to abut the subchondral bone, i.e., it can substantially follow the contour of the subchondral bone. This has the advantage that no bone needs to be removed other than for the placement of the peg holes thereby significantly preserving bone stock.

Figures 2, 2S, 3:
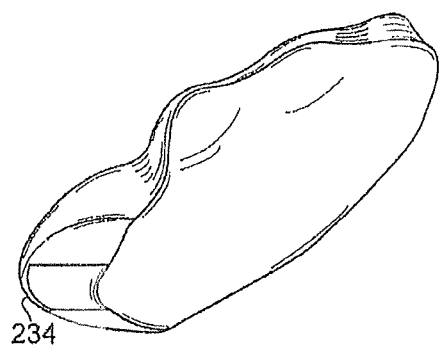

The anchors 306 may take on a variety of other forms, while still accomplishing the objective of providing increased stability of the implant 300 in the joint. These forms include, but are not limited to, pins, bulbs, balls, teeth, etc. Additionally, one or more joint anchors 306 can be provided as desired. As illustrated in FIG. 3, three pins are used to anchor the implant 300. However, more or fewer joint anchors, cruciate stems, or pins, can be used without departing from the scope.

Figure 3B:
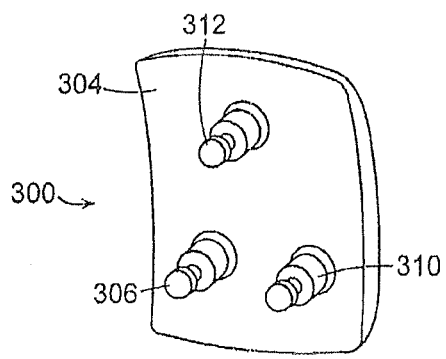
FIG. 3C is a side view of the implant of FIG. 3A.
FIG. 3D is a view of the inferior surface of the implant.
FIG. 3E is a view of the superior surface of the implant and FIG. 3F is a cross-section of the implant.
FIG. 3G is an axial view of a femur with the implant installed thereon.
FIG. 3H is an anterior view of the knee joint without the patella wherein the implant is installed on the femoral condyle.
FIG. 3I is an anterior view of the knee joint with an implant of FIG. 3A implanted on the femoral condyle along with an implant suitable for the tibial plateau, such as that shown in FIG. 2.
FIGS. 3J-K illustrate an alternate embodiment of a joint implant for use on a condyle of a femur further having at least one chamfer cut.
Figure 3C:
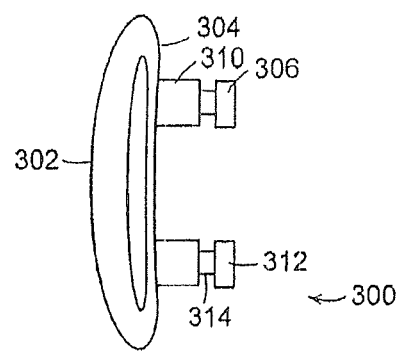

FIG. 3B shows a slightly perspective superior view of the bone mating surface 304 further illustrating the use of three anchors 306 to anchor the implant to the bone. Each anchor 306 has a stem 310 with a head 312 on top. As shown in FIG. 3C, the stem 310 has parallel walls such that it forms a tube or cylinder that extends from the bone mating surface 304. A section of the stem forms a narrowed neck 314 proximal to the head 312. As will be appreciated, the walls need not be parallel, but rather can be sloped to be shaped like a cone. Additionally, the neck 314 need not be present, or the head 312. As discussed above, other configurations suitable for anchoring can be used without departing from the scope.

Figure 3D:
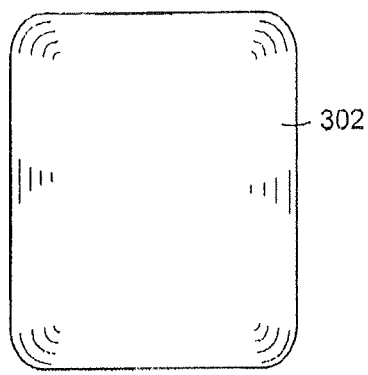
Figure 3E:
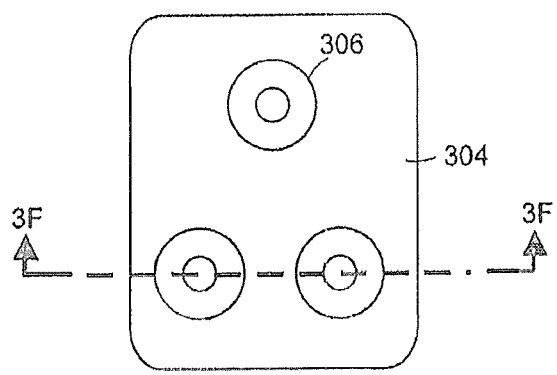
Figure 3F:
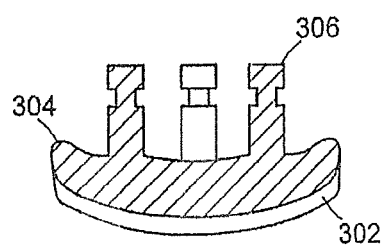

Turning now to FIG. 3D, a view of the tibial plateau mating surface 302 of the implant 300 is illustrated. As is apparent from this view, the surface is curved such that it is convex or substantially convex in order to mate with the concave surface of the plateau. FIG. 3E illustrates the upper surface 304 of the implant 300 further illustrating the use of three pegs 306 for anchoring the implant 300 to the bone. As illustrated, the three pegs 306 are positioned to form a triangle. However, as will be appreciated, one or more pegs can be used, and the orientation of the pegs 306 to one another can be as shown or any other suitable orientation that enables the desired anchoring. FIG. 3F illustrated a cross section of the implant 300 taken along the lines F-F shown in FIG. 3E. Typically the pegs are oriented on the surface of the implant so that the peg is perpendicular to the femoral condyle, which may not result in the peg being perpendicular to the surface of the implant.

Figure 3G:
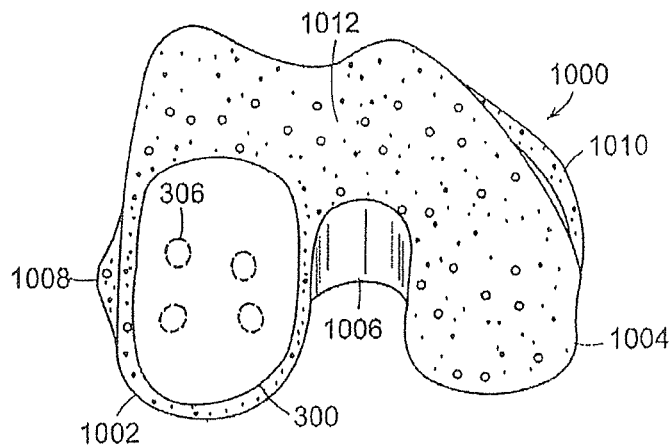

FIG. 3G illustrates the axial view of the femur 1000 having a lateral condyle 1002 and a medial condyle 1004. The intercondylar fossa is also shown 1006 along with the lateral epicondyle 1008 and medial epicondyle 1010. Also shown is the patellar surface of the femur 1012. The implant 300 illustrated in FIG. 3A, is illustrated covering a portion of the lateral condyle. The pegs 306 are also shown that facilitate anchoring the implant 300 to the condyle.

Figures 3H, 3I:
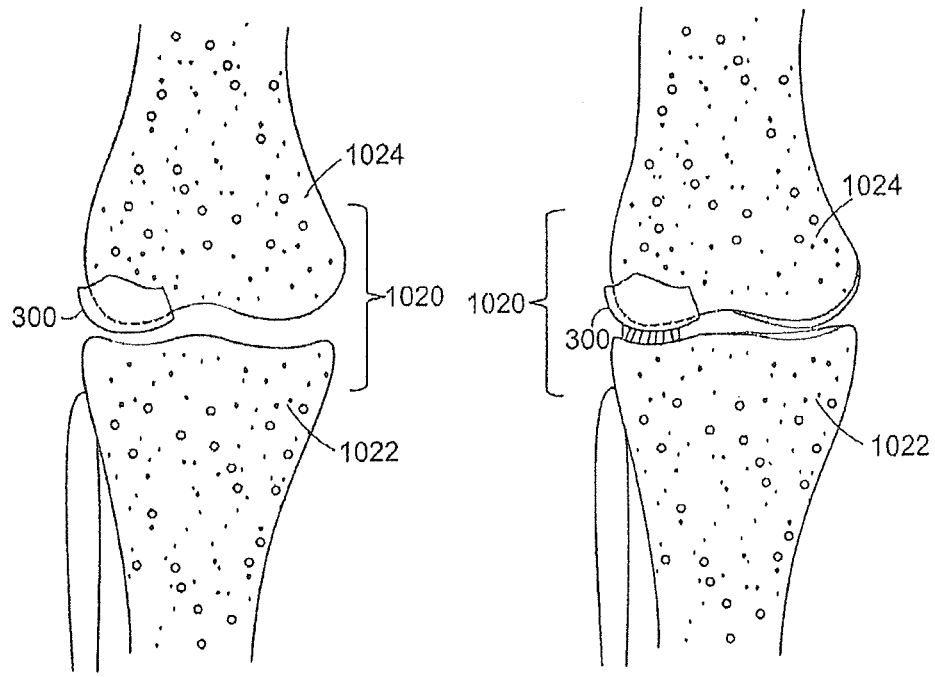

FIG. 3H illustrates a knee joint 1020 from an anterior perspective. The implant 300 is implanted over a condyle. As shown in FIG. 3I, the implant 300 is positioned such that it communicates with an implant 200 designed to correct a defect in the tibial plateau, such as those shown in FIG. 2.

Figure 3J:
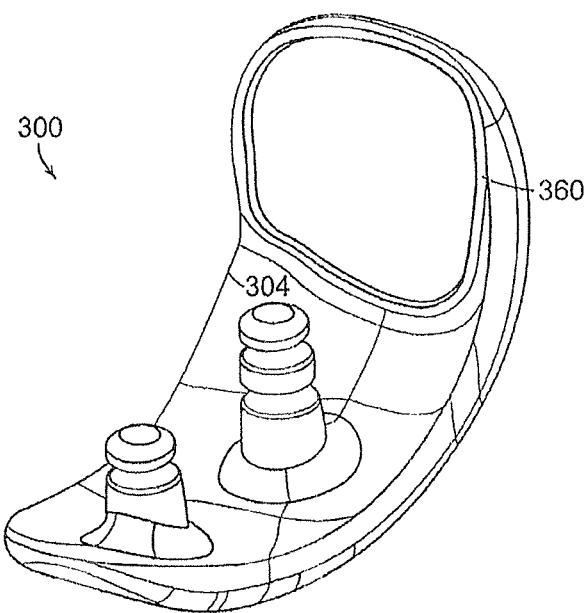
Figure 3K:
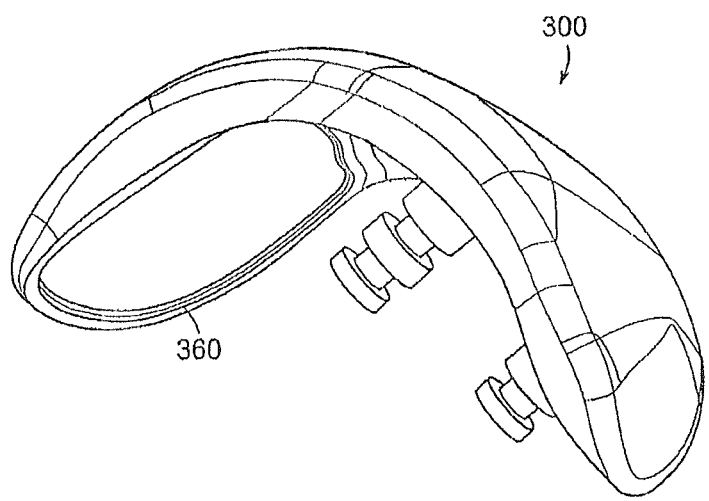

FIGS. 3J-K illustrate an implant 300 for placement on a condyle. In this embodiment, at least one flat surface or chamfer cut 360 is provided to mate with a cut made on the surface of the condyle in preparing the joint. The flat surface 360 typically does not encompass the entire proximal surface 304 of the implant 300.

Figure 4A:
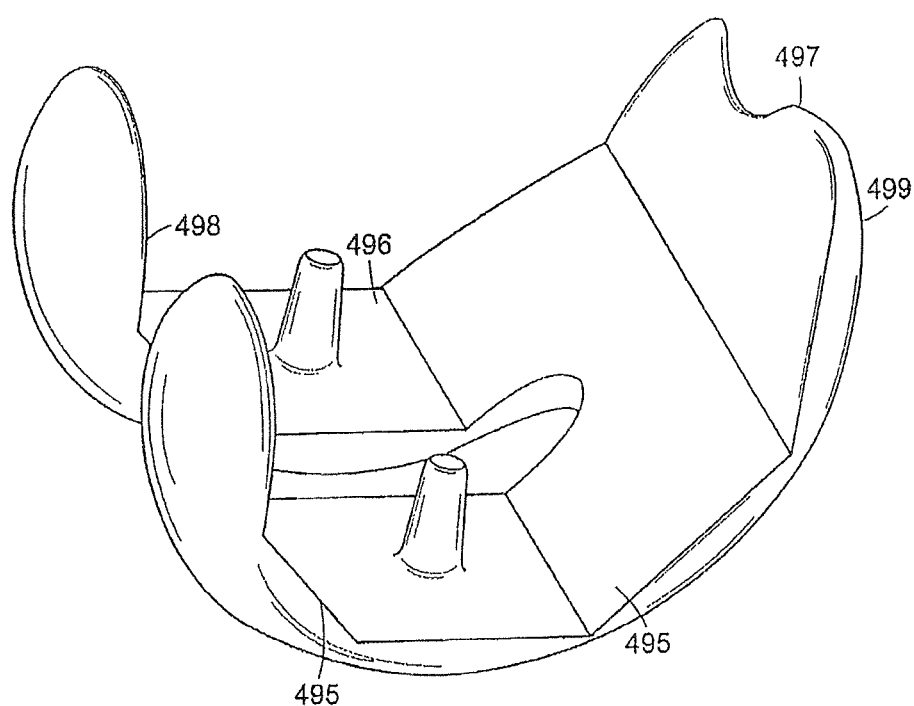
FIG. 4A illustrates an implant suitable for the femoral condyle according to the prior art.

FIG. 4A illustrates the design of a typical total knee arthroplasty ("TKA") primary knee 499. Posterior cuts 498, anterior cuts 497 and distal cuts 496 are provided as well as chamfer cuts 495.

Figure 4B:
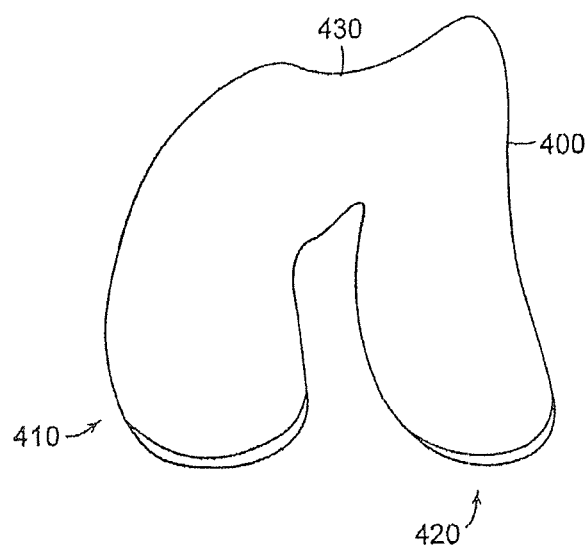
FIGS. 4B-I depict another implant suitable for placement on a femoral condyle.
Figure 4C:
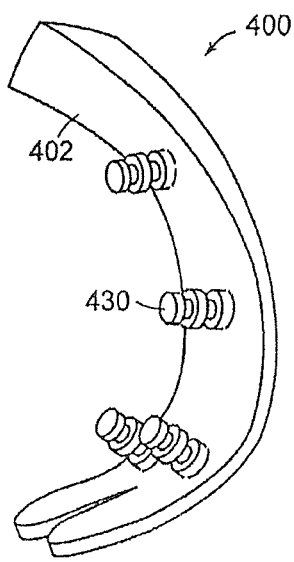

FIGS. 4B and 4C illustrate another implant 400. As shown in FIG. 4B, the implant 400 is configured such that it covers both the lateral and medial femoral condyle, along with the patellar surface of the femur 1012. The implant 400 has a lateral condyle component 410 and a medial condyle component 420 and a bridge 430 that connects the lateral condyle component 410 to the medial condyle component 420 while covering at least a portion of the patellar surface of the femur 1012. The implant 400 can optionally oppose one or more implants, such as those shown in FIG. 2, if desired. FIG. 4C is a side view of the implant of FIG. 4B. As shown in FIG. 4C, the superior surface 402 of the implant 400 is curved to correspond to the curvature of the femoral condyles. The curvature can be configured such that it corresponds to the actual curvature of one or both of the existing femoral condyles, or to the curvature of one or both of the femoral condyles after resurfacing of the joint. One or more pegs 430 can be provided to assist in anchoring the implant to the bone. As will be appreciated, the implant can be configured such that the superior surface contacting a first condyle is configured to male with the existing condyle while a surface contacting a second condyle has one or more flat surfaces to mate with a condyle surface that has been modified.

Figure 4D:
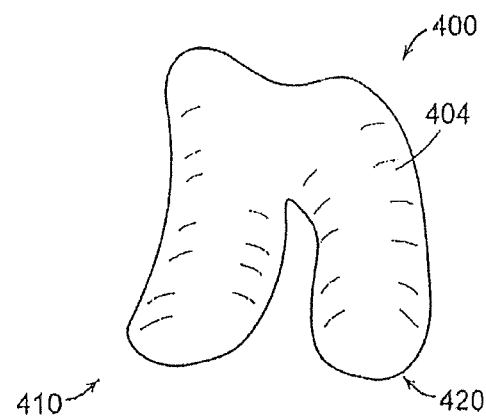

FIG. 4D illustrates a top view of the implant 400 shown in FIG. 4B. As should be appreciated from this view, the inferior surface 404 of the implant 400 is configured to conform to the shape of the femoral condyles, e.g., the shape healthy femoral condyles would present to the tibial surface in a non-damaged joint.

Figure 4E:
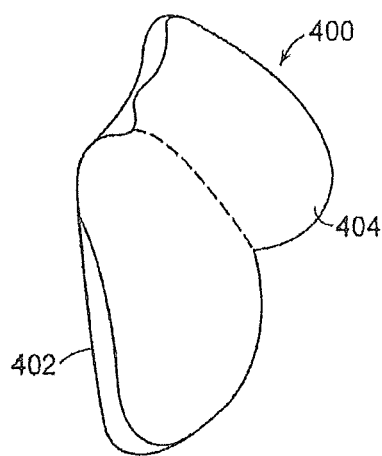
Figure 4F:
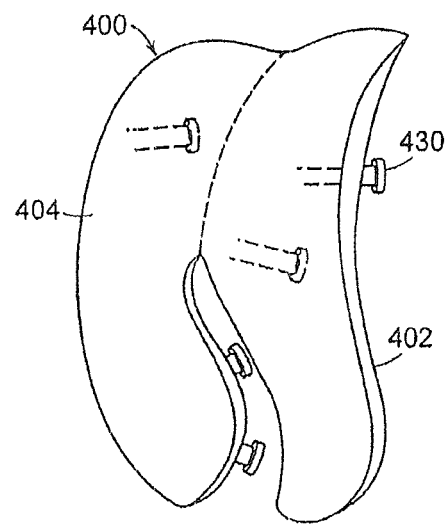

FIGS. 4E and F illustrate perspective views of the implant from the inferior surface (i.e., tibial plateau mating surface).

Figure 4G:
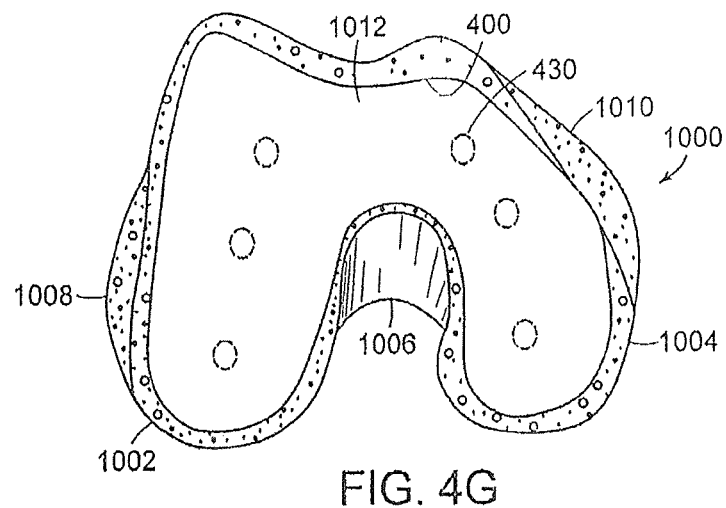

FIG. 4G illustrates the axial view of the femur 1000 having a lateral condyle 1002 and a medial condyle 1004. The intercondylar fossa is also shown 1006 along with the lateral epicondyle 1008. The implant 400 illustrated in FIG. 4B is illustrated covering both condyles and the patellar surface of the femur 1012. The pegs 430 are also shown that facilitate anchoring the implant 400 to the condyle.

Figures 4H, 4I:
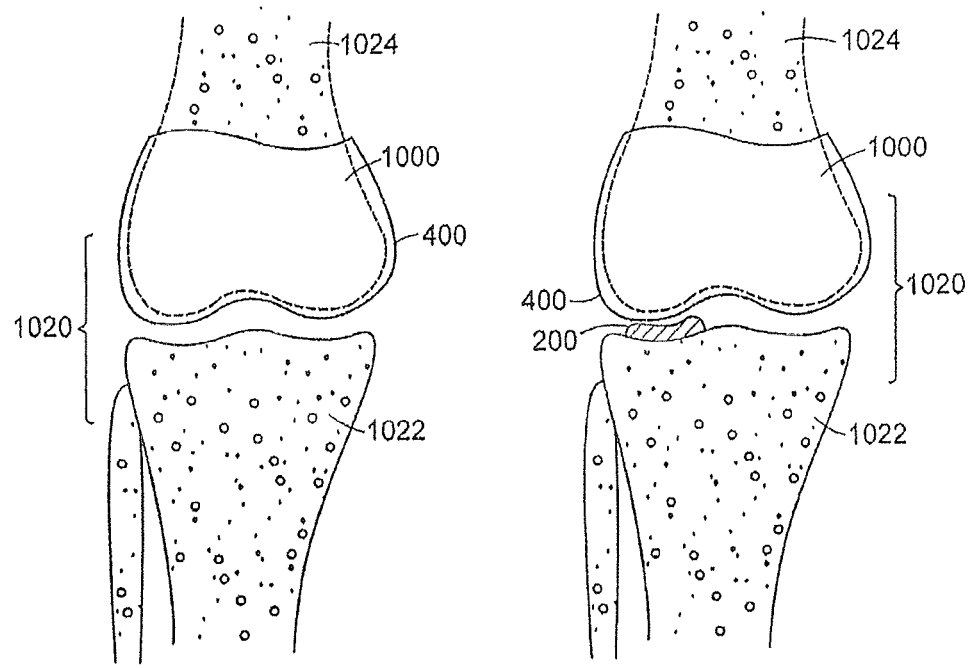

FIG. 4H illustrates a knee joint 1050 from an anterior perspective. The implant 400 is implanted over both condyles. As shown in FIG. 4I, the implant 400 is positioned such that it communicates with an implant 200 designed to correct a defect in the tibial plateau, such as those shown in FIG. 2.

As will be appreciated, the implant 400 can be manufactured from a material that has memory such that the implant can be configured to snap-fit over the condyle. Alternatively, it can be shaped such that it conforms to the surface without the need of a snap-fit.

Figure 5A:
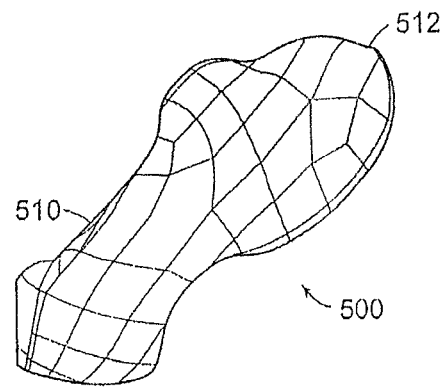
FIGS. 5A-S are depictions of another implant suitable for placement on the femoral condyle.
Figure 5B:
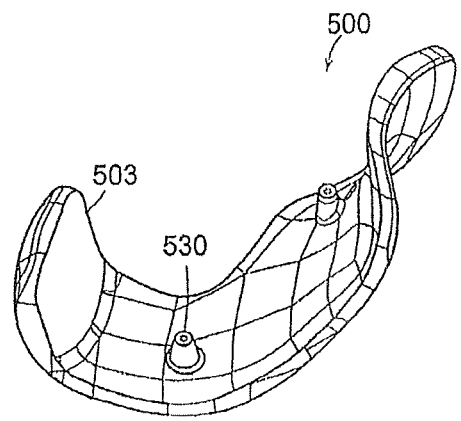
FIG. 5B is a slightly perspective view of the superior surface of the implant.

FIGS. 5A and 5B illustrate yet another implant 500 suitable for repairing a damaged condyle. As shown in FIG. 5A, the implant 500 is configured such that it covers only one of the lateral or medial femoral condyles 510. The implant differs from the implant of FIG. 3 in that the implant 500 also covers at least a portion of the patellar surface of the femur 512.

Figures 2, 2S, 3, 4:
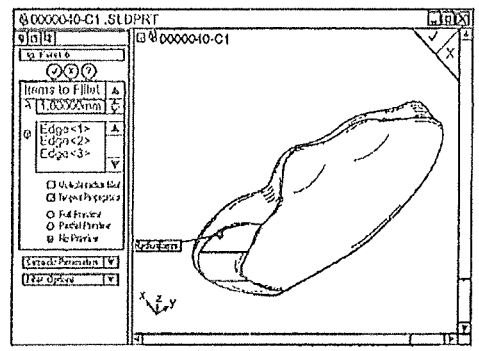
Figure 5C:
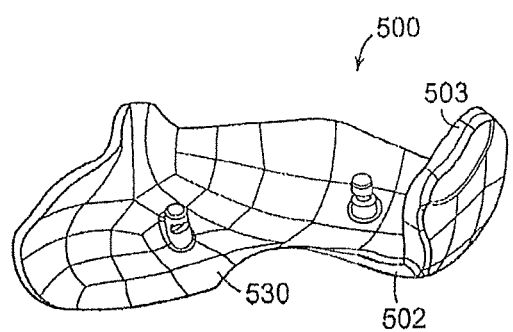
FIG. 5C is a perspective side view of the implant from a first direction.

Similar to the implant of FIG. 4, the implant can optionally oppose one or more implants or opposing joint surfaces, such as those shown in FIG. 2, and can be combined with other implants, such as the implants of FIG. 3. FIG. 5C is a perspective side view of the implant of FIG. 5A. As shown in FIG. 5C, the superior surface 502 of the implant 500 is curved to correspond to the curvature of the femoral condyle that it mates with and the portion of the patellar surface of the femur that it covers. One or more pegs 530 can be provided to assist in anchoring the implant to the bone. Additionally, an angled surface 503 can be provided on an interior surface 502 of the condyle component that conforms to an optionally provided cut made on the surface of the joint surface with which the implant mates.

Figure 5D:
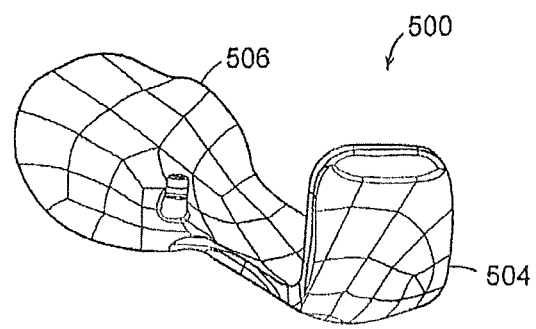
FIG. 5D is a slightly perspective side view of the implant from a second direction.

FIG. 5D illustrates a perspective top view of the implant 500 shown in FIG. 5A. It may be appreciated from this view that the inferior surface 504 of the implant 500 is configured to conform to the projected shape of the femoral condyles, e.g., the shape healthy femoral condyles would present to the tibial surface in a non-damaged joint.

Figure 5E:
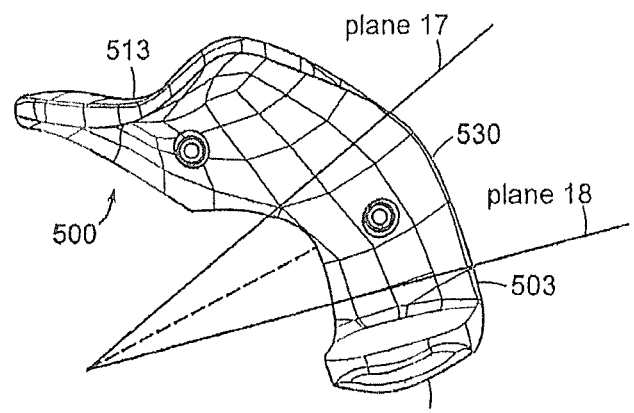
FIGS. 5E-F are side views of the implant showing the bearing loads.
Figure 5F:
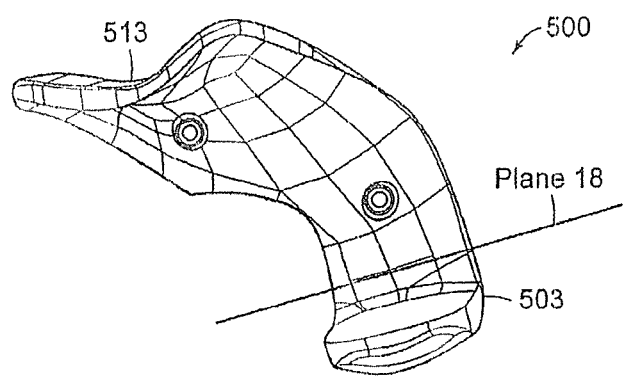

FIG. 5E is a view of the implant 500 showing a hatched three point loading support area which extends from a top portion 513 to a line (plane 17) and from a line (plane 18) to a bottom portion 515. Also illustrated are the pegs 530 extending from the superior surface. FIG. 5F illustrates the superior surface of the implant 500 with the pegs 530 extending from the superior surface. FIG. 5F also illustrates the hatched cantilever loading support area, which extends from the line (plane 18) to the top portion 513 of the implant. The loading forces and directions for each support condition are based on physiological load encounters. Table 1 shows the Physiological Loadings taken from a study by Seth Greenwald.

TABLE 1

| | Physiological Loadings[1] | | |
|---|---|---|---|
| Set-up | "1" | "2" | "3" |
| Flexion Angle (degree) | 0° | 60° | 90° |
| Normal Force N (lbs.) | 2,900 (652) | 3,263 (733.5) | 3,625 (815) |

TABLE 1-continued

Physiological Loadings[1]

| Set-up | "1" | "2" | "3" |
|---|---|---|---|
| Normal Force Case | Walking (4.0 × BW[¥]) | Stair Descent (4.5 × BW[¥]) | Stair Ascent (5.0 × BW[¥]) |

[¥]Body Weight (BW) taken as a 60 year old male, with 173 cm height for an average body weight of 74 kg (163 lbs).
[1]"Tibial Plateau Surface Stress in TKA: A Factor Influencing Polymer Failure Series III-Posterior Stabilized Designs;" Paul D. Postak, B. Sc., Christine S. Heim, B. Sc., A. Seth Greenwald, D. Phil.; Orthopaedic Research Laboratories, The Mt. Sinai Medical Center, Cleveland, Ohio. Presented at the 62nd Annual AAOS Meeting, 1995.

Using the implant 500 described in this application, the three point loading will occur from set-up 1 (2900 N). To replicate a worst case loading scenario, a 75/25 load distribution (75% of 2900 N=2175 N) can be used. The loading will be concentrated on a 6 mm diameter circular area located directly below and normal to the pad on the bearing surface.

Turning to the cantilever loading shown in FIG. 5F, the loading will occur from set-up 3, or 90°, at a 75/25 load distribution (75% of 3625 N=2719 N). As with the above example, the loading will be concentrated on a 6 mm diameter circular area located at the center of the posterior-most portion of the medial condyle normal to the flat cut surface of the posterior condyle.

Figure 5G:
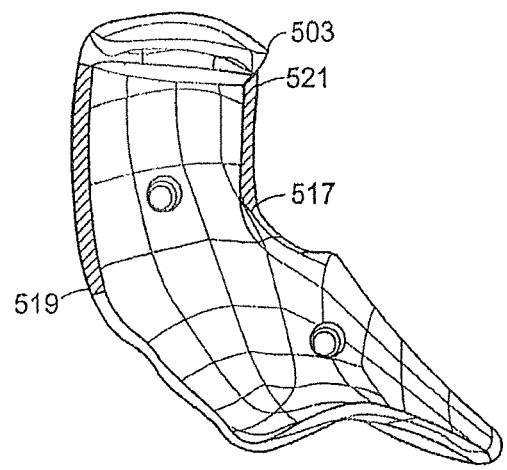
FIGS. 5G and H illustrate an alternative embodiment wherein the implant has lateral rails.
Figure 5H:
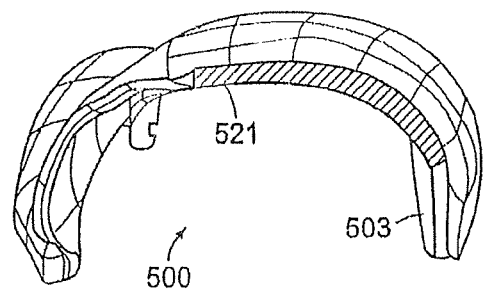

FIGS. 5G and H illustrate alternate embodiments of the implant 500 having a rail design that provides one or more rails 521 along medial and/or lateral sides of the implant 500. The rail 521 can be positioned so that it extends along a portion of the medial 517 and/or lateral 519 sides before communicating with the angled surface 503. As will be appreciated, a single side rail 521 can also be provided.

Figure 5I:
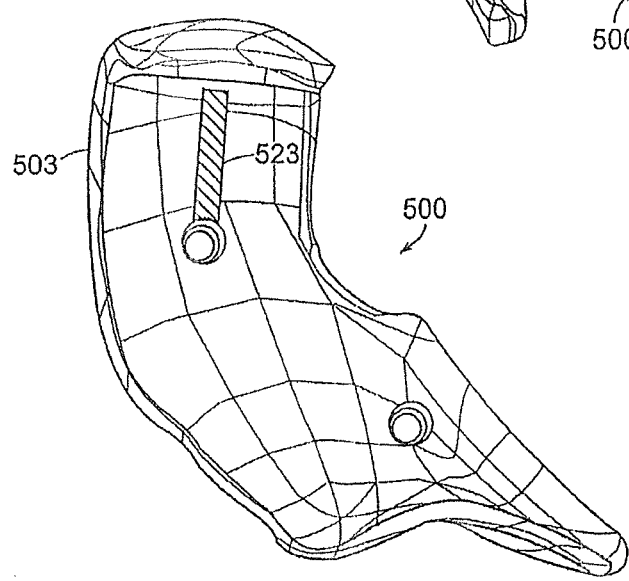
FIG. 5I illustrates another embodiment wherein the implant has an anchoring keel.

FIG. 5I illustrates another embodiment of an implant 500 having a keel design. A keel 523 (or centrally formed rail) is provided on the superior surface of the implant. In this embodiment, the keel 523 is located on the surface of the implant, but not at the sides. As will be appreciated, the keel can be centered, as shown, substantially centered, or located off-center. An angled surface 503 can be provided to communicate with a modified joint surface. Alternatively, where the joint surface is worn or modified, the cut 503 may be configured to mate with the worn or modified surface.

FIG. 5J illustrates the axial view of the femur 1000 having a lateral condyle 1002 and a medial condyle 1004. The intercondylar fossa is also shown 1006 along with the lateral epicondyle 1008 and the medial epicondyle 1010. The patellar surface of the femur 1012 is also illustrated. The implant 500, illustrated in FIG. 5A, is shown covering the lateral condyle and a portion of the patellar surface of the femur 1012. The pegs 530 facilitate anchoring the implant 500 to the condyle and patellar surface.

FIG. 5K illustrates a knee joint 1020 from an anterior perspective. The implant 500 is implanted over the lateral condyle. FIG. 5L illustrates a knee joint 1020 with the implant 500 covering the medial condyle 1004. As illustrated in FIGS. 5K and L, the shape of the implant 500 corresponding to the patella surface may take on a variety of curvatures.

Figures 5M, 5N:
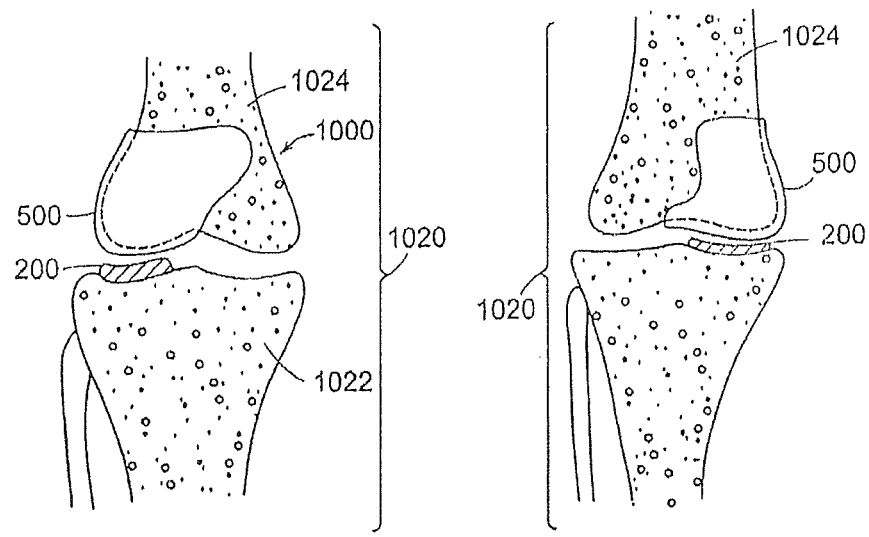
FIGS. 5M-N depicts a device implanted within the knee joint.

Turning now to FIGS. 5M and N the implant 500 is positioned such that it communicates with an implant 200 designed to correct a defect in the tibial plateau, such as those shown in FIG. 2.

In another embodiment, the implant 500 has a superior surface 502 which substantially conforms to the surface of the condyle but which has at one flat portion corresponding to an oblique cut on the bone as shown in FIG. 5O.

Figure 5Q:
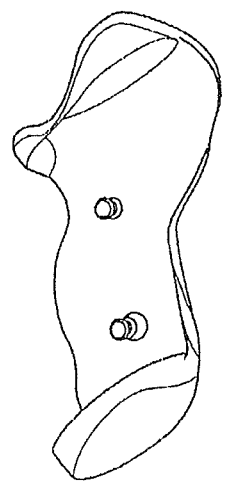
Figure 5S:
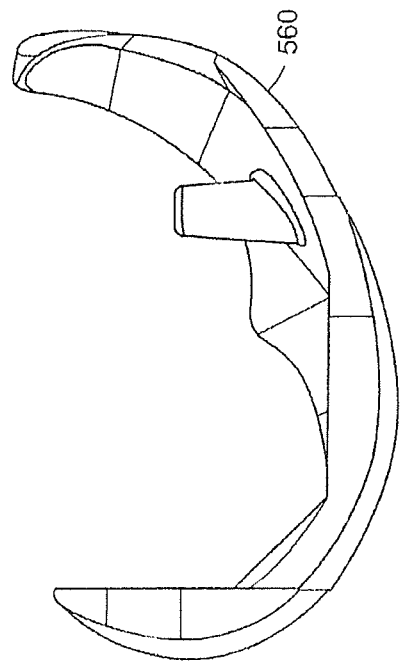
Figure 5P:
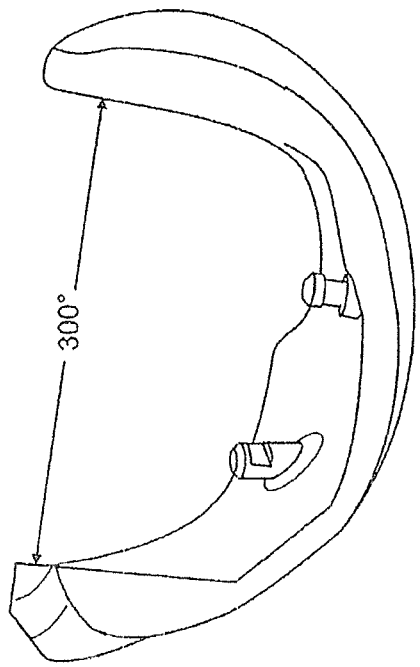

Turning now to FIG. 5P-Q, an implant 500 is shown from a side view with a 7° difference between the anterior and posterior cuts.

Figure 5R:
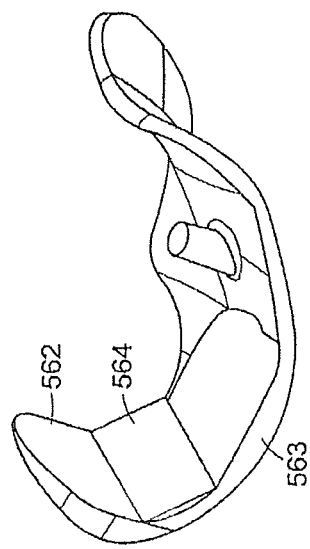

FIG. 5R-S illustrate an implant 500 having a contoured surface 560 for mating with the joint surface and an anterior cut 561 and a posterior cut 562. FIG. 5S shows the same implant 500 from a slightly different angle. FIG. 5T illustrates another implant 500 having a contoured surface 560 for mating with the joint surface and posterior cut 562, a distal cut 563, and a chamfer cut 564. In this embodiment no anterior cut is provided. FIG. 5U illustrates the implant 500 of FIG. 5T from a side perspective. The cuts are typically less than the cut required for a TKA, i.e., typically less than 10 mm. The design of the cuts for this implant allow for a revision surgery to the knee, if required, at a later date.

Figures 2, 2S, 3, 4, 5:
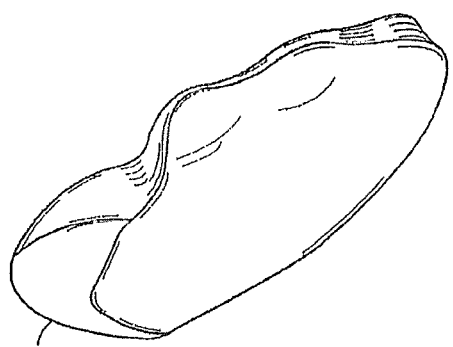
Figures 2, 2S, 3, 4, 5, 6:
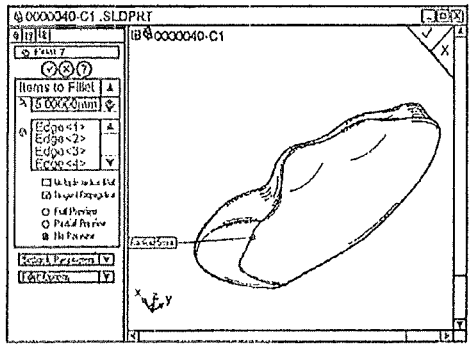
Figure 6A:
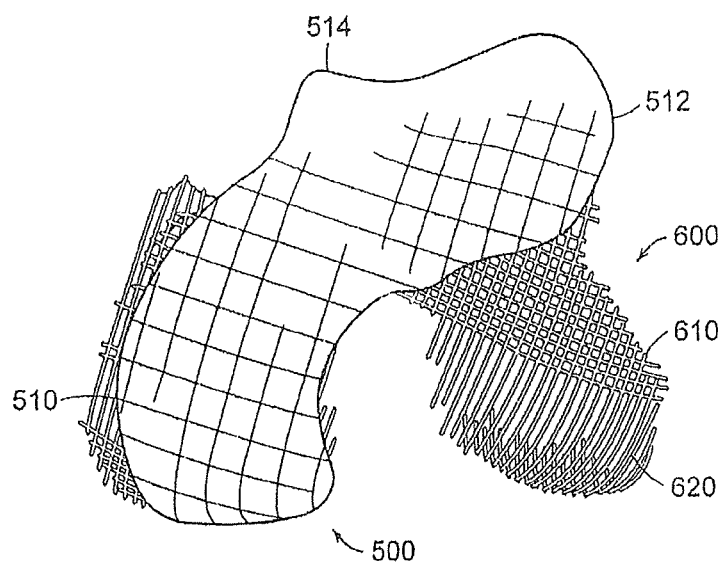
FIGS. 6A-G illustrate a device as shown in FIG. 5 along with a graphical representation of the cross-sectional data points comprising the surface map.

FIGS. 6A-G illustrate the implant 500 of FIG. 5 with a graphical representation of the cross-sections 610, 620 from which a surface shape of the implant is derived. FIG. 6A illustrates a top view of the implant 500 sitting on top of the extracted surface shape 600. This view of the implant 500 illustrates a notch 514 associated with the bridge section of the implant 512 which covers the patellar surface of the femur (or the trochlear region) to provide a mating surface that approximates the cartilage surface. As will be appreciated, the shape of an implant designed for the medial condyle would not necessarily be a mirror image of the implant designed for the lateral condyle because of differences in anatomy. Thus, for example, the notch 514 would not be present in an implant designed for the medial condyle and the patellar surface of the femur. Therefore, the implant can be designed to include all or part of the trochlear region, or to exclude it entirely.

Figure 6B:
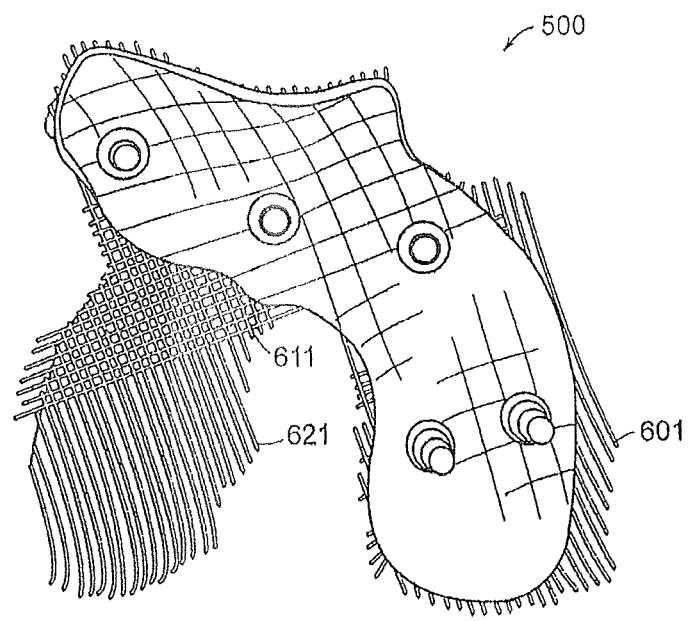
Figure 6C:
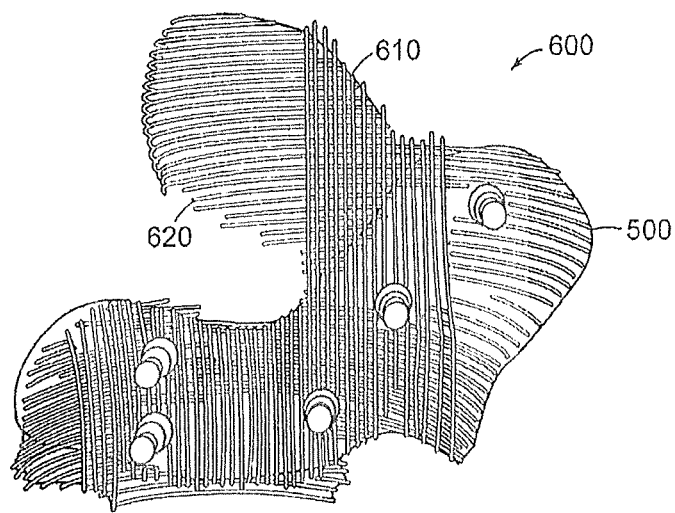
Figure 6D:
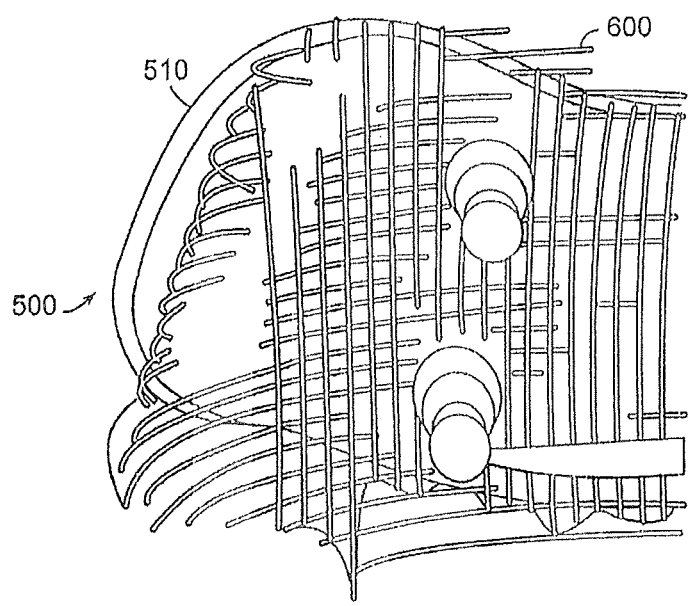
Figure 6E:
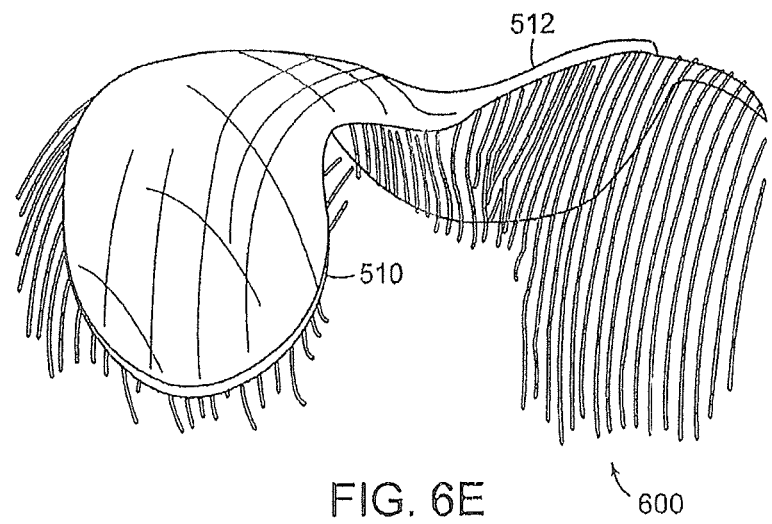
Figure 6F:
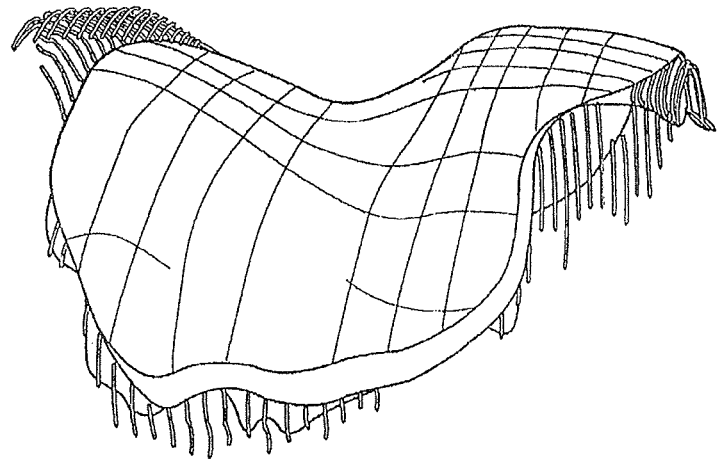
Figure 6G:
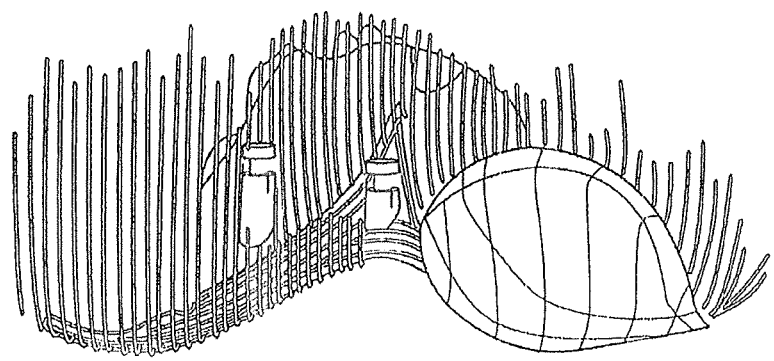

FIG. 6B illustrates a bottom view of the implant 500 layered over another derived surface shape 601. FIG. 6C is a bottom view showing the implant 500 extending through the extracted surface shape 600 shown in FIG. 6A. FIG. 6D is a close-up view of FIG. 6C, showing the condylar wing of the implant covering the extracted surface 600. FIG. 6E illustrates a top posterior view of the implant 500 positioned over the graphical representation of the surface shape 600. FIG. 6F is an anterior view and FIG. 6G is a bottom-posterior view.

Figure 7A:
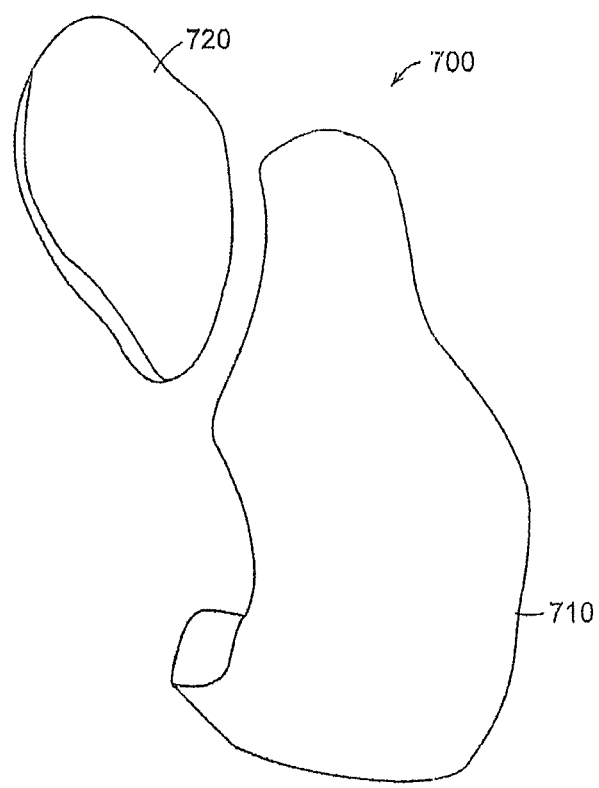
FIGS. 7A-C illustrate an alternate design of a device, suitable for a portion of the femoral condyle, having a two piece configuration.
Figure 7B:
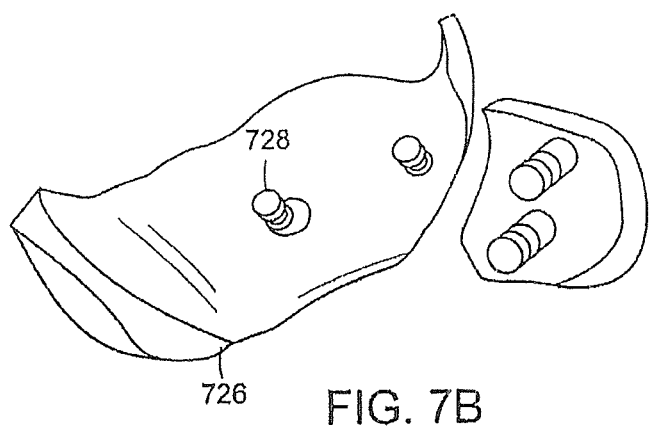
Figure 7C:
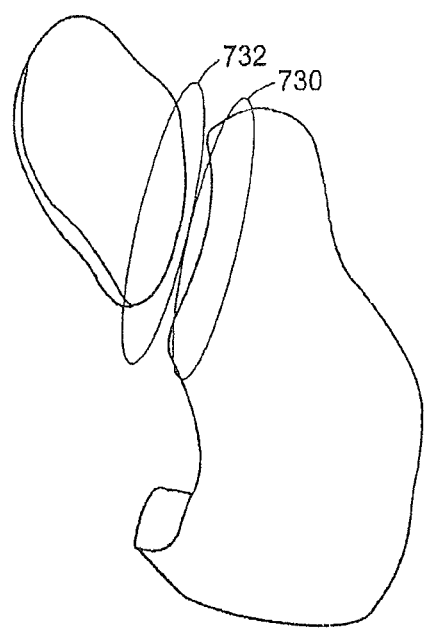

FIG. 7A-C illustrate an implant 700 for correcting a joint similar to the implant 500 above. However, implant 700 consists of two components. The first component 710 engages a condyle of the femur, either medial or lateral depending on the design. The second component 720 engages the patellar surface of the femur. As discussed with the previous embodiments, the surfaces of the implant 700 may be configured such that the distal surface 722 (e.g., the surface that faces the tibial plateau) is shaped based on a projection of the natural shape of the femur compensating the design for valgus or varus deformities and/or flattening of the surface of the femur. Alternatively, the distal surface can be shaped based on the shape of the tibial plateau to provide a surface designed to optimally mate with the tibial plateau. The proximal surface 724 (e.g., the surface that engages the femoral condyle) can be configured such that it mirrors the surface of the femur in either its damaged condition or its modified condition. Likewise, the proximal surface can have one or more flattened sections 726 that form, e.g., chamfer cuts. Additionally the surface can include mechanisms facilitating attachment 728 to the femur, such as keels, teeth, cruciate stems, and the like. The medial facing portion of the condyle implant has a tapered surface 730 while the lateral facing portion of the patellar component also has a tapered surface such that each component presents tapered surfaces 730 to the other component.

By dividing the surfaces of the medial and lateral compartments into independent articulating surfaces, as shown in FIG. 7, the implant provides improved fit of the conformal surfaces to the subchondral bone. Additionally, the lateral-anterior portion of the femur is shielded from stress which could cause bone loss. Also, the smaller size of each component of the implant enables the implant to be placed within the joint using a smaller incision. Finally, the wear of the patellar component is improved.

Figure 8A:
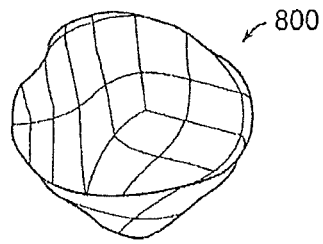
FIGS. 8A-J depict a whole patella (FIG. 8A) and a patella that has been cut in order to install an implant (FIG. 8B). A top and side view of a suitable patella implant is shown (FIGS. 8C-D), and an illustration of the implant superimposed on a whole patella is shown to illustrate the location of the implant dome relative to the patellar ridge.
Figure 8B:
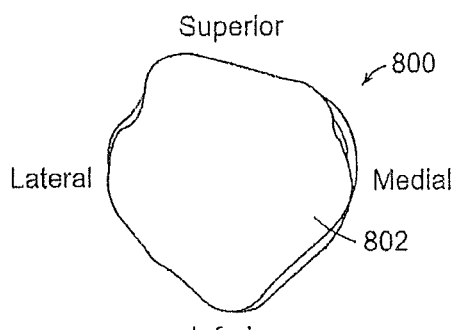
Figure 8C:
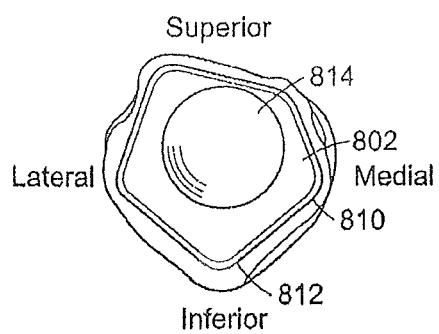
Figure 8D:
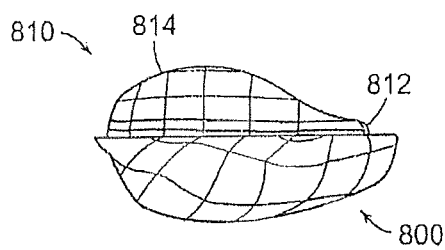

FIGS. 8A-F illustrate a patella 800 with an implant 810. The implant 810 can have one or more pegs, cruciate stems, or other anchoring mechanisms, if desired. As will be appreciated, other designs can be arrived at using the teachings of this disclosure. FIG. 8A illustrates a perspective view of an intact patella 800. FIG. 8B illustrates the patella 800 wherein one surface of the patella 800 has been cut for form a smooth surface 802 to mate with an implant. FIG. 8C illustrates the patella 800 with an implant 810 positioned on the smooth surface 802. The implant 810 has a plate structure 812 that abuts the smooth surface of the patella 802 and a dome 814 positioned on the plate 812 so that the dome is positioned in situ such that it will match the location of the patellar ridge. The implant 810 can be configured such that the edge of the plate is offset 1 mm from the actual edge of the patella, as illustrated. As will be appreciated, the plate 812 and dome 814 can be formed as a single unit or formed from multiple components. FIG. 8D is a side view of the implant 810 positioned on the patella 800. As shown, the dome is positioned on the implant such that it is off-center. Optimal positioning of the dome will be determined by the position of the patellar ridge.

Figure 8E:
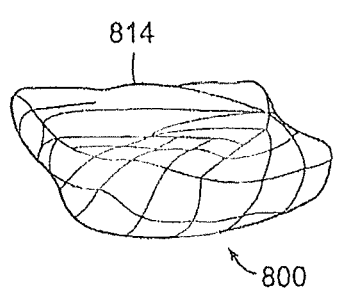
Figure 8F:
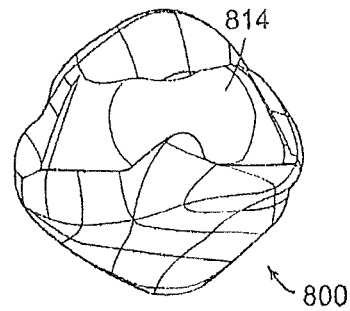

Turning now to FIGS. 8E-F, the implant 810 is shown superimposed on the unaltered patella 800 in order to illustrate that the position of the dome 814 of the implant corresponds to the location of the patellar ridge.

Figure 8G:
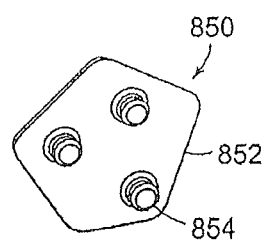
Figure 8H:
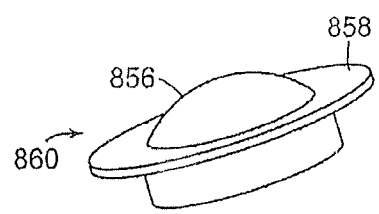
Figure 8I:
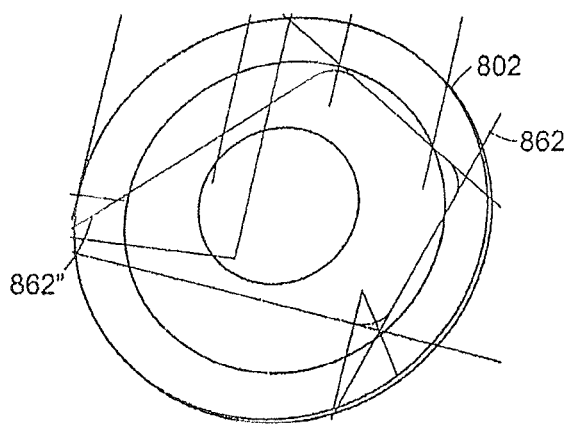
Figure 8J:
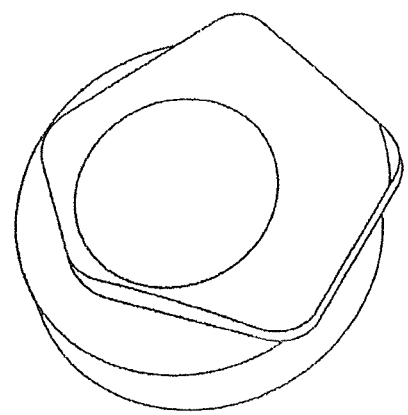

FIGS. 8G-J illustrate an alternative design for the patellar implant. FIG. 8G illustrates the implant 850 in its beginning stages as a blank with a flat inferior surface 852 having pegs 854 extending therefrom for anchoring to the patella. The articular or superior surface 860 has a rounded dome 856, and a round plate section 858 that can be machined to match the bone cut. The articular surface 860 takes on the appearance of a "hat" or sombrero, having a dome with a rim. The center of the dome 856 is also the center of the bearing surface. The rim 858 is cut to conform to the needs of the particular patient. FIG. 8J illustrates an implant which has been formed from the blank shown in FIGS. 8G-I. FIG. 8I shows a plurality of possible cut lines 862, 862' for purposes of illustration.

Figures 9A, 9B, 9C:
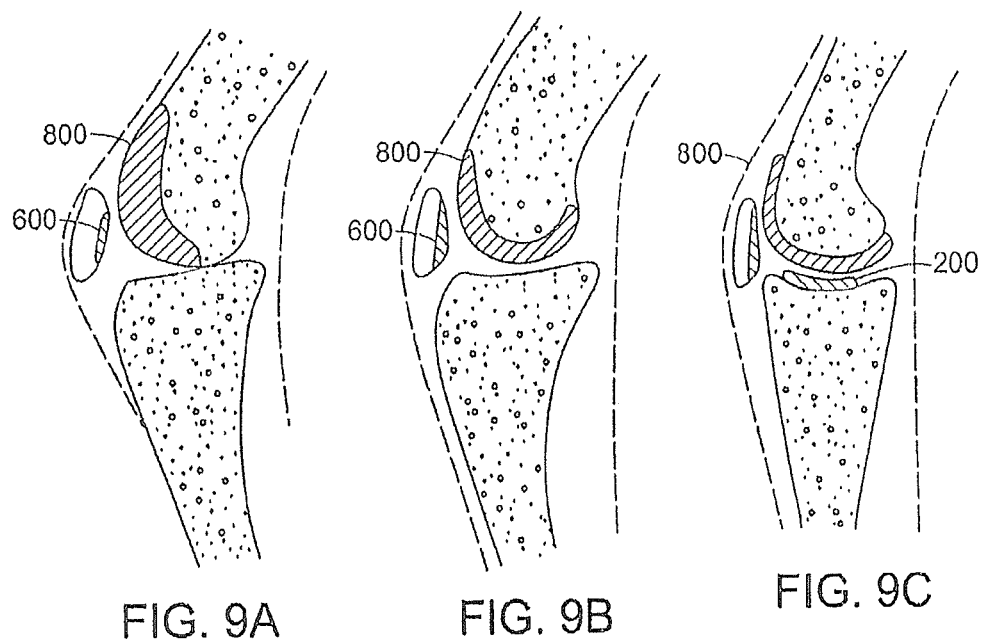
FIGS. 9A-C depict representative side views of a knee joint with any of the devices taught installed therein.
Figure 50:
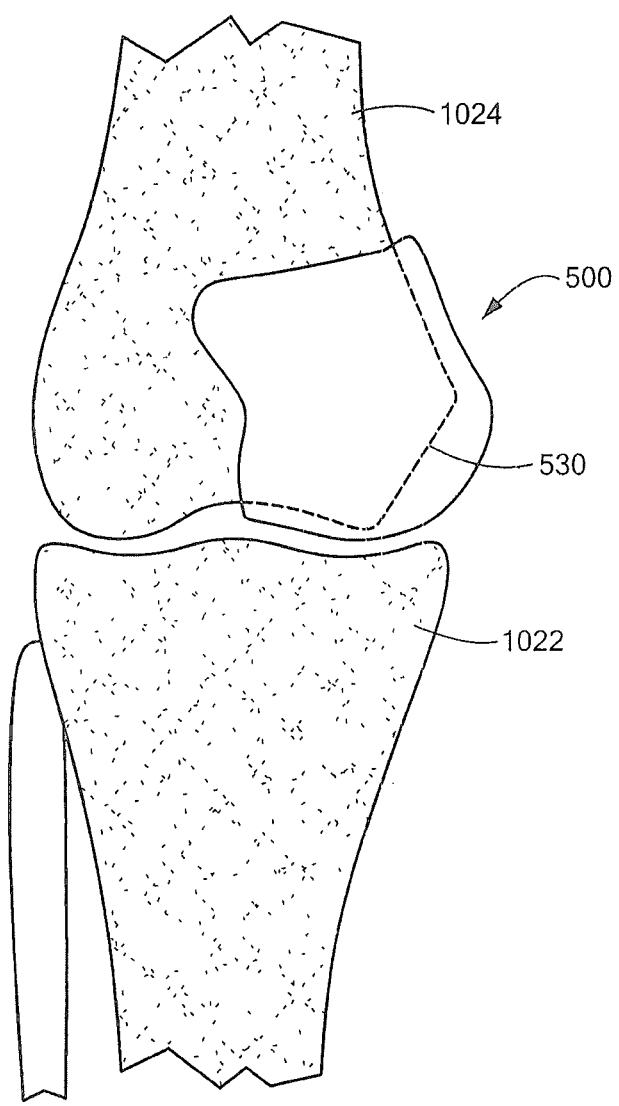

FIGS. 9A-C illustrate a lateral view of a knee 1020 with a combination of implants. In FIG. 9A, an implant covering the condyle 900, is illustrated. Suitable implants can be, for example, those shown in FIGS. 3-8, as will be appreciated the portion of the condyle covered anterior to posterior can include the entire weight bearing surface, a portion thereof, or a surface greater than the weight bearing surface. Thus, for example, the implant can be configured to terminate prior to the sulcus terminalis or after the sulcus terminalis (e.g., the groove on the femur that coincides with the area where load bearing on the joint surface stops). As shown in FIGS. 9A-B, a patellar implant 900 can also be provided. FIG. 9C illustrates a knee having a condyle implant 900, a patellar implant 800 and an implant for the tibial plateau 200.

Figure 10A:
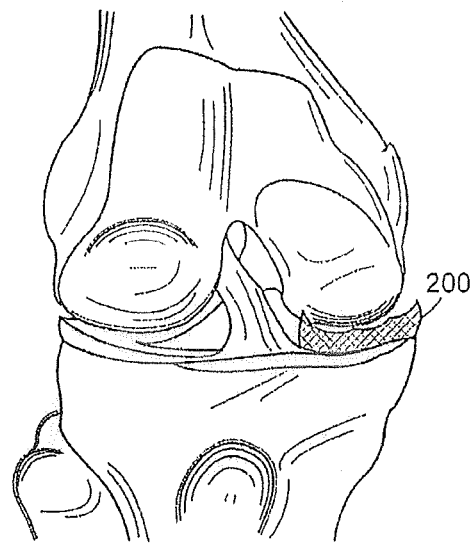
FIGS. 10A-D depict a frontal view of the knee joint with any of the devices taught installed therein.
Figure 10B:
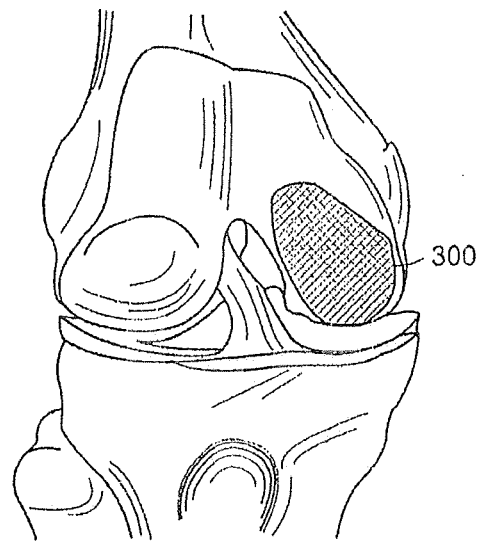
Figure 10C:
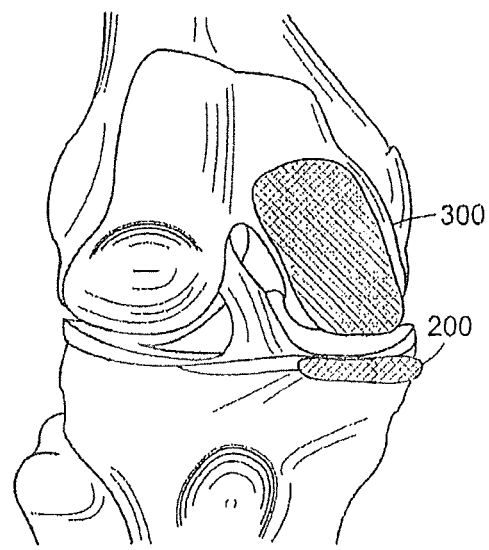
Figure 10D:
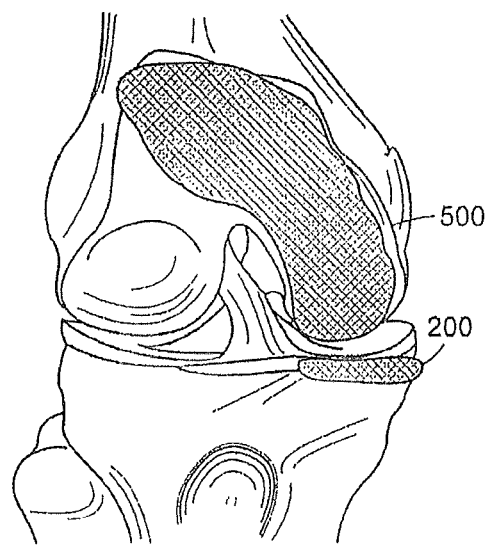

FIGS. 10A-D provide an alternate view of the coronal plane of a knee joint with one or more implants described above implanted therein. FIG. 10A illustrates a knee having a tibial implant 200 placed therein. FIG. 10B illustrates a knee with a condyle implant 300 placed therein. As described above, a plurality of the implants taught herein can be provided within a joint in order to restore joint movement. FIG. 10C illustrates a knee joint having two implants therein. First, a tibial implant 200 is provided on the tibial plateau and a second implant 300 is provided on the facing condyle. The implants may be installed such that the implants present each other mating surfaces (as illustrated), or not. For example, where the tibial implant 200 is placed in the medial compartment of the knee and the condyle implant 300 is placed in the lateral compartment. Other combinations are possible. Turning now to FIG. 10D, a tibial implant 200 is provided along with a bicompartmental condyle implant 500. As discussed above, these implants may or may not be associated with the same compartment of the knee joint.

The arthroplasty system can be designed to reflect aspects of the tibial shape, femoral shape and/or patellar shape. Tibial shape and femoral shape can include cartilage, bone or both. Moreover, the shape of the implant can also include portions or all components of other articular structures such as the menisci. The menisci are compressible, in particular during gait or loading. For this reason, the implant can be designed to incorporate aspects of the meniscal shape accounting for compression of the menisci during loading or physical activities. For example, the undersurface 204 of the implant 200 can be designed to match the shape of the tibial plateau including cartilage or bone or both. The superior surface 202 of the implant 200 can be a composite of the articular surface of the tibia (in particular in areas that are not covered by menisci) and the meniscus. Thus, the outer aspects of the device can be a reflection of meniscal height. Accounting for compression, this can be, for example, 20%, 40%, 60% or 80% of uncompressed meniscal height.

Similarly the superior surface 304 of the implant 300 can be designed to match the shape of the femoral condyle including cartilage or bone or both. The inferior surface 302 of the implant 300 can be a composite of the surface of the tibial plateau (in particular in areas that are not covered by menisci) and the meniscus. Thus, at least a portion of the outer aspects of the device can be a reflection of meniscal height. Accounting for compression, this can be, for example, 20%, 40%, 60% or 80% of uncompressed meniscal height. These same properties can be applied to the implants shown in FIGS. 4-8, as well.

In some embodiments, the outer aspect of the device reflecting the meniscal shape can be made of another, preferably compressible material. If a compressible material is selected it is preferably designed to substantially match the compressibility and biomechanical behavior of the meniscus.

The height and shape of the menisci for any joint surface to be repaired can be measured directly on an imaging test. If portions, or all, of the meniscus are torn, the meniscal height and shape can be derived from measurements of a contralateral joint or using measurements of other articular structures that can provide an estimate on meniscal dimensions.

In another embodiment, the superior face of the implants 300, 400 or 500 can be shaped according to the femur. The shape can preferably be derived from the movement patterns of the femur relative to the tibial plateau thereby accounting for variations in femoral shape and tibiofemoral contact area as the femoral condyle flexes, extends, rotates, translates and glides on the tibia and menisci. The movement patterns can be measured using any current or future test know in the art such as fluoroscopy, MRI, gait analysis and combinations thereof.

The arthroplasty can have two or more components, one essentially mating with the tibial surface and the other substantially articulating with the femoral component. The two components can have a flat opposing surface. Alternatively, the opposing surface can be curved. The curvature can be a reflection of the tibial shape, the femoral shape including during joint motion, and the meniscal shape and combinations thereof.

Wear pattern can be adjusted in any joint and for any type of replacement or resurfacing device. For example, wear patterns in hips, knees, ankles, elbows, shoulders, and spines can be adjusted and/or corrected. Similarly, various types of devices associated with repairs of such joints can be used. For example, a wear pattern in a knee can be adjusted and/or corrected in various types of knee devices, including, without limitation, interpositional devices, uni-compartmental and bi-compartmental resurfacing devices, total resurfacing devices and total knee replacement devices. In cases where multiple contact points or wear patterns are identified in a joint, for example, wear patterns associated with both the medial and lateral femoral condyles in a total knee resurfacing, both can be corrected or improved.

The wear patterns can be adjusted to improve or reduce wear on a new device, such as a hip replacement or a uni-compartmental resurfacing device, to, for example, reduce wear on the device and increase the expected lifetime of the device. Additionally, wear patterns can be adjusted to improve the overall kinematics of the joint, for example, to alter the kinematics to an improved or even ideal case to improve the patient's overall motion in the joint. For example, a device can be designed for a knee joint that functions in a manner that increases wear and degradation of the joint such that the device, when implanted, alters the motion of the joint to a more ideal case with reduced wear and improved functionality.

When an orthopedic device is implanted into a joint, the wear pattern on the articular surface(s) can be altered and controlled. For example, when a unicompartmental knee resurfacing device is implanted in a knee, the wear pattern on the tibial articular surface between the tibia and femur can be changed such that the tibial articular surface functions differently after the implant is in place and the wear pattern at the articular surface is changed when compared to the wear pattern prior to surgery. Unlike existing off-the-shelf implants, which may change the wear pattern simply by virtue of introducing a new geometry into the joint, the wear pattern is changed by design based on the existing geometry and/or kinematics of a particular patient or set or class of patients. This allows the wear pattern to be controlled for that individual patient or for a class or set of patients that exhibit similar characteristic wear patterns, joint geometries and/or joint kinematics. Thus, for example, an improved wear pattern can be designed into a particular orthopedic implant that is specific to a single patient's anatomy, or the wear pattern can be altered based one or more designs from a library of designs that can be applied to one or more patients exhibiting a particular set of characteristics that meet predefined rules or other analyses. Further, the design can be based, at least in part, on the geometry of the joint, on the kinematics of the joint or on a combination thereof.

Figure 11:
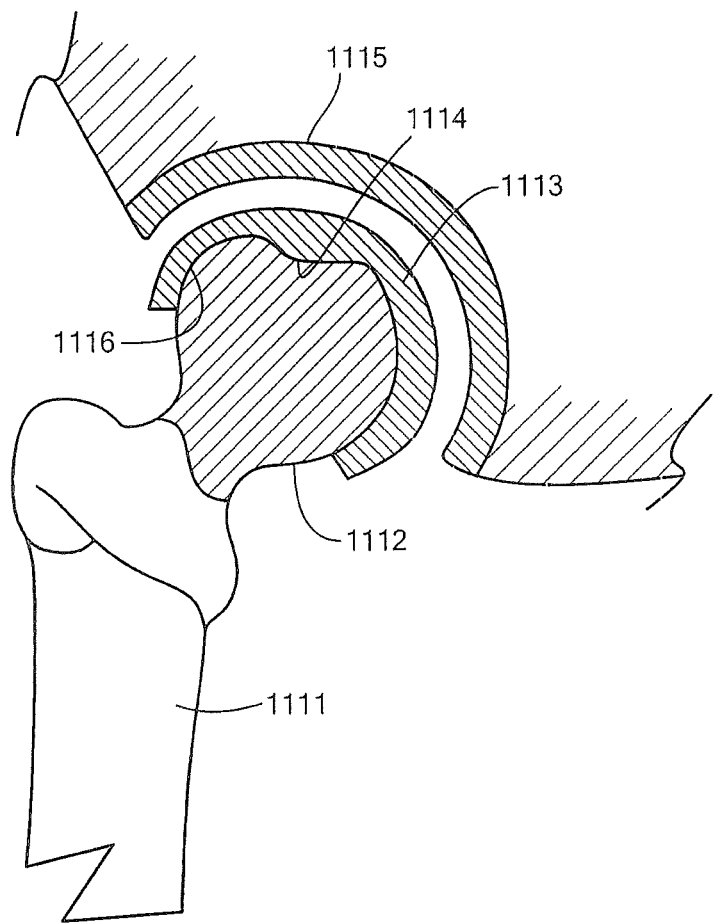
FIG. 11 illustrates in cross-section an embodiment for the hip featuring a wear pattern correcting resurfacing implant for the femoral head.

FIG. 11 illustrates in cross-section an embodiment for the hip featuring a wear pattern correcting resurfacing implant 1113 for a femoral head 1112 of femur 1111. Implant 1113 features an inner surface 1116 which conforms, e.g., in a mirror image fashion, to the surface of femoral head 1112. The outer surface of implant 1113 has a generally spherical curvature which matches that of acetabular component 1115 so as to permit a freedom of joint motion comparable to that of a normal hip joint. Inner surface 1116 features a wear pattern correcting surface 1114 that conforms to a wear pattern on femoral head 1112.

Figure 13:
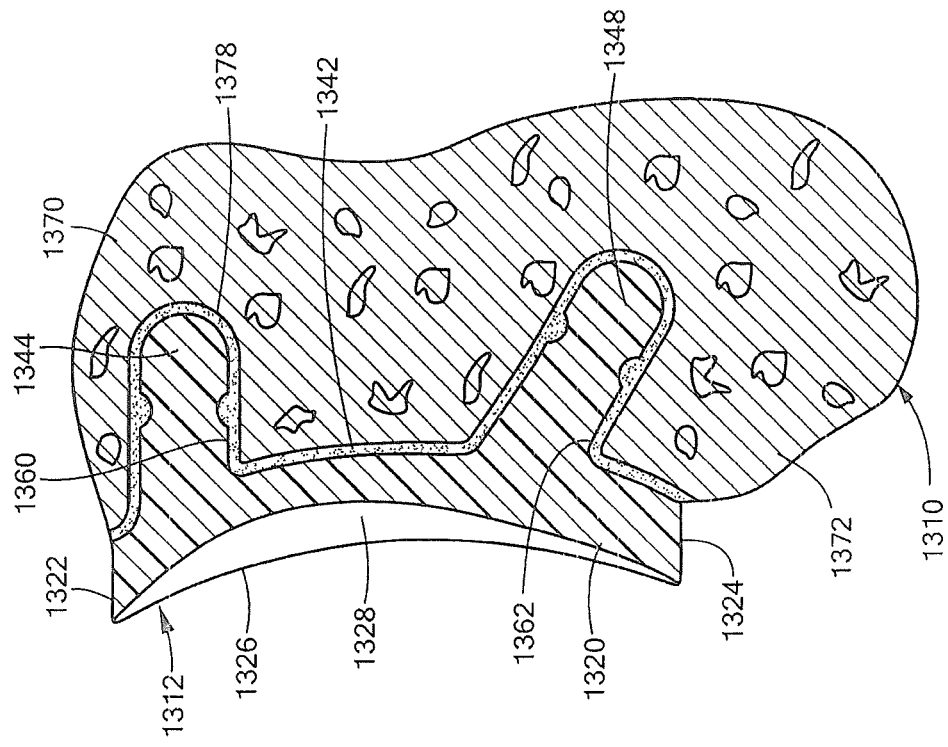
FIG. 13 illustrates a glenoid component embodiment featuring an superior wear pattern correcting surface 1328.
Figure 12:
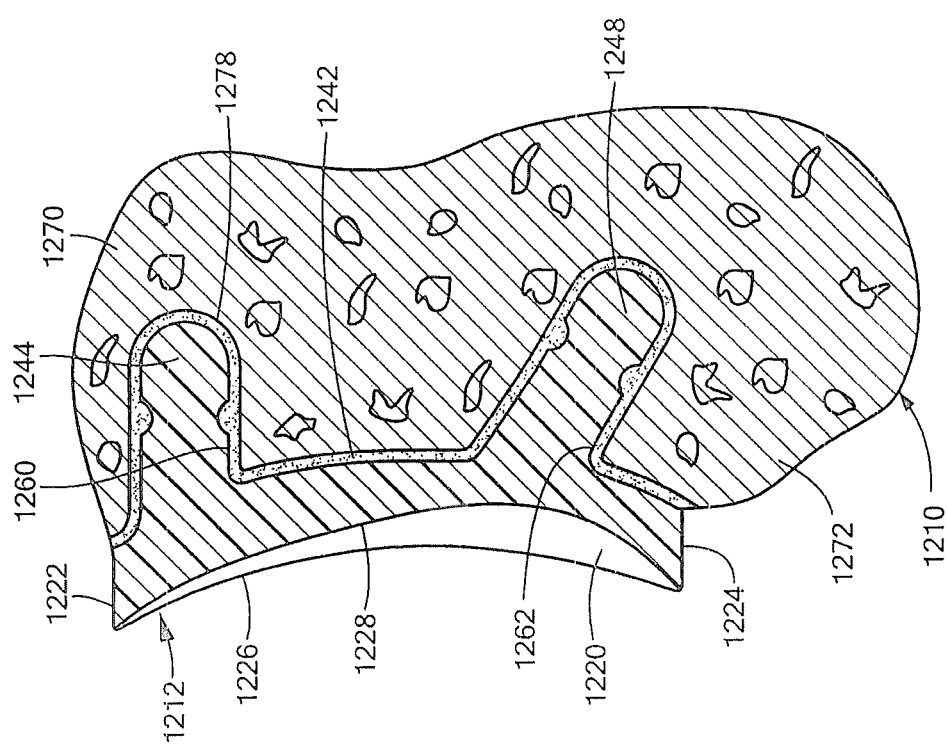
FIG. 12 illustrates a glenoid component embodiment featuring an inferior wear pattern correcting surface 1228.

FIGS. 12 and 13 illustrate in cross sectional view a glenoid member 1220 and 1320. FIGS. 12 and 13 are identical, save for the geometry of the bearing surface as discussed below.) Glenoid member 1220 includes an affixation surface 1242 for affixing the glenoid member 1220 to the scapula 1210. An upper, or superior, affixation peg 1244 projects from the device and is integral with the glenoid member 1220. Peg 1244 fits into hole 1260. A lower, or inferior, affixation peg 1248 also projects from the glenoid member 1220 and is oriented in an offset direction, relative to the superior affixation peg 1244. Peg 1248 fits into hole 1262. The inferior affixation peg 1248 is integral with the glenoid member 1220. Glenoid component 1212 may desirably be constructed in a one-piece member of synthetic polymeric material, e.g., ultra high molecular weight polyethylene (UHMWPE). Cement mantle 1278 affixes the glenoid component 1212 in place in the scapula 1210.

Glenoid component 1212 includes a glenoid member 1220 extending in a superior-inferior direction, that is, in upward and downward directions, between an upper, or superior, edge 1222, and a lower, or inferior, edge 1224. An obverse, or lateral, face 1226 at the front of the glenoid member 1220 has a concave contour configuration and provides bearing means in the form of a concave bearing surface 1228 for receiving a humeral head. An aspect can be seen in FIG. 12, wherein the concavity of bearing surface 1228 has been adjusted inferiorly to match an inferior wear pattern on the humeral head. In FIG. 13, the concavity of bearing surface 1228 has been adjusted superiorly to match a superior wear pattern on the humeral head.

Figure 14:
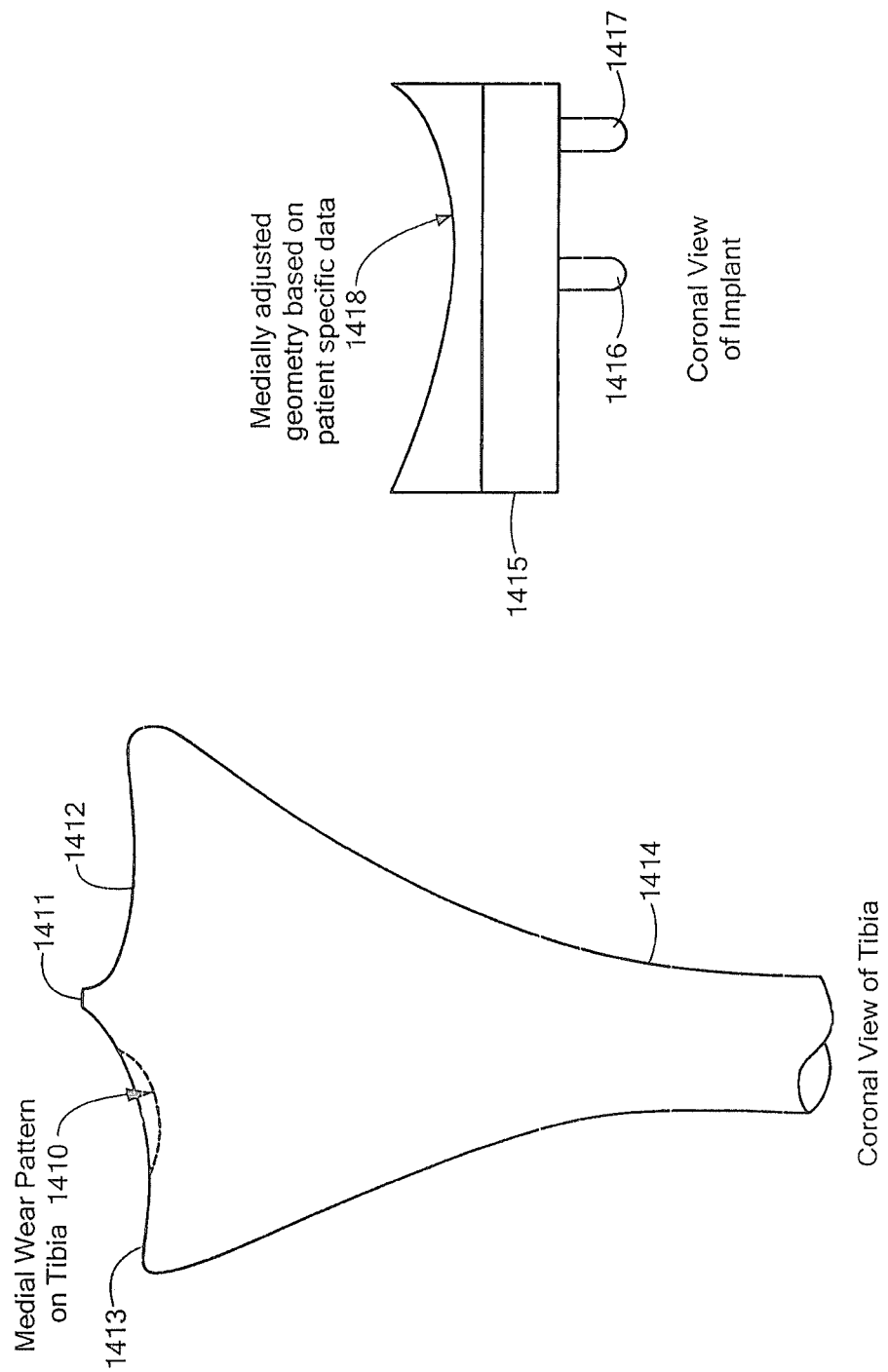
FIGS. 14-16 illustrate, in simplified coronal view, a tibia with medial, lateral and central lateral tibial plateau wear patterns, and a lateral tibial plateau implant featuring a wear pattern correcting surface for each respective type of wear pattern.
Figure 15:
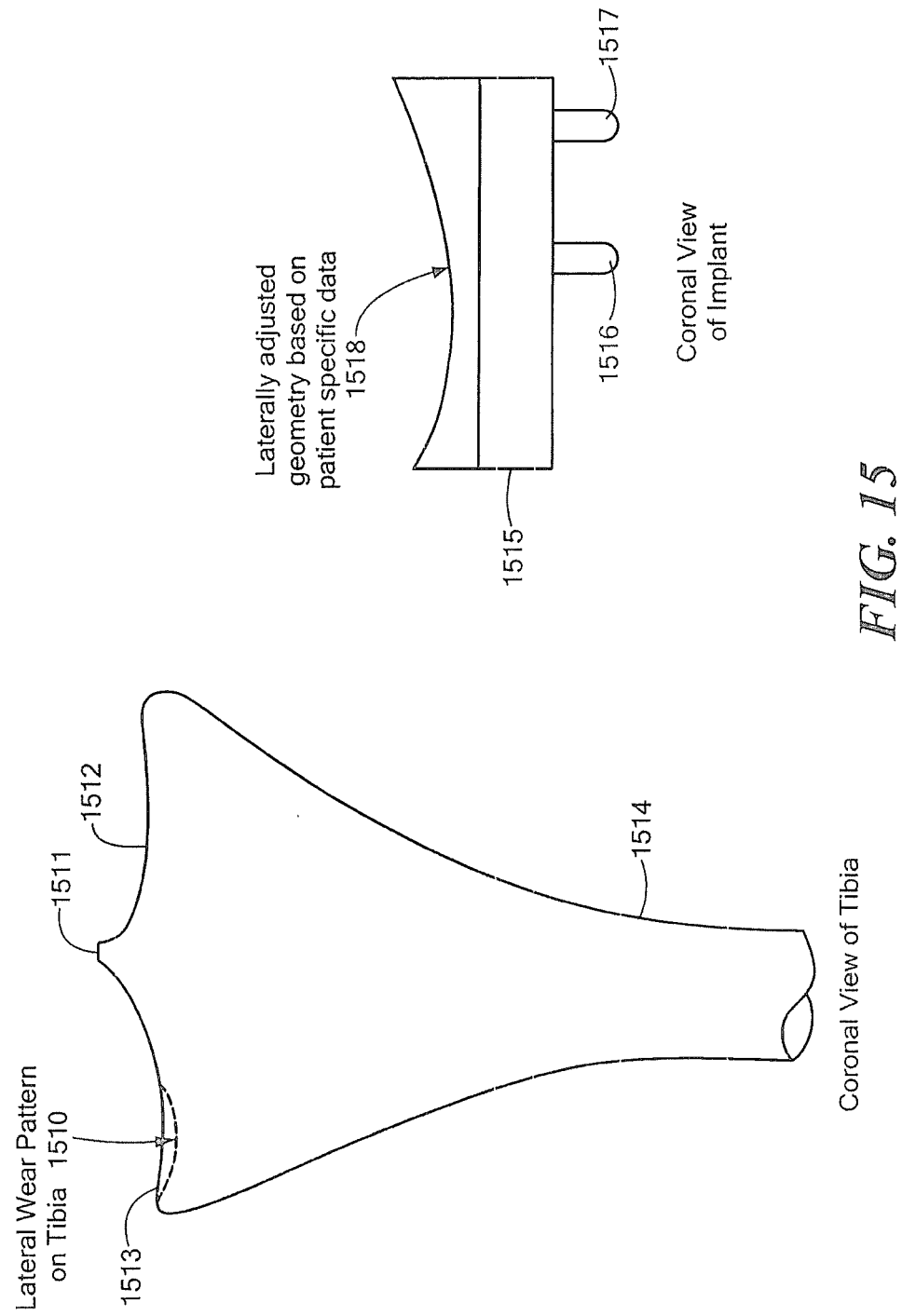
Figure 16:
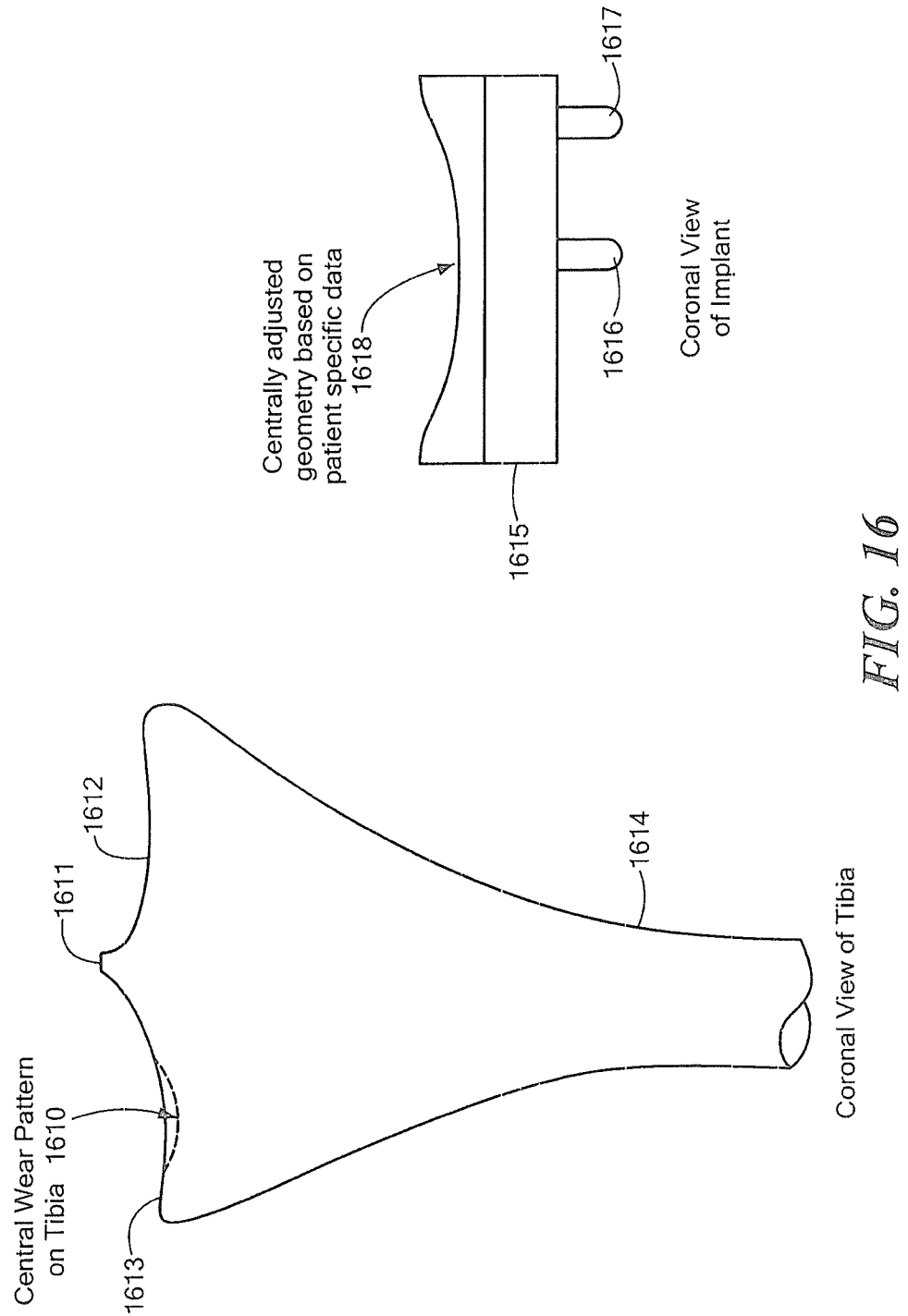

FIGS. 14-16 illustrate, in simplified coronal view, a tibia with medial (FIG. 14), lateral (FIG. 15) and central (FIG. 16) lateral tibial plateau wear patterns, and a lateral tibial plateau implant featuring a wear pattern correcting bearing surface for each respective type of wear pattern. Tibia 1414 includes lateral tibial plateau 1413, medial tibial plateau 1412, and tibial spine 1411. A medial wear pattern 1410 can be seen in the lateral tibial plateau 1413. Device 1415 is an implant having a bearing surface 1418 based on patient-specific information and desirably derived from imaging data as described herein. In device 1415, the concavity of bearing surface 1418 is adjusted medially to account for, and adapt to, the wear characteristics of this particular patient. Device 1415 also features integral keel 1416 and pegs 1417 (which are better seen in FIGS. 17-19.)

In FIG. 15, a lateral wear pattern 1510 can be seen in the lateral tibial plateau 1513. Device 1515 is an implant having a bearing surface 1518 based on patient-specific information and desirably derived from imaging data as described herein. In device 1515, the concavity of bearing surface 1518 is adjusted laterally to account for, and adapt to, the wear characteristics of this particular patient.

In FIG. 16, a central wear pattern 1610 can be seen in the lateral tibial plateau 1613. Device 1615 is an implant having a bearing surface 1618 based on patient-specific information and desirably derived from imaging data as described herein. In device 1615, the concavity of bearing surface 1618 is adjusted centrally to account for, and adapt to, the wear characteristics of this particular patient.

Figure 17:
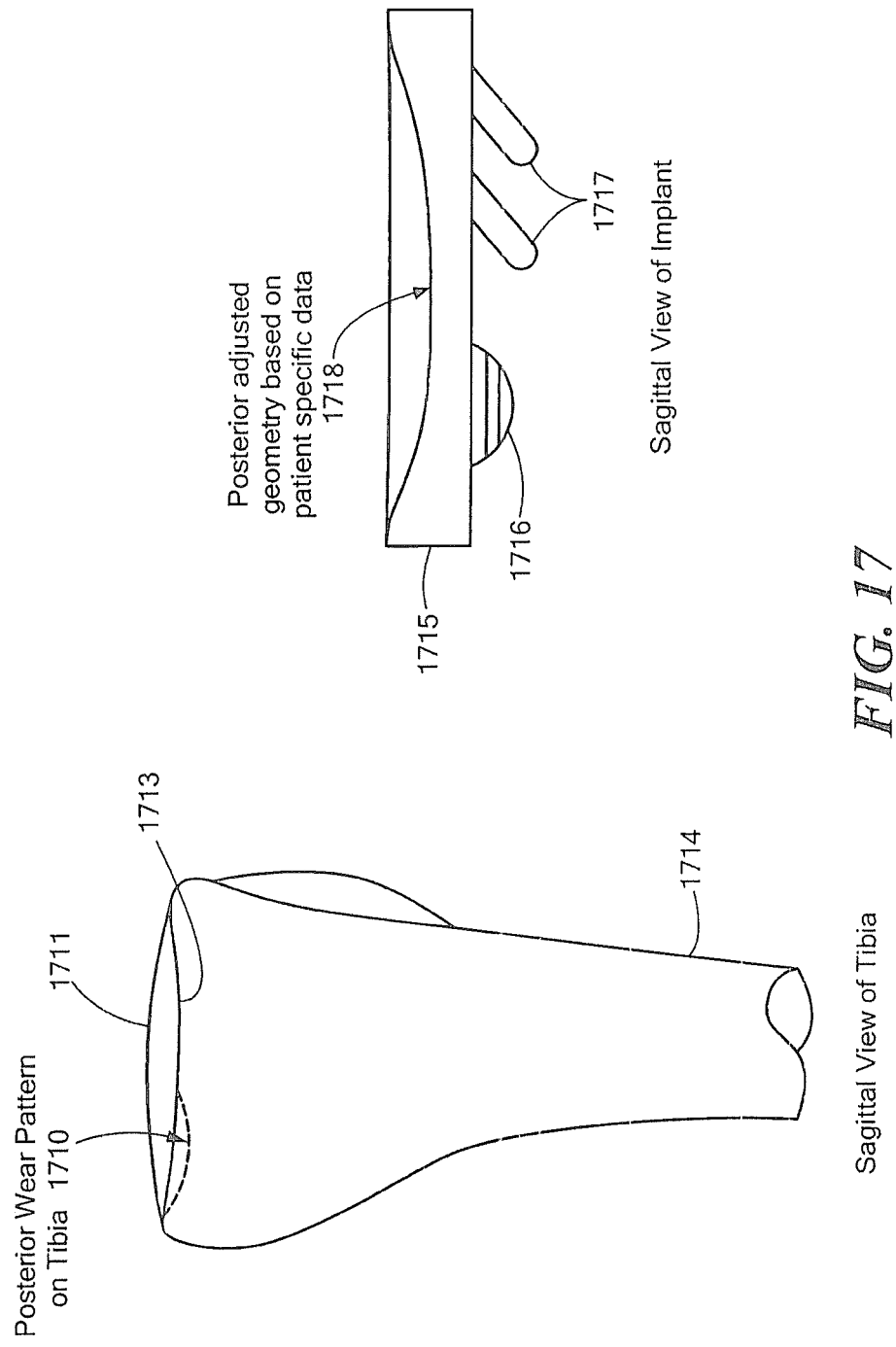
Figure 18:
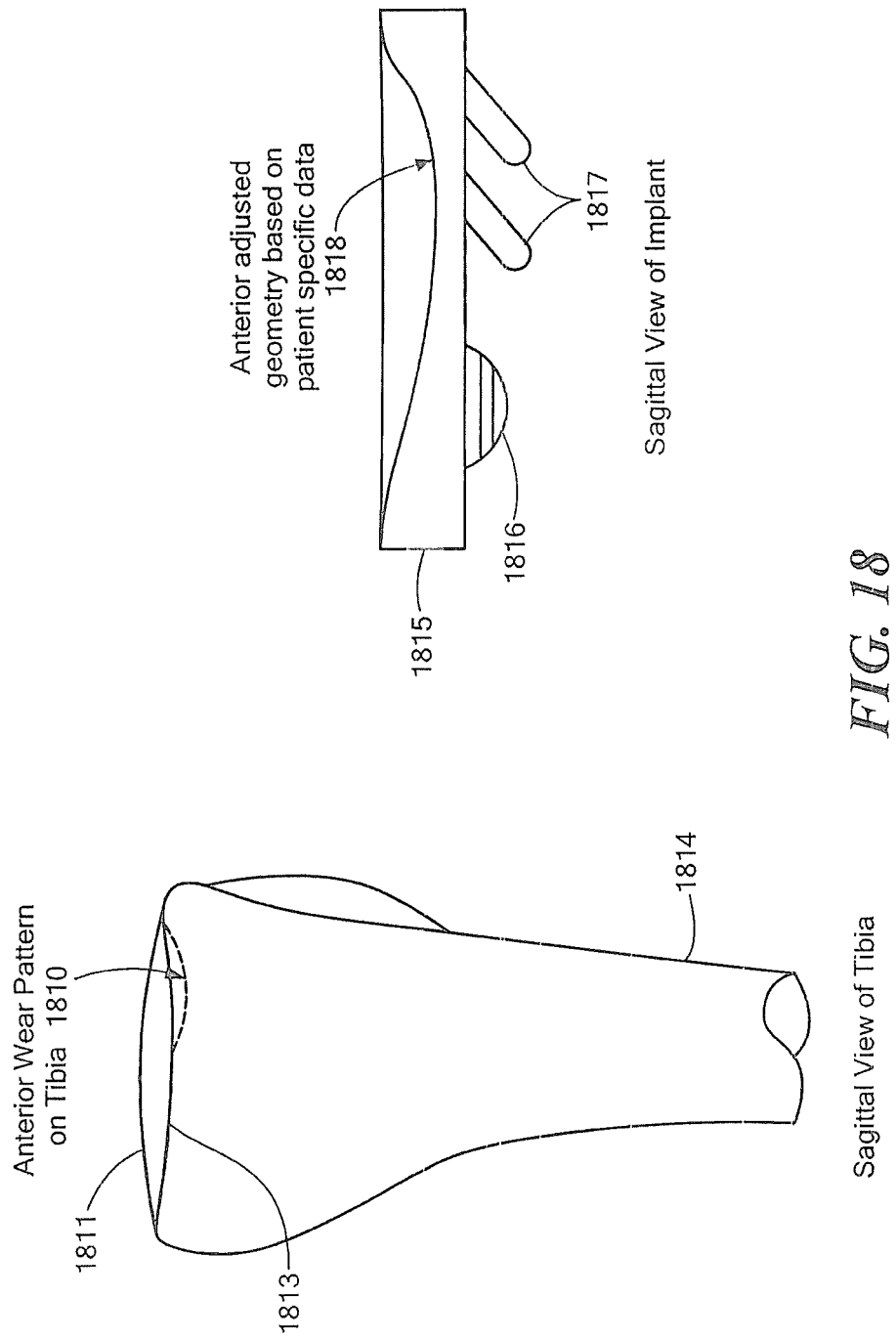

FIGS. 17-19 illustrate, in simplified sagittal view, a tibia with posterior (FIG. 17), anterior (FIG. 18) and central (FIG. 19) lateral tibial plateau wear patterns, and a lateral tibial plateau implant featuring a wear pattern correcting bearing surface for each respective type of wear pattern. Tibia 1714 includes lateral tibial plateau 1713, and tibial spine 1711. A posterior wear pattern 1710 can be seen in the lateral tibial plateau 1713. Device 1715 is an implant having a bearing surface 1718 based on patient-specific information and desirably derived from imaging data as described herein. In device 1715, the concavity of bearing surface 1718 is adjusted posteriorly to account for, and adapt to, the wear characteristics of this particular patient. Device 1715 also features integral keel 1716 and pegs 1717.

In FIG. 18, an anterior wear pattern 1810 can be seen in the lateral tibial plateau 1813. Device 1815 is an implant having a bearing surface 1818 based on patient-specific information and desirably derived from imaging data as described herein. In device 1815, the concavity of bearing surface 1818 is adjusted anteriorly to account for, and adapt to, the wear characteristics of this particular patient.

In FIG. 19, a central wear pattern 1910 can be seen in the lateral tibial plateau 1913. Device 1915 is an implant having a bearing surface 1918 based on patient-specific information and desirably derived from imaging data as described herein. In device 1915, the concavity of bearing surface 1918 is adjusted centrally to account for, and adapt to, the wear characteristics of this particular patient.

In the above embodiments, if desirable, the width of the concavity, e.g., in the tibial and glenoid components, may be widened to provide a less constraining arrangement if the wear pattern is wide. Alternately, if desirable, the width of the concavity, e.g., in the tibial and glenoid components, may be narrowed to provide a more constraining arrangement if wear pattern is narrow.

Various components and combinations of components can be used in devices that correct or adjust wear patters. Examples of single-component systems include plastics, polymers, metals, metal alloys, crystal free metals, biologic materials, or combinations thereof. In certain embodiments, the surface of the repair system facing the underlying bone can be smooth. In other embodiments, the surface of the repair system facing the underlying bone can be porous or porous-coated. In another aspect, the surface of the repair system facing the underlying bone is designed with one or more grooves, for example to facilitate the in-growth of the surrounding tissue. The external surface of the device can have a step-like design, which can be advantageous for altering biomechanical stresses. Optionally, flanges can also be added at one or more positions on the device (e.g., to prevent the repair system from rotating, to control toggle and/or prevent settling into the marrow cavity). The flanges can be part of a conical or a cylindrical design. A portion or all of the repair system facing the underlying bone can also be flat which can help to control depth of the implant and to prevent toggle.

Examples of multiple-component systems include combinations of metals, plastics, metal alloys, crystal free metals, and biological materials. One or more components of the articular surface repair system can be composed of a biologic material (e.g., a tissue scaffold with cells such as cartilage cells or stem cells alone or seeded within a substrate such as a bioresorbable material or a tissue scaffold, allograft, autograft or combinations thereof) and/or a non-biological material (e.g., polyethylene or a chromium alloy such as chromium cobalt).

Thus, the repair system can include one or more areas of a single material or a combination of materials, for example, the articular surface repair system can have a first and a second component. The first component is typically designed to have size, thickness and curvature similar to that of the cartilage tissue lost while the second component is typically designed to have a curvature similar to the subchondral bone. In addition, the first component can have biomechanical properties similar to articular cartilage, including but not limited to similar elasticity and resistance to axial loading or shear forces. The first and the second component can consist of two different metals or metal alloys. One or more components of the system (e.g., the second portion) can be composed of a biologic material including bone or a non-biologic material, e.g., hydroxyapatite, tantalum, chromium alloys, chromium cobalt or other metal alloys.

One or more regions of the articular surface repair system (e.g., the outer margin of the first portion and/or the second portion) can be bioresorbable, for example to allow the interface between the articular surface repair system and the patient's normal cartilage, over time, to be filled in with hyaline or fibrocartilage. Similarly, one or more regions (e.g., the outer margin of the first portion of the articular surface repair system and/or the second portion) can be porous. The degree of porosity can change throughout the porous region, linearly or non-linearly, for where the degree of porosity will typically decrease towards the center of the articular surface repair system. The pores can be designed for in-growth of cartilage cells, cartilage matrix, and connective tissue thereby achieving a smooth interface between the articular surface repair system and the surrounding cartilage.

The repair system (e.g., the second component in multiple component systems) can be attached to the patient's bone with use of a cement-like material such as methylmethacrylate, injectable hydroxy- or calcium-apatite materials and the like.

In certain embodiments, one or more portions of the articular surface repair system can be pliable or liquid or deformable at the time of implantation and can harden later. Hardening can occur, for example, within 1 second to 2 hours (or any time period therebetween), preferably with in 1 second to 30 minutes (or any time period therebetween), more preferably between 1 second and 10 minutes (or any time period there between).

One or more components of the articular surface repair system can be adapted to receive injections. For example, the external surface of the articular surface repair system can have one or more openings therein. The openings can be sized to receive screws, tubing, needles or other devices which can be inserted and advanced to the desired depth, for example, through the articular surface repair system into the marrow space. Injectables such as methylmethacrylate and injectable hydroxy- or calcium-apatite materials can then be introduced through the opening (or tubing inserted therethrough) into the marrow space thereby bonding the articular surface repair system with the marrow space. Similarly, screws or pins, or other anchoring mechanisms can be inserted into the openings and advanced to the underlying subchondral bone and the bone marrow or epiphysis to achieve fixation of the articular surface repair system to the bone. Portions or all components of the screw or pin can be bioresorbable, for example, the distal portion of a screw that protrudes into the marrow space can be bioresorbable. During the initial period after the surgery, the screw can provide the primary fixation of the articular surface repair system. Subsequently, ingrowth of bone into a porous-coated area along the undersurface of the articular cartilage repair system can take over as the primary stabilizer of the articular surface repair system against the bone.

The articular surface repair system can be anchored to the patient's bone with use of a pin or screw or other attachment mechanism. The attachment mechanism can be bioresorbable. The screw or pin or attachment mechanism can be inserted and advanced towards the articular surface repair system from a non-cartilage covered portion of the bone or from a non-weight-bearing surface of the joint.

The interface between the articular surface repair system and the surrounding normal cartilage can be at an angle, for example oriented at an angle of 90 degrees relative to the underlying subchondral bone. Suitable angles can be determined in view of the teachings herein, and in certain cases, non-90 degree angles can have advantages with regard to load distribution along the interface between the articular surface repair system and the surrounding normal cartilage.

The interface between the articular surface repair system and the surrounding normal cartilage and/or bone can be covered with a pharmaceutical or bioactive agent, for example a material that stimulates the biological integration of the repair system into the normal cartilage and/or bone. The surface area of the interface can be irregular, for example, to increase exposure of the interface to pharmaceutical or bioactive agents.

D. Pre-Existing Repair Systems

As described herein, repair systems of various sizes, curvatures and thicknesses can be obtained. These repair systems can be catalogued and stored to create a library of systems from which an appropriate system for an individual patient can then be selected. In other words, a defect, or an articular surface, is assessed in a particular subject and a pre-existing repair system having a suitable shape and size is selected from the library for further manipulation (e.g., shaping) and implantation.

E. Mini-Prosthesis

The methods and compositions described herein can be used to replace only a portion of the articular surface, for example, an area of diseased cartilage or lost cartilage on the articular surface. In these systems, the articular surface repair system can be designed to replace only the area of diseased or lost cartilage or it can extend beyond the area of diseased or lost cartilage, e.g., 3 or 5 mm into normal adjacent cartilage. In certain embodiments, the prosthesis replaces less than about 70% to 80% (or any value therebetween) of the articular surface (e.g., any given articular surface such as a single femoral condyle, etc.), preferably, less than about 50% to 70% (or any value therebetween), more preferably, less than about 30% to 50% (or any value therebetween), more preferably less than about 20% to 30% (or any value therebetween), even more preferably less than about 20% of the articular surface.

The prosthesis can include multiple components, for example a component that is implanted into the bone (e.g., a metallic device) attached to a component that is shaped to cover the defect of the cartilage overlaying the bone. Additional components, for example intermediate plates, meniscal repair systems and the like can also be included. It is contemplated that each component replaces less than all of the corresponding articular surface. However, each component need not replace the same portion of the articular surface. In other words, the prosthesis can have a bone-implanted component that replaces less than 30% of the bone and a cartilage component that replaces 60% of the cartilage. The prosthesis can include any combination, provided each component replaces less than the entire articular surface.

The articular surface repair system can be formed or selected so that it will achieve a near anatomic fit or match with the surrounding or adjacent cartilage or bone. Typically, the articular surface repair system is formed and/or selected so that its outer margin located at the external surface will be aligned with the surrounding or adjacent cartilage.

Thus, the articular repair system can be designed to replace the weight-bearing portion (or more or less than the weight bearing portion) of an articular surface, for example in a femoral condyle. The weight-bearing surface refers to the contact area between two opposing articular surfaces during activities of normal daily living (e.g., normal gait). At least one or more weight-bearing portions can be replaced in this manner, e.g., on a femoral condyle and on a tibia.

In other embodiments, an area of diseased cartilage or cartilage loss can be identified in a weight-bearing area and only a portion of the weight-bearing area, specifically the portion containing the diseased cartilage or area of cartilage loss, can be replaced with an articular surface repair system.

In another embodiment, the articular repair system can be designed or selected to replace substantially the entire articular surface, e.g., a condyle.

In another embodiment, for example, in patients with diffuse cartilage loss, the articular repair system can be designed to replace an area slightly larger than the weight-bearing surface.

In certain aspects, the defect to be repaired is located only on one articular surface, typically the most diseased surface. For example, in a patient with severe cartilage loss in the medial femoral condyle but less severe disease in the tibia, the articular surface repair system can only be applied to the medial femoral condyle. Preferably, in any methods described herein, the articular surface repair system is designed to achieve an exact or a near anatomic fit with the adjacent normal cartilage.

In other embodiments, more than one articular surface can be repaired. The area(s) of repair will be typically limited to areas of diseased cartilage or cartilage loss or areas slightly greater than the area of diseased cartilage or cartilage loss within the weight-bearing surface(s).

In another embodiment, one or more components of the articular surface repair (e.g., the surface of the system that is pointing towards the underlying bone or bone marrow) can be porous or porous-coated. A variety of different porous metal coatings have been proposed for enhancing fixation of a metallic prosthesis by bone tissue in-growth. Thus, for example, U.S. Pat. No. 3,855,638, discloses a surgical prosthetic device, which can be used as a bone prosthesis, comprising a composite structure consisting of a solid metallic material substrate and a porous coating of the same solid metallic material adhered to and extending over at least a portion of the surface of the substrate. The porous coating consists of a plurality of small discrete particles of metallic material bonded together at their points of contact with each other to define a plurality of connected interstitial pores in the coating. The size and spacing of the particles, which can be distributed in a plurality of monolayers, can be such that the average interstitial pore size is not more than about 200 microns. Additionally, the pore size distribution can be substantially uniform from the substrate-coating interface to the surface of the coating. In another embodiment, the articular surface repair system can contain one or more polymeric materials that can be loaded with and release therapeutic agents including drugs or other pharmacological treatments that can be used for drug delivery. The polymeric materials can, for example, be placed inside areas of porous coating. The polymeric materials can be used to release therapeutic drugs, e.g., bone or cartilage growth stimulating drugs. This embodiment can be combined with other embodiments, wherein portions of the articular surface repair system can be bioresorbable. For example, the first layer of an articular surface repair system or portions of its first layer can be bioresorbable. As the first layer gets increasingly resorbed, local release of a cartilage growth-stimulating drug can facilitate in-growth of cartilage cells and matrix formation.

In any of the methods or compositions described herein, the articular surface repair system can be pre-manufactured with a range of sizes, curvatures and thicknesses. Alternatively, the articular surface repair system can be custom-made for an individual patient.

IV. Manufacturing

A. Shaping

In certain instances shaping of the repair material will be required before or after formation (e.g., growth to desired thickness), for example where the thickness of the required cartilage material is not uniform (e.g., where different sections of the cartilage replacement or regenerating material require different thicknesses).

The replacement material can be shaped by any suitable technique including, but not limited to, casting techniques, mechanical abrasion, laser abrasion or ablation, radiofrequency treatment, cryoablation, variations in exposure time and concentration of nutrients, enzymes or growth factors and any other means suitable for influencing or changing cartilage thickness. See, e.g., WO 00/15153. If enzymatic digestion is used, certain sections of the cartilage replacement or regenerating material can be exposed to higher doses of the enzyme or can be exposed longer as a means of achieving different thicknesses and curvatures of the cartilage replacement or regenerating material in different sections of said material.

The material can be shaped manually and/or automatically, for example using a device into which a pre-selected thickness and/or curvature has been input and then programming the device using the input information to achieve the desired shape.

In addition to, or instead of, shaping the cartilage repair material, the site of implantation (e.g., bone surface, any cartilage material remaining, etc.) can also be shaped by any suitable technique in order to enhance integration of the repair material.

B. Sizing

The articular repair system can be formed or selected so that it will achieve a near anatomic fit or match with the surrounding or adjacent cartilage, subchondral bone, menisci and/or other tissue. The shape of the repair system can be based on an imaging analysis. If the articular repair system is intended to replace an area of diseased cartilage or lost cartilage, the near anatomic fit can be achieved using a method that provides a virtual reconstruction of the shape of healthy cartilage in an electronic image or reflect or conform to a wear pattern. An imaging analysis may include conventional and digital imaging techniques known in the art, including x-ray imaging and processing; fluoroscopy; digital tomosynthesis; ultrasound including A-scan, B-scan and C-scan; optical coherence, conventional, cone beam, or spiral computed tomography (CT); single photon emission tomography (SPECT); bone scan; positron emission tomography (PET); magnetic resonance imaging (MRI); thermal imaging; and optical imaging, or a combination thereof. Such techniques are explained fully in the literature and need not be described herein. See, e.g., *X-Ray Structure Determination: A Practical Guide,* 2nd Ed., Stout et al., eds. Wiley & Sons, 1989; *Body CT: A Practical Approach,* Slone, ed., McGraw-Hill 1999; *X-ray Diagnosis: A Physician's Approach,* Lam, ed., Springer-Verlag 1998; *Dental Radiology: Understanding the X-Ray Image,* Brocklebank, ed., Oxford University Press 1997; and *The Essential Physics of Medical Imaging* ($2^{nd}$ Ed.), Bushberg et al.

In one embodiment, a near normal cartilage surface at the position of the cartilage defect can be reconstructed by interpolating the healthy cartilage surface across the cartilage defect or area of diseased cartilage. This can, for example, be achieved by describing the healthy cartilage by means of a parametric surface (e.g., a B-spline surface), for which the control points are placed such that the parametric surface follows the contour of the healthy cartilage and bridges the cartilage defect or area of diseased cartilage. The continuity properties of the parametric surface will provide a smooth integration of the part that bridges the cartilage defect or area of diseased cartilage with the contour of the surrounding healthy cartilage. The part of the parametric surface over the area of the cartilage defect or area of diseased cartilage can be used to determine the shape or part of the shape of the articular repair system to match with the surrounding cartilage.

In another embodiment, a near normal cartilage surface at the position of the cartilage defect or area of diseased cartilage can be reconstructed using morphological image processing. In a first step, the cartilage can be extracted from the electronic image using manual, semi-automated and/or automated segmentation techniques (e.g., manual tracing, region growing, live wire, model-based segmentation), resulting in a binary image. Defects in the cartilage appear as indentations that can be filled with a morphological closing operation performed in 2-D or 3-D with an appropriately selected structuring element. The closing operation is typically defined as a dilation followed by an erosion. A dilation operator sets the current pixel in the output image to 1 if at least one pixel of the structuring element lies inside a region in the source image. An erosion operator sets the current pixel in the output image to 1 if the whole structuring element lies inside a region in the source image. The filling of the cartilage defect or area of diseased cartilage creates a new surface over the area of the cartilage defect or area of diseased cartilage that can be used to determine the shape or part of the shape of the articular repair system to match with the surrounding cartilage or subchondral bone.

As described above, the articular repair system can be formed or selected from a library or database of systems of various sizes, curvatures and thicknesses so that it will achieve a near anatomic fit or match with the surrounding or adjacent cartilage and/or subchondral bone. These systems can be pre-made or made to order for an individual patient. In order to control the fit or match of the articular repair system with the surrounding or adjacent cartilage or subchondral bone or menisci and other tissues preoperatively, a software program can be used that projects the articular repair system over the anatomic position where it will be implanted. Suitable software is commercially available and/or readily modified or designed by a skilled programmer.

In yet another embodiment, the articular surface repair system can be projected over the implantation site using one or more 3-D images. The cartilage and/or subchondral bone and other anatomic structures are extracted from a 3-D electronic image such as an MRI or a CT using manual, semi-automated and/or automated segmentation techniques. A 3-D representation of the cartilage and/or subchondral bone and other anatomic structures as well as the articular repair system is generated, for example using a polygon or NURBS surface or other parametric surface representation. For a description of various parametric surface representations see, for example Foley, J. D. et al., Computer Graphics: Principles and Practice in C; Addison-Wesley, $2^{nd}$ edition, 1995).

The 3-D representations of the cartilage and/or subchondral bone and other anatomic structures and the articular repair system can be merged into a common coordinate system. The articular repair system can then be placed at the desired implantation site. The representations of the cartilage, subchondral bone, menisci and other anatomic structures and the articular repair system are rendered into a 3-D image, for example application programming interfaces (APIs) OpenGL® (standard library of advanced 3-D graphics functions developed by SGI, Inc.; available as part of the drivers for PC-based video cards, for example from www.nvidia.com for NVIDIA video cards orati.amd.com for ATI/AMD products) or DirectX® (multimedia API for Microsoft Windows® based PC systems; available from www.microsoft.com). The 3-D image can be rendered showing the cartilage, subchondral bone, menisci or other anatomic objects, and the articular repair system from varying angles, e.g., by rotating or moving them interactively or non-interactively, in real-time or non-real-time.

The software can be designed so that the articular repair system, including surgical tools and instruments with the best fit relative to the cartilage and/or subchondral bone is automatically selected, for example using some of the techniques described above. Alternatively, the operator can select an articular repair system, including surgical tools and instruments and project it or drag it onto the implantation site using suitable tools and techniques. The operator can move and rotate the articular repair systems in three dimensions relative to the implantation site and can perform a visual inspection of the fit between the articular repair system and the implantation site. The visual inspection can be computer assisted. The procedure can be repeated until a satisfactory fit has been achieved. The procedure can be performed manually by the operator; or it can be computer-assisted in whole or part. For example, the software can select a first trial implant that the operator can test. The operator can evaluate the fit. The software can be designed and used to highlight areas of poor alignment between the implant and the surrounding cartilage or subchondral bone or menisci or other tissues. Based on this information, the software or the operator can then select another implant and test its alignment. One of skill in the art will readily be able to select, modify and/or create suitable computer programs for the purposes described herein.

In another embodiment, the implantation site can be visualized using one or more cross-sectional 2-D images. Typically, a series of 2-D cross-sectional images will be used. The articular repair system can then be superimposed onto one or more of these 2-D images. The 2-D cross-sectional images can be reconstructed in other planes, e.g., from sagittal to coronal, etc. Isotropic data sets (e.g., data sets where the slice thickness is the same or nearly the same as the in-plane resolution) or near isotropic data sets can also be used. Multiple planes can be displayed simultaneously, for example using a split screen display. The operator can also scroll through the 2-D images in any desired orientation in real time or near real time; the operator can rotate the imaged tissue volume while doing this. The articular repair system can be displayed in cross-section utilizing different display planes, e.g., sagittal, coronal or axial, typically matching those of the 2-D images demonstrating the cartilage, subchondral bone, menisci or other tissue. Alternatively, a three-dimensional display can be used for the articular repair system. The 2-D electronic image and the 2-D or 3-D representation of the articular repair system can be merged into a common coordinate system. The articular repair system can then be placed at the desired implantation site. The series of 2-D cross-sections of the anatomic structures, the implantation site and the articular repair system can be displayed interactively (e.g., the operator can scroll through a series of slices) or non-interactively (e.g., as an animation that moves through the series of slices), in real-time or non-real-time.

C. Rapid Prototyping

Rapid prototyping is a technique for fabricating a three-dimensional object from a computer model of the object. A special printer is used to fabricate the prototype from a plurality of two-dimensional layers. Computer software sections the representations of the object into a plurality of distinct two-dimensional layers and then a three-dimensional printer fabricates a layer of material for each layer sectioned by the software. Together the various fabricated layers form the desired prototype. More information about rapid prototyping techniques is available in U.S. Publication No. 2002/0079601A1. An advantage to using rapid prototyping is that it enables the use of free form fabrication techniques that use toxic or potent compounds safely. These compounds can be safely incorporated in an excipient envelope, which reduces worker exposure A powder piston and build bed are provided. Powder includes any material (metal, plastic, etc.) that can be made into a powder or bonded with a liquid. The power is rolled from a feeder source with a spreader onto a surface of a bed. The thickness of the layer is controlled by the computer. The print head then deposits a binder fluid onto the powder layer at a location where it is desired that the powder bind. Powder is again rolled into the build bed and the process is repeated, with the binding fluid deposition being controlled at each layer to correspond to the three-dimensional location of the device formation. For a further discussion of this process see, e.g., U.S. Patent Publication No. 2003/017365A1.

The rapid prototyping can use the two dimensional images obtained, as described above, to determine each of the two-dimensional shapes for each of the layers of the prototyping machine. In this scenario, each two dimensional image slice would correspond to a two-dimensional prototype slide. Alternatively, the three-dimensional shape of the defect can be determined, as described above, and then broken down into two dimensional slices for the rapid prototyping process. The advantage of using the three-dimensional model is that the two-dimensional slices used for the rapid prototyping machine can be along the same plane as the two-dimensional images taken or along a different plane altogether.

Rapid prototyping can be combined or used in conjunction with casting techniques. For example, a shell or container with inner dimensions corresponding to an articular repair system can be made using rapid prototyping. Plastic or wax-like materials are typically used for this purpose. The inside of the container can subsequently be coated, for example with a ceramic, for subsequent casting. Using this process, personalized casts can be generated.

Rapid prototyping can be used for producing articular repair systems. Rapid prototyping can be performed at a manufacturing facility. Alternatively, it may be performed in the operating room after an intraoperative measurement has been performed.

Wear pattern-specific implant shapes or geometries can be achieved using a number of different manufacturing techniques known in the art, including polishing, milling, machining, casting, rapid protocasting, laser sintering, laser melting and electro abrasion. In one embodiment, the wear pattern-adapted articular surface may be formed de novo. In another embodiment, the wear pattern-adapted articular surface may be formed by processing an implant with a standard shape of the articular surface (a "blank") and adapting the shape for the particular wear pattern, e.g., using machining or electroabrasion.

V. Surgical Techniques

Prior to performing surgery on a patient, the surgeon can preoperatively make a determination of the alignment of the knee using, for example, an erect AP x-ray. In performing preoperative assessment any lateral and patella spurs that are present can be identified.

Using standard surgical techniques, the patient is anesthetized and an incision is made in order to provide access to the portion or portions of the knee joint to be repaired. A medial portal can be used initially to enable arthroscopy of the joint. Thereafter, the medial portal can be incorporated into the operative incision and/or standard lateral portals can be used.

Once an appropriate incision has been made, the exposed compartment is inspected for integrity, including the integrity of the ligament structures. If necessary, portions of the meniscus can be removed as well as any spurs or osteophytes that were identified in the AP x-ray or that may be present within the joint. In order to facilitate removal of osteophytes, the surgeon may flex the knee to gain exposure to additional medial and medial-posterior osteophytes. Additionally, osteophytes can be removed from the patella during this process. If necessary, the medial and/or lateral meniscus can also be removed at this point, if desired, along with the rim of the meniscus.

As would be appreciated by those of skill in the art, evaluation of the medial cruciate ligament may be required to facilitate tibial osteophyte removal.

Once the joint surfaces have been prepared, the desired implants can be inserted into the joint.

A. Tibial Plateau

To insert the device 200 of FIG. 2 into the medial compartment, a mini-incision arthrotomy medial to the patella tendon is made. Once the incision is made, the medial condyle is exposed and a medial sleeve is prepared to about 1 cm below the joint line using a suitable knife and curved osteotome. After preparing the medial sleeve, a Z-retractor is placed around the medial tibial plateau and anterior portions of the meniscus and the osteophytes along the tibia and femur are removed. At this point, the knee should be flexed to about 60° or more. The Z-retractor is removed and the implant is placed against the most distal aspect of the femur and over the tibial plateau edge. The implant should be pushed straight back. In some instances, application of valgus stress may ease insertion of the implant.

To insert the device of FIG. 2 into the lateral compartment a mini-incision arthrotomy is performed lateral to the patella tendon. Once the incision is made, the lateral condyle is exposed and a lateral sleeve is prepared to about 1 cm below the joint line using a suitable knife and curved osteotome. After preparing the lateral sleeve, a Z-retractor is placed around the lateral tibial plateau and anterior portions of the meniscus and the osteophytes along the tibia and femur are removed. The Z-retractor is removed and the implant is placed against the distal aspect of the femur and over the tibial plateau edge. The implant is held at a 45° angle and rotated against the lateral condyle using a lateral to medial push toward the lateral spine. In some instances, application of varus stress may ease insertion of the implant.

Once any implant shown in FIG. 2 is implanted, the device should be positioned within 0 to 2 mm of the AP boundaries of the tibial plateau and superimposed over the boundary. Verification of the range of motion should then be performed to confirm that there is minimal translation of the implant. Once positioning is confirmed, closure of the wound is performed using techniques known in the art.

As will be appreciated, additional treatment of the surface of the tibial plateau may be desirable, depending on the configuration of the implant 200. For example, one or more channels or grooves may be formed on the surface of the tibial plateau to accommodate anchoring mechanisms such as the keel 212 shown in FIG. 2K or the translational movement cross-members 222, 221 shown in FIGS. 2M-N.

B. Condylar Repair Systems

To insert the device 300 shown in FIG. 3, depending on the condyle to be repaired either an antero-medial or antero-lateral skin incision is made which begins approximately 1 cm proximal to the superior border of the patella. The incision typically can range from, for example, 6-10 cm along the edge of the patella. As will be appreciated, a longer incision may be required under some circumstances.

It may be required to excise excess deep synovium to improve access to the joint. Additionally, all or part of the fat pad may also be excused and to enable inspection of the opposite joint compartment. Typically, osteophytes are removed from the entire medial and/or lateral edge of the femur and the tibia as well as any osteophytes on the edge of the patella that might be significant.

Although it is possible, typically the devices 300 do not require resection of the distal femur prior to implanting the device. However, if desired, bone cuts can be performed to provide a surface for the implant.

At this juncture, the patient's leg is placed in 90° flexion position. A guide can then be placed on the condyle which covers the distal femoral cartilage. The guide enables the surgeon to determine placement of apertures that enable the implant 300 to be accurately placed on the condyle. With the guide in place, holes are drilled into the condyle to create apertures from 1-3 mm in depth. Once the apertures have been created, the guide is removed and the implant 300 is installed on the surface of the condyle. Cement can be used to facilitate adherence of the implant 300 to the condyle.

Where more than one condyle is to be repaired, e.g., using two implants 300 of FIG. 3, or the implant 400 of FIG. 4, or where a condyle and a portion of the patellar surface is to be repaired, e.g., using the implant 500 of FIG. 5, the surgical technique described herein would be modified to, for example, provide a greater incision for accessing the joint, provide additional apertures for receiving the pegs of the implant, etc.

C. Patellar Repair System

To insert the device shown in FIG. 7, it may be appropriate to use the incisions made laterally or medially to the patella tendon and described above with respect to FIG. 2. First the patella is everted laterally and the fat pad and synovium are bent back from around the periphery of the patella. If desired, osteophytes can be removed. Prior to resurfacing the natural patella 620, the knee should be manually taken through several ranges of motion maneuvers to determine whether subluxation is present. If subluxation is present, then it may be necessary to medialize the implant 600. The natural patella can then be cut in a planar, or flat, manner such that a flat surface is presented to the implant. The geometric center of the patella 620 is then typically aligned with the geometric center of the implant 600. In order to anchor the implant 600 to the patella 620, one or more holes or apertures can be created in the patellar surface to accept the pegs 610 of the implant 600.

VI. Kits

One or more of the implants described above can be combined together in a kit such that the surgeon can select one or more implants to be used during surgery.

This description is not intended to be exhaustive or to limit the invention to the precise forms disclosed, and the generic principles defined herein can be applied to other embodiments and applications without departing from the spirit and scope as defined by the appended claims. The application of the concepts and principals extends beyond the specific embodiments described herein, which can be modified to suit particular uses contemplated, and entirely different embodiments are possible that will employ some or all of the principles described and have some, all or different advantages than those described herein. Methods recited herein may be carried out in any order of the recited events which is logically possible, as well as the recited order of events. Where a range of values is provided, it is understood that every intervening value, between the upper and lower limit of that range and any other stated or intervening value in that stated range is encompassed. Also, it is contemplated that any optional feature of the inventive variations described may be set forth and claimed independently, or in combination with any one or more of the features described herein. To the extent necessary to achieve a complete understanding disclosed, the specification and drawings of all issued patents, patent publications, and patent applications cited in this application are incorporated herein by reference.

What is claimed is:

1. A method for designing an orthopedic device that alters a wear pattern on an articular surface of a joint of a patient, comprising:
   a) receiving image data associated with the joint of the patient;
   b) determining a wear pattern of an articular surface of the joint of the patient at least in part from the image data; and
   c) designing an orthopedic device based at least in part on the image data, wherein the orthopedic device is designed to alter the wear pattern of the articular surface to a revised wear pattern and configured to replace the articular surface of the joint of the patient.

2. The method of claim 1, wherein the image data is derived from one or more techniques selected from the group consisting of arthroscopy, arthrotomic examination, gait analysis, and imaging analysis.

3. The method of claim 1, wherein the step of designing includes altering the wear pattern at least in part by adjusting the location of the wear pattern on the articular surface.

4. The method of claim 1, wherein the step of designing includes altering the wear pattern at least in part by distributing the load that will be placed on the articular surface.

5. The method of claim 1, wherein the step of designing includes altering the wear pattern at least in part by reducing point loading on the articular surface.

6. The method of claim 1, wherein the image data is received via a computer network.

7. The method of claim 1, wherein the wear pattern is determined automatically.

8. The method of claim 1, further comprising determining a second wear pattern of a second articular surface of the joint from the image data.

9. The method of claim 8, further comprising designing the orthopedic device based at least in part on the image data associated with the second articular surface, wherein the orthopedic device is designed to alter the second wear pattern of the second articular surface to a second revised wear pattern.

10. The method of claim 9, wherein the joint is a knee joint and wherein the orthopedic device is a bicompartmental resurfacing device for the knee joint.

11. The method of claim 8, further comprising designing a second orthopedic device based at least in part on the image data associated with the second articular surface, wherein the second orthopedic device is designed to alter the second wear pattern of the second articular surface to a second revised wear pattern.

12. The method of claim 11, wherein the joint is a knee joint of the patient and wherein the first orthopedic device is a tibial implant for the knee joint and the second orthopedic device is a femoral implant for the knee joint, wherein the tibial implant and the femoral implant include mating articular surfaces configured to alter the wear pattern and the second wear pattern.

13. The method of claim 1, further comprising designing a second orthopedic device based at least in part on the image data, wherein the second orthopedic device is designed to alter the wear pattern of the articular surface to the revised wear pattern.

14. The method of claim 13, wherein the orthopedic device is a tibial implant for a knee joint and the second orthopedic device is a femoral resurfacing device for the knee joint, wherein the tibial implant and the femoral resurfacing device include mating articular surfaces configured to alter the wear pattern.

15. The method of claim 1, wherein the joint is a hip joint of the patient, wherein the orthopedic device is a hip joint replacement device.

16. The method of claim 15, wherein the hip joint replacement device includes a femoral component and an acetabular component.

17. The method of claim 1, wherein the orthopedic device is designed using a library of design elements.

18. The method of claim 1, wherein the orthopedic device is designed to include at least one surface that conforms to an existing surface of the joint.

19. The method of claim 1, wherein the orthopedic device is designed to include at least one surface that is derived from an existing surface of the joint.

20. The method of claim 19, wherein the derived surface excludes a defect of the existing surface.

21. The method of claim 19, wherein the derived surface approximates an ideal surface of the joint.

22. The method of claim 19, wherein the derived surface approximates a healthy surface of the joint.

23. The method of claim 1, wherein the orthopedic device is designed to include at least one curve derived from an existing surface of the joint.

24. The method of claim 23, wherein the derived curve excludes a defect of the existing joint.

25. The method of claim 23, wherein the derived curve approximates an ideal curve of the joint.

26. The method of claim 23, wherein the derived curve approximates a healthy surface of the joint.

27. The method of claim 1, wherein the orthopedic device is designed to include at least one dimension that is derived from an existing dimension of the joint.

28. The method of claim 27, wherein the derived dimension excludes a defect of the existing joint.

29. The method of claim 27, wherein the derived dimension approximates an ideal dimension of the joint.

30. The method of claim 27, wherein the derived dimension approximates a dimension associated with a healthy joint.

31. The method of claim 1, wherein the orthopedic device is designed to be placed at least in part on cartilage associated with the joint.

32. The method of claim 1, wherein the orthopedic device is designed to be placed at least in part on subchondral bone associated with the joint.

33. The method of claim 1, further comprising producing the orthopedic device.

34. The method of claim 33, wherein the orthopedic device is produced using direct digital manufacturing.

35. The method of claim 33, wherein the orthopedic device is produced by tailoring a precursor orthopedic device.

36. The method of claim 35, wherein the precursor orthopedic device is selected from a library of orthopedic devices.

37. The method of claim 33, wherein the orthopedic device is produced by altering a standard orthopedic device.

38. The method of claim 37, wherein the standard orthopedic device is selected from an inventory of orthopedic devices.

39. The method of claim 1, wherein the orthopedic device includes at least two mating articular surfaces configured to replace the articular surface and its opposing articular surface of the joint, wherein the at least two mating articular surfaces are designed to alter the wear pattern to the revised wear pattern.

40. The method of claim 1, wherein a surface of the orthopedic device is adapted or optimized based on the wear patter.

41. The method of claim 40, wherein the adaptation or optimization includes one or more changes selected from the group consisting of: a change in material thickness; a change in material composition; a change in cross-linking properties; a change in a shape of the orthopedic device; enhanced constraint of mating articular surfaces of the orthopedic device; decreased constraint of mating articular surfaces of the orthopedic device; and any combination thereof.

42. A method for preparing a joint replacement implant for correcting an articular surface wear pattern of a patient's joint, comprising:
  a) obtaining electronic image data of an articular surface of the patient's joint;
  b) analyzing the image data for the presence or absence of wear pattern indicia;
  c) determining a wear pattern from the wear pattern indicia; and
  d) providing an implant configured to replace the articular surface of the patient's joint, wherein the implant has a characteristic topography for correcting the wear pattern to a revised wear pattern.

43. A method of creating an implant for use in joint arthroplasty to repair a patient's joint, the method comprising:
  a) obtaining electronic image data of an articular surface of the patient's joint, the articular surface of the patient's joint including a wear pattern;
  b) deriving a shape of the articular surface based, at least in part, on the image data; and
  c) providing an implant having a surface based on the shape of the articular surface and configured to replace the articular surface of the patient's joint, wherein the implant is configured to alter the wear pattern of the joint to a revised wear pattern.

44. The method of claim 43, wherein the image data is derived from one or more imaging techniques selected from the group consisting of x-ray imaging and processing; fluoroscopy; digital tomosynthesis; ultrasound; optical coherence, conventional, cone beam, or spiral computed tomography (CT); single photon emission tomography (SPECT); bone scan; positron emission tomography (PET); magnetic resonance imaging (MRI); thermal imaging; and optical imaging.

45. The method according to claim 43, wherein the patient's joint is a joint selected from the group consisting of a knee, a shoulder, a hip, a vertebrae, an elbow, an ankle, a foot, a toe, a hand, a wrist and a finger.

46. The method according to claim 43, wherein the wear pattern is based, at least in part, on one of a presence, absence, location, distribution, depth, area, or dimensions of cartilage loss; presence, absence, location, distribution, depth, area, or dimensions of subchondral cysts; presence, absence, location, distribution, depth, area, or dimensions of subchondral sclerosis; presence, absence, location, distribution, volume, area, depth or dimensions of a subchondral bone plate abnormality; presence, absence, location, distribution, or dimensions of a subchondral bone deformity; presence, absence, or severity of a varus or valgus deformity; presence, absence or severity of recurvatum or antecurvatum; and presence, absence, location, distribution, volume, depth or dimensions of bone marrow edema.

47. The method of claim 43, wherein the surface of the implant is substantially at least one of rigid, non-pliable, non-flexible and non-resilient.

48. The method of claim 43, wherein the surface of the implant comprises a material selected from the group consisting of a polymer, a cross-linked polymer, a ceramic, a metal, an alloy, a ceramic-metal composite, and combinations thereof.

49. The method of claim 43, wherein providing the surface of the implant includes a process selected from the group consisting of rapid prototyping, laser cutting, laser sintering, electron beam melting, casting, milling, and combinations thereof.

50. A method for preparing an implant for accommodating an articular surface wear pattern of a femoral condyle and/or a tibial plateau of a patient's knee joint, comprising:
  a) obtaining electronic image data of an articular surface of the femoral condyle and/or tibial plateau;
  b) analyzing the image data for the presence or absence of wear pattern indicia;
  c) determining a wear pattern from the wear pattern indicia; and
  d) providing an implant having a surface with a characteristic topography for accommodating the wear pattern, wherein the implant is configured to replace at least a portion of the femoral condyle and/or the tibial plateau.

51. The method of claim 50, wherein a shape of the surface of the implant is derived from a shape of the articular surface derived from the electronic image data.

52. The method of claim 50, wherein the implant includes a femoral component and a tibial component having mating articular surfaces configured to alter the wear pattern to a revised wear pattern.

* * * * *